US012343548B2

(12) United States Patent
Stevenson et al.

(10) Patent No.: US 12,343,548 B2
(45) Date of Patent: *Jul. 1, 2025

(54) ANISOTROPIC CONDUCTIVE ELECTRICAL CONNECTION FROM A CONDUCTIVE PATHWAY THROUGH A CERAMIC CASING TO A CIRCUIT BOARD ELECTRONIC COMPONENT HOUSED INSIDE THE CASING

(71) Applicant: Greatbatch Ltd., Clarence, NY (US)

(72) Inventors: Robert A. Stevenson, Canyon Country, CA (US); Christine A Frysz, Orchard Park, NY (US); Keith W. Seitz, Clarence Center, NY (US); Brian P Hohl, Clarence, NY (US); Marc Gregory Martino, Westlake Village, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/796,784

(22) Filed: Aug. 7, 2024

(65) Prior Publication Data

US 2024/0390688 A1 Nov. 28, 2024

Related U.S. Application Data

(63) Continuation of application No. 17/165,500, filed on Feb. 2, 2021, now Pat. No. 12,064,639, which is a
(Continued)

(51) Int. Cl.
*A61N 1/375* (2006.01)
*H01G 4/008* (2006.01)
(Continued)

(52) U.S. Cl.
CPC .......... *A61N 1/3754* (2013.01); *H01G 4/008* (2013.01); *H01G 4/1209* (2013.01); *H01G 4/236* (2013.01); *H01G 4/35* (2013.01)

(58) Field of Classification Search
CPC .... A61N 1/3754; H01G 4/008; H01G 4/1209; H01G 4/236; H01G 4/35
See application file for complete search history.

(56) References Cited

U.S. PATENT DOCUMENTS

| 3,681,612 A | 8/1972 | Kinzler et al. |
| 3,745,430 A | 7/1973 | Kerr et al. |

(Continued)

FOREIGN PATENT DOCUMENTS

| EP | 0243573 | 11/1987 |
| EP | 0145430 | 5/1991 |

(Continued)

OTHER PUBLICATIONS

"Extended European Search", Application 17201160.3 dated Apr. 16, 2018.
(Continued)

*Primary Examiner* — Lindsey G Wehrheim
(74) *Attorney, Agent, or Firm* — Michael F. Scalise

(57) ABSTRACT

An AIMD includes a ceramic base closed with a ceramic lid, both cooperatively separating body fluid and device sides. The lid and circuit board both have active and conductive pathways. A circuit board has active and ground conductive pathways. An anisotropic conductive layer disposed between the lid device side and the circuit board has a first thickness where a first conductive particle is in electrical contact with the lid and the circuit board active conductive pathways electrically connected to the active terminal of an electronic component on the circuit board, a second thickness where a second conductive particle is in electrical
(Continued)

contact with the lid and the circuit board ground conductive pathways electrically connected to the ground terminal of the electronic component. The anisotropic conductive layer has a third, greater thickness where no conductive particles are in electrical contact with the lid and circuit board conductive active and ground pathways.

23 Claims, 48 Drawing Sheets

Related U.S. Application Data continuation of application No. 16/362,043, filed on Mar. 22, 2019, now Pat. No. 10,905,888, which is a continuation-in-part of application No. 16/121,716, filed on Sep. 5, 2018, now Pat. No. 10,596,369, which is a continuation-in-part of application No. 15/943,998, filed on Apr. 3, 2018, now Pat. No. 10,350,421.

(60) Provisional application No. 62/646,522, filed on Mar. 22, 2018.

(51) Int. Cl.
*H01G 4/12* (2006.01)
*H01G 4/236* (2006.01)
*H01G 4/35* (2006.01)

(56) References Cited

U.S. PATENT DOCUMENTS

| | | |
|---|---|---|
| 3,871,382 A | 3/1975 | Mann |
| 3,961,294 A | 6/1976 | Hollyday |
| 3,968,802 A | 7/1976 | Ballis |
| 3,980,975 A | 9/1976 | Maxon et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton et al. |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh et al. |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Segawa et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,944,298 A | 7/1990 | Sholder |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,039,965 A | 8/1991 | Higgins |
| 5,044,375 A | 9/1991 | Bach et al. |
| 5,052,404 A | 10/1991 | Hodgson et al. |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,268,810 A | 12/1993 | DiMarco et al. |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A * | 7/1994 | Stevenson ............ A61N 1/3754 333/182 |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Mnclarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rhinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |
| 5,700,548 A | 12/1997 | Warnier et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |

(56) References Cited

U.S. PATENT DOCUMENTS

| | | |
|---|---|---|
| 5,735,884 A | 4/1998 | Thompson et al. |
| 5,735,887 A | 4/1998 | Barreras et al. |
| 5,741,321 A | 4/1998 | Brennen |
| 5,751,539 A | 5/1998 | Stevenson et al. |
| 5,757,252 A | 5/1998 | Cho et al. |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A | 1/1999 | Haq et al. |
| 5,864,234 A | 1/1999 | Luedeke |
| 5,867,361 A | 2/1999 | Seifried et al. |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A | 11/2000 | Haq et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,275,379 B1 | 8/2001 | Sleboda et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,888,715 B2 | 5/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |
| 6,949,929 B2 | 9/2005 | Gray et al. |
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |

(56) References Cited

U.S. PATENT DOCUMENTS

| | | |
|---|---|---|
| 6,985,775 B2 | 1/2006 | Reinke et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,035,076 B1 | 4/2006 | Stevenson |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,136,273 B2 | 11/2006 | Stevenson et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,174,223 B2 | 2/2007 | Money et al. |
| 7,199,995 B2 | 4/2007 | Stevenson |
| 7,211,103 B2 | 5/2007 | Greenberg et al. |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,489,495 B2 | 2/2009 | Stevenson |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,535,693 B2 | 5/2009 | Stevenson et al. |
| 7,551,963 B2 | 6/2009 | Rusin et al. |
| 7,561,906 B2 | 7/2009 | Atalar et al. |
| 7,586,728 B2 | 9/2009 | Anthony |
| 7,593,208 B2 | 9/2009 | Anthony et al. |
| 7,623,335 B2 | 11/2009 | Stevenson et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,797,048 B2 | 9/2010 | Stevenson et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,131,376 B1 | 3/2012 | Greenberg et al. |
| 8,163,397 B2 | 4/2012 | Ok et al. |
| 8,179,658 B2 | 5/2012 | Stevenson et al. |
| 8,219,208 B2 | 7/2012 | Stevenson et al. |
| 8,301,249 B2 | 10/2012 | Min |
| 8,494,635 B2 | 7/2013 | Guebler et al. |
| 8,528,201 B2 | 9/2013 | Guebler et al. |
| 8,588,916 B2 | 11/2013 | Satou et al. |
| 8,604,341 B2 | 12/2013 | Barry et al. |
| 8,653,384 B2 | 2/2014 | Tang et al. |
| 8,659,870 B2 | 2/2014 | Brendel et al. |
| 8,670,829 B2 | 3/2014 | Morioka et al. |
| 8,755,887 B2 | 6/2014 | Troetzschel et al. |
| 8,763,245 B1 | 7/2014 | Lucisano et al. |
| 8,841,558 B2 | 9/2014 | Satou et al. |
| 8,855,768 B1 | 10/2014 | Dabney et al. |
| 8,872,035 B2 | 10/2014 | Satou et al. |
| 8,874,206 B2 | 10/2014 | Malinowski et al. |
| 8,886,320 B2 | 11/2014 | Wollenberg et al. |
| 8,927,862 B2 | 1/2015 | Barry et al. |
| 8,929,987 B2 | 1/2015 | Troetzschel et al. |
| 8,938,309 B2 | 1/2015 | Marzano et al. |
| 9,008,779 B2 | 4/2015 | Satou et al. |
| 9,032,614 B2 | 5/2015 | Specht |
| 9,108,066 B2 | 8/2015 | Woods et al. |
| 9,233,253 B2 | 1/2016 | Stevenson et al. |
| 9,407,076 B2 | 8/2016 | Troetzschel et al. |
| 9,418,778 B2 | 8/2016 | Makino et al. |
| 9,427,596 B2 | 8/2016 | Brendel et al. |
| 9,431,814 B2 | 8/2016 | Blilie et al. |
| 9,480,168 B2 | 10/2016 | Troetzschel et al. |
| 9,492,659 B2 | 11/2016 | Brendel et al. |
| 9,552,899 B2 | 1/2017 | Specht et al. |
| 9,764,129 B2 | 9/2017 | Stevenson et al. |
| 10,350,421 B2 | 7/2019 | Stevenson et al. |
| 10,596,369 B2 | 3/2020 | Stevenson et al. |
| 12,064,639 B2 * | 8/2024 | Stevenson ............ A61N 1/3754 |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013928 A1 | 1/2003 | Saruwatari |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |

(56) References Cited

U.S. PATENT DOCUMENTS

| | | |
|---|---|---|
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0028784 A1 | 2/2006 | Brendel |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Iyer et al. |
| 2007/0179577 A1 | 8/2007 | Marshall et al. |
| 2007/0203529 A1 | 8/2007 | Iyer et al. |
| 2007/0208383 A1 | 9/2007 | Williams |
| 2007/0250143 A1 | 10/2007 | Sommer et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163974 A1 | 6/2009 | Taylor et al. |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114246 A1 | 5/2010 | Hill et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0149042 A1 | 6/2010 | Utsi et al. |
| 2010/0151113 A1 | 6/2010 | Shelton |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2010/0241206 A1 | 9/2010 | Truex et al. |
| 2011/0043297 A1 | 2/2011 | Stevenson et al. |
| 2011/0248184 A1 | 10/2011 | Shah |
| 2012/0006576 A1 | 1/2012 | Barry et al. |
| 2012/0197335 A1 | 8/2012 | Reisinger |
| 2013/0032378 A1 | 2/2013 | Morioka et al. |
| 2013/0058003 A1 | 3/2013 | Iyer et al. |
| 2013/0138186 A1 | 5/2013 | Iyer et al. |
| 2013/0184796 A1 | 7/2013 | Marzano et al. |
| 2014/0151114 A1 | 6/2014 | Morioka et al. |
| 2014/0168850 A1 | 6/2014 | Stevenson et al. |
| 2014/0168917 A1 | 6/2014 | Marzano et al. |
| 2014/0243944 A1 | 8/2014 | Stevenson et al. |
| 2015/0004359 A1 | 1/2015 | Shahbazi et al. |
| 2015/0217111 A1 | 8/2015 | Stevenson et al. |
| 2015/0245468 A1 | 8/2015 | Barry et al. |
| 2015/0283374 A1 | 10/2015 | Kronmueller et al. |
| 2015/0314131 A1 | 11/2015 | Marzano et al. |
| 2015/0343224 A1 | 12/2015 | Woods et al. |
| 2016/0151635 A1 | 6/2016 | Frysz et al. |
| 2016/0263384 A1 | 9/2016 | Stevenson et al. |
| 2016/0287883 A1 | 10/2016 | Barry et al. |

(56) References Cited

U.S. PATENT DOCUMENTS

| | | |
|---|---|---|
| 2018/0126175 A1 | 5/2018 | Seitz et al. |
| 2018/0126176 A1 | 5/2018 | Seitz et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0498996 | 3/1997 |
| EP | 1021730 | 4/2003 |
| EP | 0930509 | 3/2004 |
| EP | 1469910 | 12/2006 |
| EP | 2025361 A1 | 9/2007 |
| EP | 1883449 | 1/2009 |
| EP | 2025361 | 2/2009 |
| EP | 2617461 A1 | 7/2013 |
| EP | 2013158552 | 10/2013 |
| FR | 2811900 B1 | 2/2003 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2004254257 | 9/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2006118641 A1 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 A3 | 6/2008 |
| WO | 2008111986 | 9/2008 |
| WO | 2008111986 A1 | 9/2008 |
| WO | 2010008833 | 1/2010 |
| WO | 2010008833 A1 | 1/2010 |
| WO | 2013/158552 | 10/2013 |

OTHER PUBLICATIONS

"Extended European Search", Application No. 17197151.8, dated Apr. 26, 2018.

"Extended European Search Report", Application No. 16175505.3, dated Nov. 15, 2016.

"Extended European Search Report", Application No. 18177098.3, dated Aug. 8, 2018.

"Holy Stone Enterprise", Ceramic Capacitor Catalog 2008-2009, May 2008.

"Wikipedia article", EIA Class 1 dielectric., Sep. 13, 2006.

Balanis, Constantine A., "Advanced Engineering Electromagnetics", 1989.

Becker, Von R., "Die Keimbildung Bei Der Ausscheidung in Metallischen Mischkristallen", Published in Annalen der Physik, Issue 5, vol. 32, 1938, pp. 128-140.

Boser, Otmar, et al., "High Frequency Behavior of Ceramic Multilayer Capacitors", IEEE Transactions on Components, Hybrids, and Manufacturing Technology, vol. CHMT-10, No. 3, Sep. 1987, 437-439.

Clement, Wes, et al., "Estimation of Effective Lead Loop Area for Implantable Pulse Generators and Cardioverter/Defibrillators for Determination of Susceptibility to Radiated Electromagnetic Interference", AAMI EMC Task Force, Apr. 12, 2004, 10 pages.

Gabriel, S., et al., "The Dielectric Properties of Biological Tissues: II.", Measurements in the Frequency Range 10 Hz to 20 GHz, Apr. 2, 1996, 2251-2269.

Gabriel, S., et al., "The Dielectric Properties of Biological Tissues: Parametric Models for the Dielectric Spectrum of Tissues", Parametric Models for the Dielectric Spectrum of Tissues Phys. Med. Bio. 41, 1996, 2271-2293.

Karbasi, Ali, "Developing a High Density Pt/Alumina Hermetic Feedthrough", Florida International University, FIU Digital Commons, FIU Electronic Theses and Dissertations, University Graduate School, Published Jun. 15, 2012.

Kingery, W. D., et al., "Atom Mobility in Introduction to Ceramics, 2nd Edition", Published in New York, Wiley, copyright 1976, pp. 217-263.

Kingery, W. D., et al., "Surfaces, Interfaces, and Grain Boundaries in Introduction to Ceramics", 2nd Edition, Publiched in New York, Wiley, copyright 1976, pp. 177-215.

Konings, Mauritis K, et al., "Heating Around Intravascular Guidewires by Resonating RF Waves", Journal of Magnetic Resonance Imaging, 2000, 79-85.

Lamouri, Samir, et al., "Control of the y-alumina to a-alumina phase transformation for an optimized alumina densification", Boletin de la Sociedad Espanola De Ceramica Y Vidrio 56 (2017) pp. 47-54.

Olenick, John A., "Ultrathin Flexible Ceramics for Electronics Applications", www.ceramicindustry.com—Product Profile, Oct. 2016, pp. 30 and 31.

Roguin, Ariel, et al., "Modern Pacemaker and Implantable Cardioverter/ Defibrillator systems can be Magnetic Resonance Imaging Safe", Journal of the American Heart Association, Aug. 4, 2004, 475-482.

Sakabe, Yukio, et al., "High Frequency Performance of Multilayer Ceramic Capacitors", Electronic Components and Technology Confrerence, 1995, Proceedings 45th, May 21, 1995, 234-240.

Sarda, Ivan G., et al., "Ceramic EMI Filters—A Review", American Ceramic Society Bulletin; vol. 67, No. 4, 1988, 737-746.

Shellock, F. G., et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.

Shellock, Frank G., "MRI Issues for Neuromodulation Devices", Institute for Magnetic Resonance Safety Education, and Research (IMRSER).

Susil, Robert C., et al., "Multifunctional Interventional Devices for MRI: A Combined Electrophysiology/MRI Catheter", 2002, 594-600.

Susil, Robert C., et al., "U.S. Appl. No. 60/283,725", Multifunctional Interventional Devices for Use in MRI, Apr. 13, 2001.

Weiner, Michael J., et al., "U.S. Appl. No. 60/269,817", Electromagnetic Interference immune Cardiac Assist System, filed Feb. 20, 2001.

"European Search Report", Application No. 15165863.0, dated Sep. 12, 2016.

"European Search Report", Application No. 18150642.9, dated Jun. 6, 2018.

(56) References Cited

OTHER PUBLICATIONS

"European Search Report", Application No. 12157697.9, dated Jul. 5, 2012.

* cited by examiner

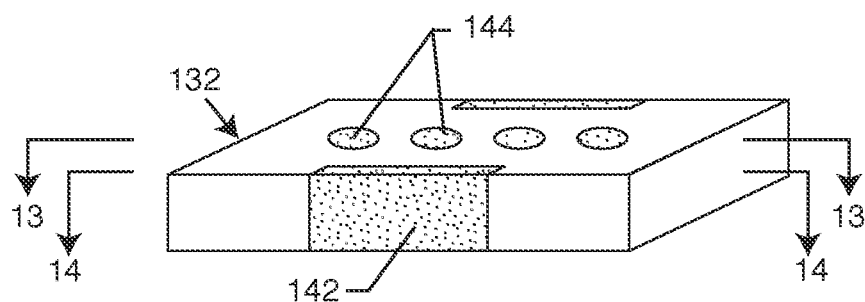
FIG. 11
PRIOR ART
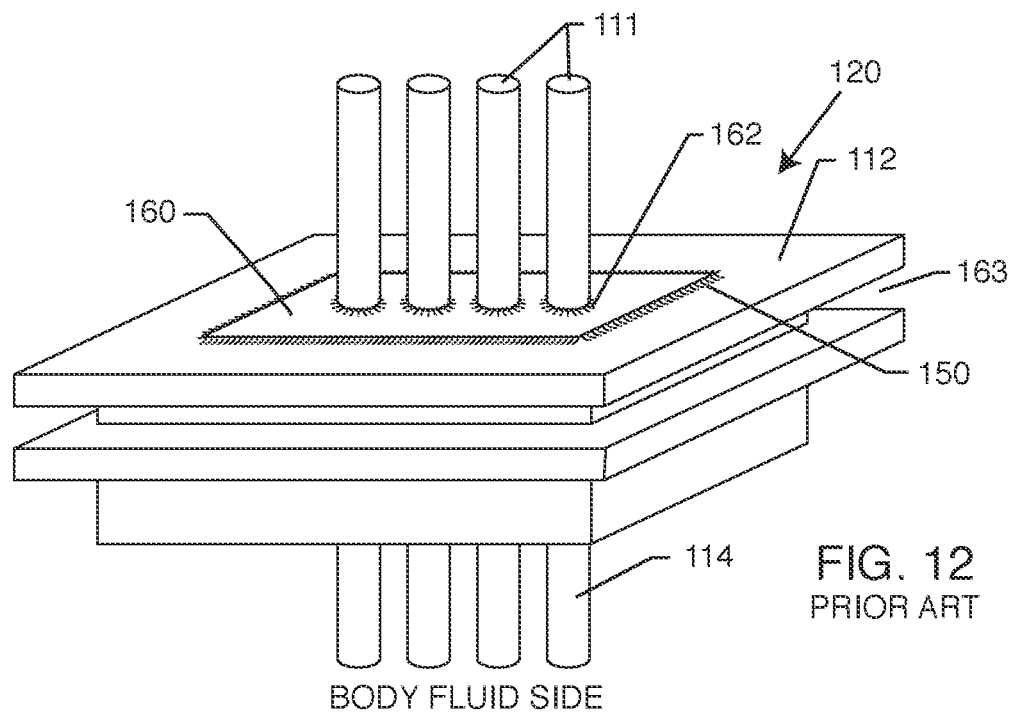
FIG. 12
PRIOR ART
BODY FLUID SIDE
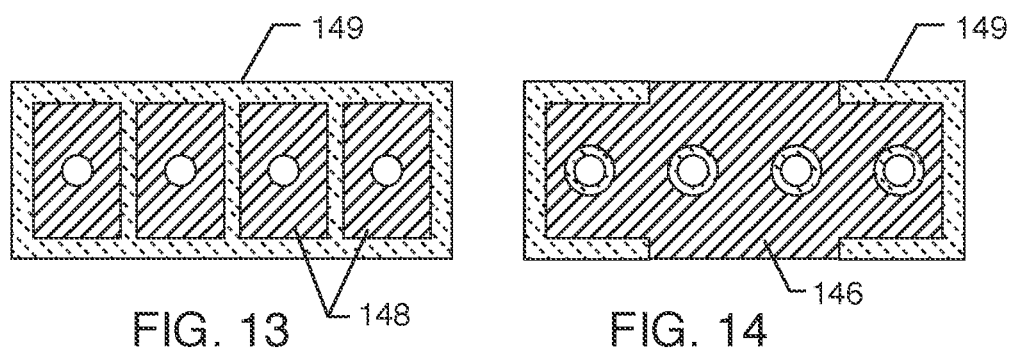
FIG. 13
PRIOR ART
FIG. 14
PRIOR ART

BODY FLUID SIDE
PRIOR ART

BODY FLUID SIDE
PRIOR ART

BODY FLUID SIDE

BODY FLUID SIDE

BODY FLUID SIDE

BODY FLUID SIDE

BODY FLUID SIDE

BODY FLUID SIDE

BODY FLUID SIDE

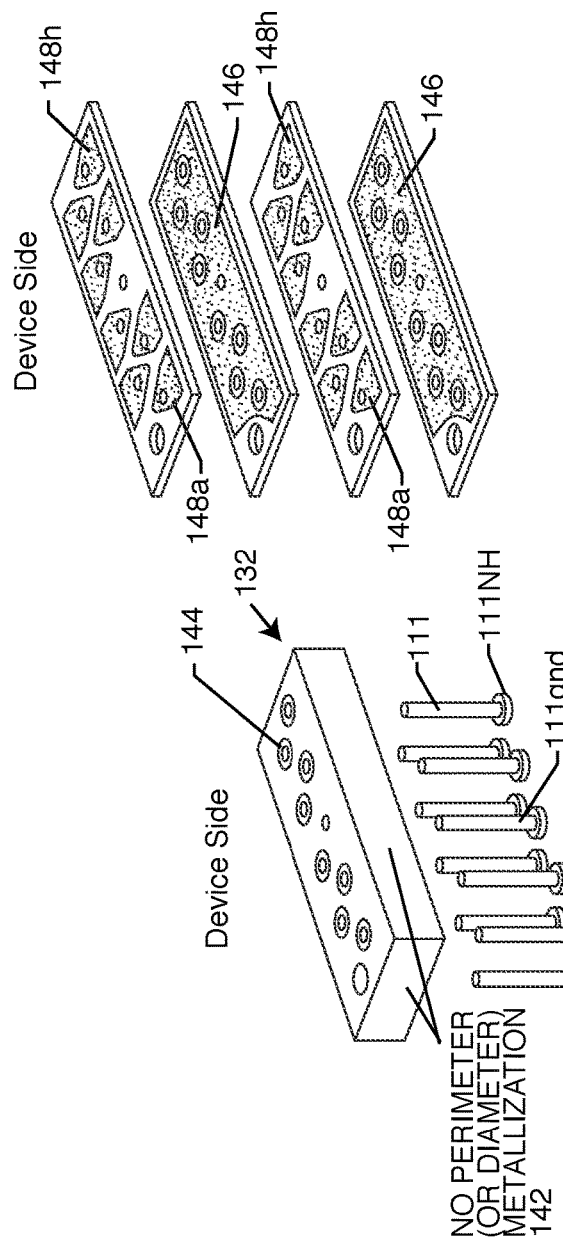
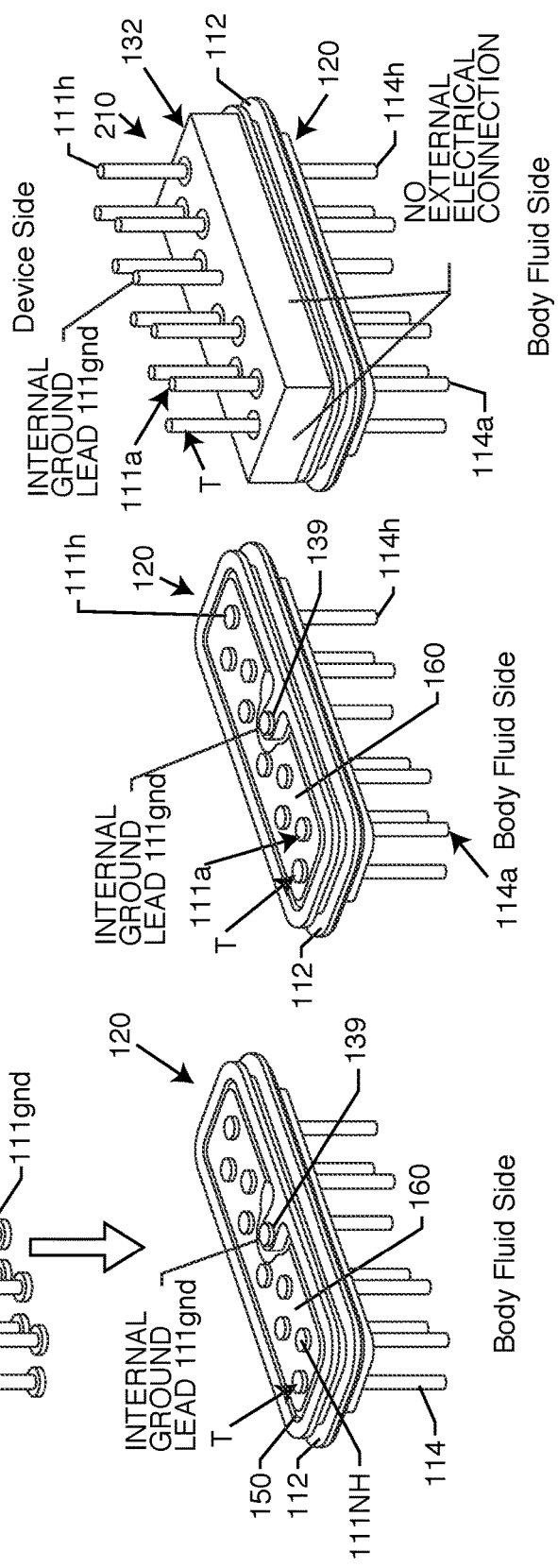
FIG. 32A
FIG. 32B
FIG. 32C

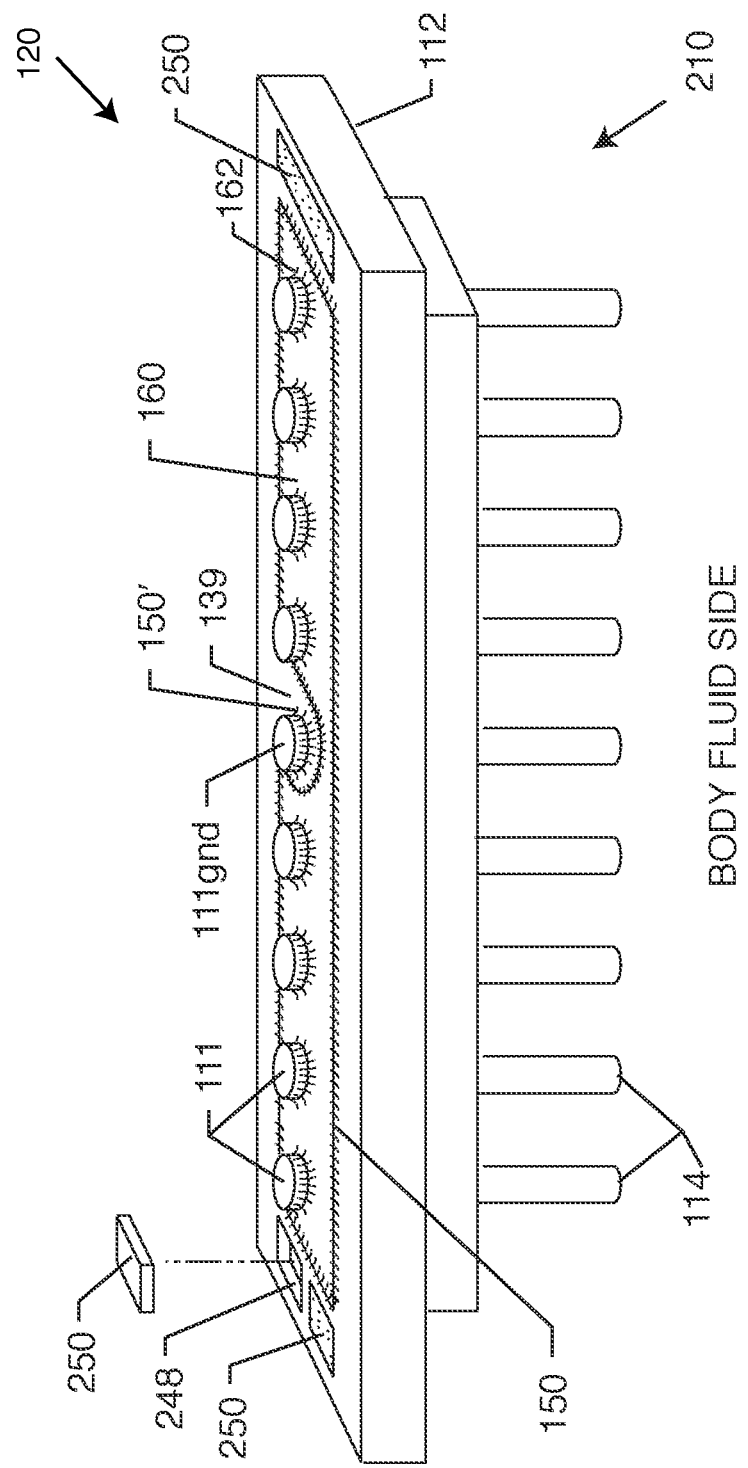

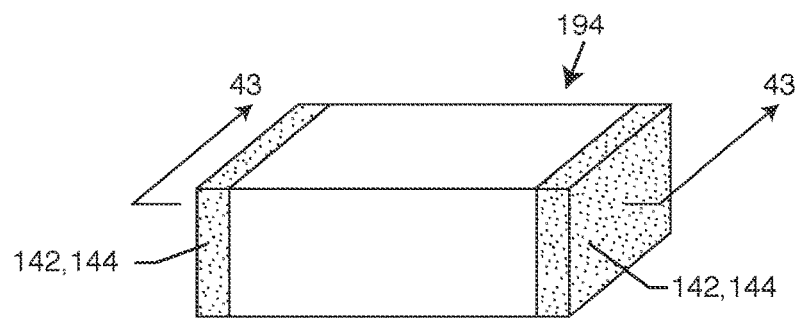
FIG. 42
PRIOR ART
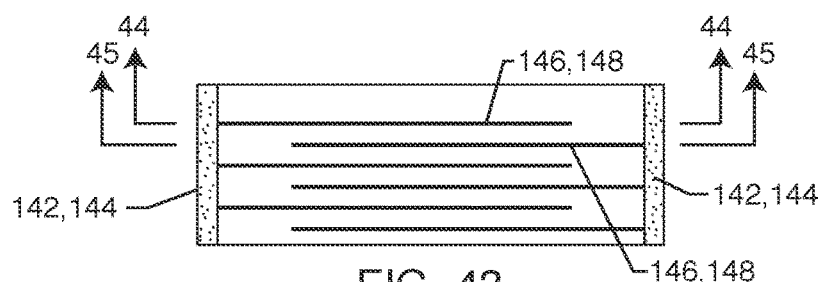
FIG. 43
PRIOR ART
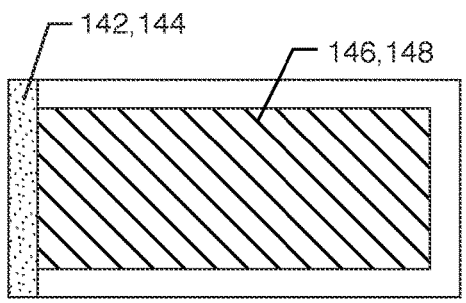 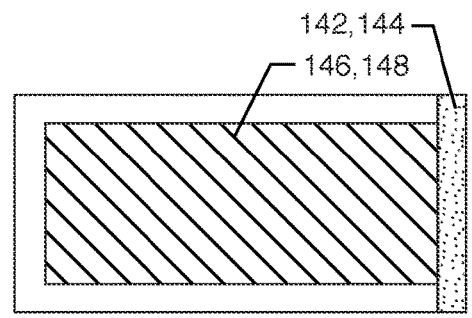
FIG. 44            FIG. 45
PRIOR ART            PRIOR ART

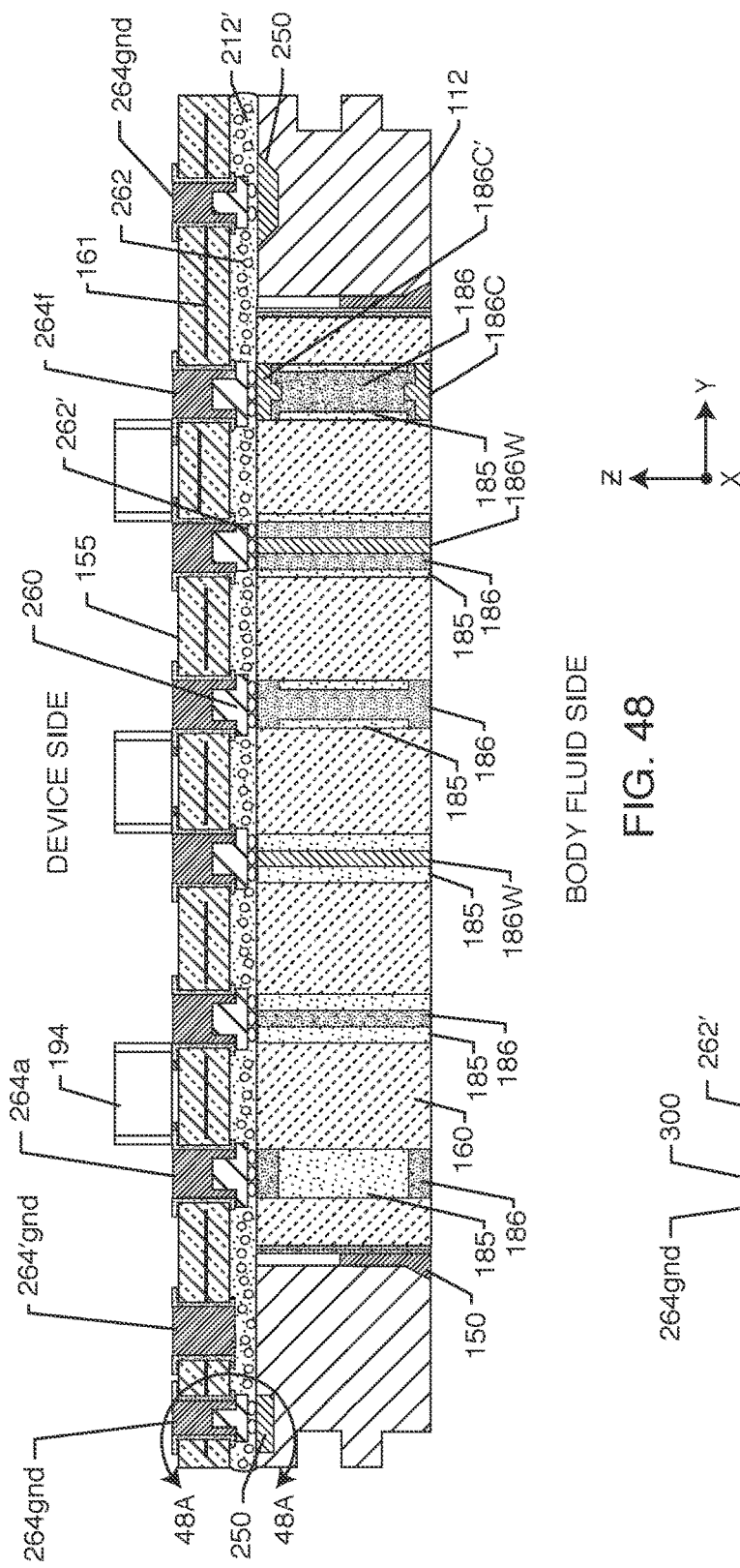
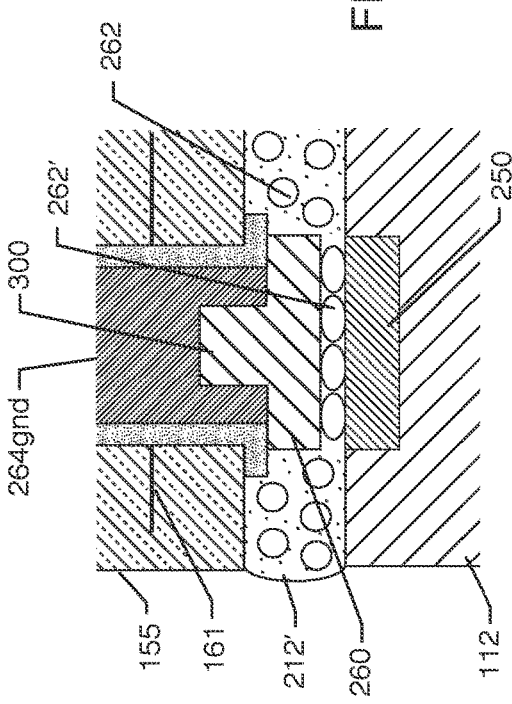
FIG. 48
FIG. 48A

ANISOTROPIC CONDUCTIVE ELECTRICAL CONNECTION FROM A CONDUCTIVE PATHWAY THROUGH A CERAMIC CASING TO A CIRCUIT BOARD ELECTRONIC COMPONENT HOUSED INSIDE THE CASING

CROSS-REFERENCE TO RELATED APPLICATIONS

This is a continuation application of U.S. application Ser. No. 17/165,500, filed on Feb. 2, 2021, now U.S. Pat. No. 12,064,639, which is a continuation application of U.S. application Ser. No. 16/362,043, filed on Mar. 22, 2019, now U.S. Pat. No. 10,905,888, which is a continuation-in-part application of U.S. application Ser. No. 16/121,716, filed on Sep. 5, 2018, now U.S. Pat. No. 10,596,369, which is a continuation-in-part application of U.S. application Ser. No. 15/943,998, filed on Apr. 3, 2018, now U.S. Pat. No. 10,350,421, which claims priority to U.S. provisional application Ser. No. 62/646,522, filed on Mar. 22, 2018, the contents of which are fully incorporated herein by reference.

FIELD OF THE INVENTION

The present invention generally relates to active implantable medical devices and hermetic terminal subassemblies. More particularly, the present invention relates to a hermetic terminal for an active implantable medical device having an anisotropic conductive layer electrically connecting the hermetic feedthrough to a feedthrough filter capacitor disposed on the device side.

BACKGROUND OF THE INVENTION

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The leadwires that come from a deep brain stimulator are often placed using real time imaging. Most commonly such leadwires are placed during real time MRI. 100C shows a cardiac pacemaker, which is well-known in the art, may have endocardial or epicardial leads. Implantable pacemakers may also be leadless. The family of cardiac pacemakers 100C includes the cardiac resynchronization therapy devices (CRT-D pacemakers) and leadless pacemakers. CRT-D pacemakers are unique in that, they pace both the right and left sides of the heart. The family also includes all types of implantable loop recorders or biologic monitors, such as cardiac monitors. 100D includes the family of left ventricular assist devices (LVAD's) and artificial hearts. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic monitoring and/or data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators. ICDs, as used herein, include subcutaneous defibrillators and also CRT-D devices. CRT devices are cardiac resynchronization therapy devices that could also provide high-voltage defibrillation. 100K includes a family of implantable retinal stimulators devices. In summary, as used herein, the term AIMD includes any device implanted in the human body that has at least one electronic component.

FIG. 2 illustrates a prior art cardiac pacemaker 100C showing a side view. The pacemaker electronics are housed in a hermetically sealed and conductive electromagnetic shield 102 (typically titanium). There is a header block assembly 104 generally made of thermal-setting non-conductive plastic, such as Tecothane®. This header block assembly 104 houses one or more connector assemblies generally in accordance with ISO Standards IS-1, IS-2, or more modern standards, such as IS4 or DF4. These header block connector port assemblies are shown as 106 and 106'. Implantable leadwires 110, 110' have proximal plugs 108, 108' and are designed to insert into and mate with these header block connector cavities 106 and 106', or, in devices that do not have header block assemblies built directly into the pulse generator itself.

As used herein, the term "lead" refers to an implantable lead containing a lead body and one or more internal lead conductors. A "lead conductor" refers to the conductor that is inside of an implanted lead body. The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin or even a circuit trace. As described herein, composite conductive sintered paste filled vias passing through an insulator in nonconductive relation with a ferrule electrically acts the same as leadwire, lead wire, or pin. These sintered-paste filled vias may also incorporate co-fired solid leadwires. As used herein, the term paste generally refers to pastes, inks, gels, paints, cermets, and other such metal and/or metal/ceramic sinterable material combinations that can be flowable, injectable, pressed, pulled, pushed or otherwise movable into an orifice or via. Post-sintering, the solvents and binders are baked out and, after sintering, the paste becomes a densified solid with monolithic structure. Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

FIG. 3 illustrates a prior art unipolar feedthrough capacitor 132. A quad polar feedthrough capacitor 132 was previously illustrated in prior art FIG. 2. Referring to FIG. 3, one can see that there's an external metallization 142 and a passageway or feedthrough hole metallization 144. This metallization can be applied by electroplating or by applying a fritted glass, which is then fired. In one embodiment, the fritted glass may comprise a silver or palladium silver glass matrix. In any event, after application of the metallization layers 142 and 144, one can make electrical contact to the feedthrough capacitor either by soldering or thermal-setting conductive adhesives or the like. As shown, the feedthrough capacitor comprises active electrode plates 148 and ground electrode plates 146. The reason the electrode plates 146 are called ground electrode plates and as will be further explained herein, is because the perimeter or outside diameter metallization 142 is configured to be attached to a ferrule and in turn, to the conductive housing of an AIMD, which forms an equipotential surface for energy dissipation (aka ground). Referring once again to FIG. 2, one can see that the housing 116, for an active implantable medical device, is generally metallic (titanium). One can also see that the feedthrough capacitor 132 is attached to a hermetically sealed subassembly 120 of the AIMD, which acts as a equipotential surface (ground).

FIG. 3A is taken generally from section 3A-3A from FIG. 3. Shown in exploded view, are ceramic cover sheets 147, active electrodes 148 that are disposed on ceramic layers 149 and ground electrode plates 146 that are disposed on ceramic layers 149. These are stacked up with cover sheets on the opposite end 147 and then pressed and laminated. It will be appreciated that blank cover sheets 147 can be disposed between the active layers 148 and the ground layers 146 thereby, increasing the dielectric thickness and increasing the voltage rating of the device. The electrode layers 148 and 146 are typically applied by silk-screening or equivalent waterfall processes.

FIG. 4 is a cross-sectional view showing the unipolar capacitor 132 of FIG. 3 mounted to a ferrule 112 of a hermetic seal subassembly 120 for an AIMD. The ferrule 112 hermetically seals an opening 115 of the housing 116 of the AIMD 100. As can be seen, the ground metallization 142 of the feedthrough capacitor 132 is electrically connected 152 to the ferrule 112 of the hermetic seal. The hermetic seal 150 is accomplished generally by gold brazing between an alumina insulator 160 that is usually disposed within a ferrule opening 113. Due to the hermetic seal, the ferrule and the insulator cooperatively separate a body fluid side from a device side, the body fluid side residing outside the AIMD housing and device side residing inside the AIMD housing. There is an outside diameter gold braze 150 between the insulator and the ferrule 112. There is also a gold braze 162 between leadwires 114, 111 and the inside diameter of an insulator 160 passageway 134 as illustrated. In order for gold braze material 150, 162 to wet to the insulator surfaces 160, there must first be an adhesion layer 153 and then a wetting layer 151, as illustrated. In one embodiment, the adhesion layer can be a sputtered layer of titanium, followed by a sputtered layer of molybdenum or niobium (the wetting layer). In some manufacturing agent operations, the adhesion and wetting layers can be combined into a single layer. Throughout the present invention, sometimes in order to simplify, the adhesion layer 153 and wetting layer 151 are not shown or at least not described. However, it will be understood that anywhere that a gold braze is described herein to an insulator 160, that an adhesion/wetting layer is required.

As defined herein, what is referred to as the insulator is generally disposed between or inside a ferrule opening and has either lead conductors or conductive passageways or vias that pass through the hermetic terminal subassembly 120. The ceramic capacitor 130 also uses insulative materials, which are dielectrics. As previously described in FIG. 3A, these dielectric sheets 147, 149 are referred to as dielectrics although it is appreciated that they are also insulative. In summary, as used herein, insulators are the insulators that are gold brazed to a ferrule of the AIMD, whereas capacitor dielectric insulators are referred to as dielectric layers.

Referring once again to FIG. 4, one can see that the ferrule 112 of the hermetic seal has been laser welded 154 into the overall housing 116 of the AIMD. This is very important in that the feedthrough capacitor ground metallization 142 becomes part of the overall electromagnetic shield of the AIMD housing. This forms in the industry what is known as a Faraday cage and provides an effective electromagnetic interference shield and energy dissipating surface. Referring back to FIG. 4, lead 114 on the body fluid side is generally connected to implanted leadwires and electrodes (not shown). Referring back to FIG. 2 for a prior art pacemaker, one can see these leadwires 107 and 107' that are connected to electrodes 109 that are located within the human heart. Again, referring to FIG. 2, undesirably, electromagnetic interference (EMI) can be coupled to these implanted leads and in turn, to the interior of the AIMD housing. It has been shown in numerous articles that EMI can disrupt the proper operation of the AIMD, such as a cardiac pacemaker and lead to improper therapy or even complete inhibition of therapy. Inhibition of therapy, for a cardiac pacemaker, can be immediately life-threatening to a pacemaker dependent patient.

Referring once again to FIG. 4, electromagnetic interference signals therefore, may be conducted along leadwire 114 to terminal 1 of the feedthrough capacitor. It is the purpose of the feedthrough capacitor 132 to divert unwanted high-frequency EMI signals from the leadwire 114, 111 so that by the time the signals reach terminal 2 (the AIMD electronics or device side), that the electromagnetic interference has been greatly attenuated or diverted through the feedthrough capacitor, harmlessly to the AIMD housing 116. This is further appreciated by looking at the schematic diagram of FIG. 4A. Electromagnetic interference signals enter terminal 1 of the 3-terminal feedthrough capacitor and are diverted harmlessly to the ground terminal 3 (116) before they can reach the device side 111, terminal 2.

The feedthrough capacitors 132, when properly installed, acts electrically as a continuous part of the titanium shield 116, which houses the active implantable medical device (AIMD). The feedthrough capacitor is a 3-terminal coaxial device whose internal electrode plates "plug the hole" and both reflect and absorb EMI fields. The feedthrough capacitor is novel in that, it is a broadband low pass filter, which allows desirable frequencies (like pacing pulses) to pass. Because it is a unique 3-terminal coaxial device, it provides effective attenuation to undesired signals (EMI) over a very broad band (10 MHz to 10 GHZ frequency range). When designed and installed properly, feedthrough capacitors are very low inductance devices, which do not series resonate. It is very important that feedthrough capacitors be installed in such a way that undesirable resistances, for example, due to titanium oxides, cannot occur in the ground connection.

FIG. 5 is very similar to the schematic of FIG. 4A, except in this case, there is an oxide $R_{oxide}$, as illustrated. This oxide comes from undesirable oxidation of the ferrule 112 previously illustrated in FIG. 4. The electrical connection material 152 illustrated in FIG. 4, is connected to a titanium surface of the ferrule 112. As will be explained, titanium can undesirably form oxides, which become resistive and reduce the effectivity of the feedthrough capacitor 132.

FIG. 6A is taken from FIG. 21 of U.S. Pat. No. 5,333,095, the contents of which are incorporated herein fully by reference. Referring once again to FIG. 6A, one can see that there is a feedthrough capacitor 132 that is mounted onto a ferrule 112 of a hermetic seal subassembly 120. In this case, the diameter of the bipolar feedthrough capacitor (in this case, two passageways instead of one) greatly overhangs the ferrule 112. In this assembly, the steps are first, that the ferrule 112 (without the presence of the feedthrough capacitor 132) is first captured by two AIMD can halves 116, 116'. These are captured as a sandwich and then laser weld is performed between the ferrule 112 and the can halves 116, 116'. The feedthrough capacitor 132 has been subsequently added and an electrical connection has been formed between the feedthrough capacitor ground metallization 142 and to the exposed areas of the AIMD housing 116, 116'. In other words, in this case, there is no direct electrical connection between the feedthrough capacitor ground metallization 142 and the ferrule 112. However, as previously described in FIG. 5, FIG. 6B illustrates the schematic of the bipolar feedthrough capacitor of FIG. 6A. Again, undesirably, an oxide $R_{oxide}$ appears between the bipolar feedthrough capacitor and ground. As will be explained, this can seriously degrade filter performance.

FIG. 7A illustrates a quad polar feedthrough capacitor (meaning four passageways). It will be appreciated that any number of feedthrough holes 134, 144 can be produced. As previously described for the unipolar capacitor of FIG. 3, the quad polar capacitor of FIG. 4, has ground metallization 142 and four passageways. Each of the passageways has its own active metallization 144. As used herein, the term active means an electrically active lead or passageway as opposed to a grounded connection. Active passageways may conduct therapeutic pacing pulses, biological sensing signals or even high-voltage therapeutic shocks. For a neurostimulator application, active passageways may include AC, pulse, triangular or many other different types of waveforms; for example, for a spinal cord stimulator to create paresthesia.

FIG. 7B is taken generally from FIG. 7B-7B from FIG. 7A, which illustrates the quad polar feedthrough capacitor in cross-section. One can see that there are ground electrode plates 146, which are disposed through the feedthrough capacitor structure and connected to the ground metallization 142. One can also appreciate that each of the feedthrough holes 134 has its own set of active electrodes 148 that are disposed and overlapping or sandwich-type construction between the ground electrode plates 146. It is the overlapping of the active and ground electrode plates in the dielectric that create the individual feedthrough capacitors. Each of the four feedthrough capacitors are associated with its own passageway metallization 144.

FIG. 8 is an exploded view of the unipolar capacitor previously illustrated in FIGS. 7A and 7B. As for the unipolar capacitor of FIG. 3A, there are cover sheets 147 and then an active layer showing four active electrodes 148 that are each individually associated with one of the four passageways. As one can see, the ground electrode layer 146 extends in non-conductive relationship with the active passageways to the feedthrough capacitors outside diameter. As before, these are stacked up in interleave relationship to form a quad polar feedthrough capacitor.

FIG. 9 is the schematic drawing of the feedthrough capacitor of FIG. 8, but in this case, this is after the feedthrough capacitor has been installed to a hermetic seal ferrule and insulator with pins, as previously described in FIGS. 2, 4 and 6A. It is assumed that the feedthrough capacitor outside diameter metallization 142 has been connected directly to either the titanium ferrule 112 or the AIMD housing 116. In both cases, the ferrule and/or the housing would be of titanium and would be subject to oxidation. Accordingly, in the schematic drawing of FIG. 9, one can see that there is an undesirable $R_{oxide}$ shown between each of the feedthrough capacitors 132 and ground 116 (AIMD housing). Referring once again to FIG. 9, one can see that each of the feedthrough capacitors 132 is labeled with terminals 1, 2 and 3. At DC or direct current, there is no difference between terminals 1 and 2 as that is a solid through-pin or leadwire or passageway. However, at RF frequencies, the feedthrough capacitor 132 substantially attenuates frequencies coming from the body fluid side from terminal 1 into the inside of the AIMD housing or device side to terminal 2. As previously stated, these undesirable EMI signals that are entering at terminal 1, are diverted by capacitive reactance through the feedthrough capacitor to ground terminal 3.

Referring once again to FIG. 7A, it will be appreciated that feedthrough capacitors can have a much higher channel count than just quad polar. Feedthrough capacitors can have tens or even hundreds of through holes.

FIG. 10 illustrates what is known in the industry as a flat-thru capacitor. The naming of "flat-thru capacitor" was coined at two different conferences, both held in 1999. Both of these are listed in the IDS. The first one is entitled, A CAPACITOR'S INDUCTANCE: CRITICAL PROPERTY FOR CERTAIN APPLICATIONS and the second paper is entitled, A CAPACITOR'S INDUCTANCE. Both of these papers include drawing 10 and again, coined the term flat-thru capacitor for this unique type of 3-terminal capacitor. Flat-thru capacitors work very similar to a manner previously described in the prior art feedthrough capacitors. They have three terminals: 1, 2 and 3, as noted on FIG. 10. The way a flat-thru capacitor works is best understood by looking at their internal electrode plates, as illustrated in FIG. 10A. Element 375 is a set of active electrode plates, which can vary from one electrode plate set to hundreds interleaved with the ground electrode plates 378 and 378', as illustrated. What is novel about flat-thru capacitors is that circuit currents, illustrated in FIG. 10 as $i_1$ can pass through the capacitor from terminal 1 to terminal 2 through the active electrode plate set 375. This in marked contrast to prior art feedthrough capacitors which have a leadwire passing through. It is true the leadwire does have a terminal 1 and a terminal 2, but circuit currents pass through the leadwire from outside the AIMD on the body fluid side to the inside of the AIMD where the AIMD circuits are. In the case of prior art feedthrough capacitors, these circuits currents $i_1$ never pass through the actual electrode plates of the feedthrough capacitor. However, for the flat-thru capacitor, these circuit currents $i_1$ pass through the active electrodes. Referring now back to FIG. 10, one can see that there is an active termination 380 on the left-hand side and a second active termination 382 on the right-hand side. These form terminals 1 and 2 of the 3-terminal capacitor. There are also ground terminations 390 shown as illustrated. These may be separate ground terminations, or the ground termination may form a stripe all the way around the top and bottom of the flat-thru capacitor (not shown). Electrical connection materials 323, such as solder or thermal-setting conductive adhesives, are used to connect the flat-thru capacitor ground termination 390 to corresponding circuit traces 322, as indicated. The active terminations 380 and 382 are generally electrically connected 383 also using solder or thermal-setting conductive adhesives, in this case, to active circuit traces 384 and 386. Three-terminal flat-thru capacitors for active medical devices are more thoroughly described in U.S. Provisional Patent Application Ser. No. 62/815,384, the contents of which are incorporated herein fully by reference.

Referring once again to FIG. 10, one can see that there is a frequency at which undesirable EMI 388 can couple all the way across the flat-thru capacitor from terminal 1 to terminal 2 by radiation. This is undesirable, but for AIMDs, it's really not much of a problem. This type of undesirable coupling 388 would generally occur in the frequency ranges between 3 and 20 GHz. Fortunately, the human body effectively reflects and absorbs frequencies at 3 GHZ and above, so flat-thru capacitors become ideal candidates for use as EMI filters in AIMDs.

FIG. 11 illustrates a prior art rectangular feedthrough capacitor 132, which has the same number of poles (4, quadpolar) as previously illustrated in FIG. 7A. This illustrates that feedthrough capacitors can be round (sometimes called discoidal), rectangular or even any other shape. As previously mentioned, the feedthrough capacitor can be quad polar, as illustrated, or any other number of feedthrough holes 144. Referring once again to FIG. 11, the ground metallization 142 is shown being brought out to both of the long sides of the feedthrough capacitor 132. This is best understood by referring to FIG. 14, which is taken generally from section 14-14 from FIG. 11. This illustrates the ground electrode plates and the fact that they are only exposed along the capacitor's long sides where metallization 142 can be applied. Also shown as FIG. 13, which is taken generally from section 13-13 from FIG. 11, illustrating four active electrodes 148. Each of these active electrodes is associated with one of the active terminal pins 111, 114. The feedthrough capacitor, as illustrated in FIG. 11, is shown ready for installation on top of a hermetic seal subassembly 120 that's illustrated in FIG. 12. Referring to FIG. 12, one can see that there is a metallic ferrule, which is typically of titanium, an insulator, which is typically of alumina and four pins or leadwires 111, 114. A hermetic and mechanical seal is effective between each of the pins 111, 114 and the insulator 160 by gold brazes 162. Also, the rectangular perimeter of the alumina insulator 160 is shown gold brazed 150 to the ferrule 112.

FIG. 15 illustrates the feedthrough capacitor 111 installed to the hermetic seal assembly 120, as previously described in FIGS. 11 and 12. As can be seen, there is an electrical connection material 152, which connects from the capacitor's ground metallization 142 directly to the ferrule 112.

FIG. 16 is taken generally from section 16-16 from FIG. 15. In this section, one can see that there is a gold braze 150 that forms a mechanical and hermetic seal between the insulator 160 and ferrule 112. There is also a hermetic seal gold braze 162 between the insulator 160 and leadwire 111, 114. In this case, the feedthrough capacitor 132 is generally larger in diameter than the gold braze hermetic seal area 150. In this case, one can see the electrical attachment material 152 connecting between the capacitor 132 ground metallization 142 into the ferrule. Layer 164 illustrates a highly undesirable oxide layer on the titanium surface of ferrule 112. Oxide layer 164 would appear all over the surfaces of the titanium ferrule 112 but is shown disposed only between the electrical attachment material 152 and the ferrule for simplicity. Referring once again to FIGS. 15 and 16, one can see that the ferrule 112 has an h-flange type shape 163. This is for capturing and subsequent laser welding of AIMD housing halves 116.

FIGS. 11 through 20 herein were all taken from FIGS. 11 through 20 of U.S. Pat. No. 9,427,596 (i.e., '596 patent), the contents of which are incorporated herein fully by reference. The '596 patent includes a detailed technical description of the capacitor's equivalent series resistance, the importance of parasitic resistance (ohmic loss) and the problem with oxides of titanium.

FIG. 17 is a schematic diagram illustrating the undesirable presence of $R_{oxide}$ in the ground path of the quad polar feedthrough capacitor. This $R_{oxide}$ results from the oxide layer 164 previously described in FIG. 16.

FIG. 18 shows the use of novel gold braze bond pads 165 that are one embodiment of a novel feature of the '596 patent. This is best understood by referring to FIG. 19 showing that the feedthrough capacitor 132 ground metallization 142 is electrically attached 152 by a thermal-setting conductive adhesive or a solder or the like directly to this gold bond pad area 165. It is well known that gold is a very noble material and does not oxidize. When sufficiently thick, a layer of gold will effectively block titanium oxides from interfering with the high-frequency electrical connection material 152. This is best understood by referring to FIG. 20, which is taken from section 20-20 from FIG. 19. In the cross-section, one can see the electrical connection material 152 that effects a very low impedance and low resistant electrical connection between the feedthrough capacitor ground metallization 142 and the gold braze pad area 165. During gold brazing, the gold braze pad 165 forms a continuous part of the hermetic seal 150 that effects a mechanical and hermetic joint to the insulator 160. In other words, an essential feature of the '596 patent, is that the low impedance, low resistance ground attach area is continuous with and one of the same width, as the same hermetic seal 150 that forms the hermetic seal gold braze.

FIG. 20A is taken from section 20A-20A from FIG. 19. FIG. 20A shows a serious deficiency in the central design concept of the '596 patent. That is, the gold braze 165 is not contained in such a way that it cannot be affected by gravitational forces during high-temperature gold braze furnace operations. As previously mentioned, during high-temperature gold brazing operations, the gold becomes molten or even liquid and due to gravitational forces, can flow out of a defined pocket area as previously illustrated in pocket area 165 in FIG. 20. In other words, it has a tendency to run down, as shown as 165' in FIG. 28. Again, as with the deficiency in Wolf, this does leave behind a thin layer of gold, however, in order to overcome this, an excessive amount of gold must be used, and one must rely on reduced contact area for the electrical connection material 152', as illustrated. By carefully controlling the fit-up tolerances between the alumina insulator 160 and the inside diameter of the ferrule 112, one can minimize the gold braze gravitational rundown 165'. However, this makes for a more expensive process and the need to hold the individual pieces to very tight tolerances.

Referring once again to FIG. 20A, one can see that there is a thin layer of gold 165T that is left behind. The problem is that this uncontrolled thin layer may or may not be oxide-resistant. As previously described, when gold becomes too thin, oxides can penetrate right through the relatively porous gold surface. Referring once again to FIGS. 11 through 20 herein, there are also taken from FIGS. 14 through 22 of U.S. Pat. No. 6,765,779 (i.e., '779 patent), the contents of which are also incorporated herein fully by reference. The '779 patent includes extensive detail on undesirable formation of titanium oxides and a capacitor's equivalent series resistance, including a description of both dielectric loss tangent and ohmic losses.

FIGS. 21 and 22 herein are taken from FIGS. 23 and 24 of the '779 patent. FIG. 21 illustrates that the electrical connection material 152 contacts between, in this case, a round quad polar capacitor's ground metallization 142 and the gold braze area of the hermetic seal 165. This is best understood by referring to section 22-22 from FIG. 21, which is illustrated in FIG. 22. Referring to FIG. 22, one can clearly see that the electrical connection material 152, which can be of thermal-setting conductive adhesive or a solder or the like, makes a low resistance/impedance (free of titanium oxides) connection between the capacitor ground metallization 142 and at least a substantial portion of the gold braze pad area 165, which also forms the hermetic seal between the ferrule 112 and insulator 160. This forms an oxide-resistant low impedance and low resistance electrical connection that would be robust at high-frequencies so that the feedthrough capacitor 132 can properly divert unwanted high-frequency EMI energy. As defined herein, an EMI filter hermetically sealed assembly (i.e., filter feedthrough) for an active implantable medical device, will be herein designated as assembly 210. The '779 patent has enjoyed great commercial success and has proven to be highly reliable. Manufacturing processes of the '779 patent does require tight dimensional tolerances between the ferrule inside diameter and the alumina insulator outside diameter or perimeter. In addition, the oxide-resistant pads as described in the '779 patent require a significant amount of extra gold to be used in the process which is thereby increasingly expensive.

FIG. 22A is taken from section 22A-22A from FIG. 21 and illustrates what happens to the gold braze 165 during high-temperature gold braze furnace reflow operations. Due to gravity, since there is nothing to physically constrain the gold, when molten or liquid, it has a tendency to flow down in the area 165', as illustrated. This leaves behind a much smaller area of gold 165T for electrical attachment 152' to the feedthrough capacitor ground metallization 142. Referring once again to FIGS. 22 and 22A, a step ST has been added in the ferrule in an attempt to slow down and prevent the flow of the gold braze material 165T. This is somewhat effective but requires that a great deal more gold 165 must be used before this column is filled up, such that a suitable electrical connection 162' can be accomplished between the feedthrough capacitor ground metallization 142 and the gold braze surface 165T.

FIG. 23 is an electrical schematic taken from FIGS. 20 through 22A wherein the $R_{oxide}$ is no longer present.

FIG. 24 illustrates filter performance otherwise known as attenuation or insertion loss curves vs frequency. An ideal feedthrough capacitor C, 132 attenuation curve is shown. One can see that it has a slight self-resonance above 1 GHZ and then continues to function. Accordingly, it becomes a broadband 3-terminal filter as previously described. As can be seen, the ideal feedthrough capacitor has over 30 dB of attenuation at all frequencies above 450 MHz. This frequency range is important because that's the range at which cell phones operate. Cell phones are of particular concern to active implantable medical devices because they are small and can be brought into very close proximity to a medical implant. For example, one concern is for a pacemaker patient where the cell phone may be placed in a shirt pocket directly over the implant. This would couple maximum energy to implanted leads. Referring once again to the insertion loss attenuation curves of FIG. 24, one can see what happens when the feedthrough capacitor has undesirable resistive oxide $R_{oxide}$ in its ground electrical path. The oxide degrades the attenuation or filter performance such that you end up with a curve, which provides less than 30 dB of attenuation at frequencies above 450 MHz. This seriously degraded filter performance is of great concern because if a closely held emitter, such as a cellular telephone, interferes with, for example, a pacemaker sense circuit, it can undesirably cause the pacemaker to inhibit. Inhibit means that it would fail to provide life-saving therapeutic pulses. One might ask, why are pacemakers designed to inhibit? Well, there are two reasons: Many patients who suffer from bradycardia (a very low heart rate) are not bradycardic all-day long. In other words, they can come in and out of bradycardic (life-threatening) condition. Therefore, demand pacemakers were developed such that when a patient's normal sinus rhythm returns, the pacemaker will inhibit. This is to not only save battery life, but also prevents a condition called rate competition. This is where you wouldn't want the pacemaker to provide a pulse that is out of sync or competitive with a patient's intrinsic rhythm. However, this does lead to electromagnetic interference danger. If EMI is undesirably detected as a normal cardiac pulse, it can cause the device to inhibit, which is immediately life-threatening for a pacemaker dependent patient. The attenuation versus frequency for a flat-thru capacitor is also shown, including frequencies above 3 GHz where the flat-thru capacitor attenuation declines.

Active implantable medical devices, in general, have a hermetically sealed feedthrough. This is necessary because, in general, the AIMDs have a completely enclosed and usually metallic housing. Leadwires that stimulate body tissue must pass through the conductive housing in nonconductive relationship so that they do not short out. This is where the hermetic seal is important, such that body fluids cannot enter into the conductive housing and damage sensitive electronic circuits. Damage can happen due to corrosion, formation of dendrites, or the like. Over the last years, feedthroughs for AIMDs have been increasing channel counts. What this means is, for example, with cardiac pacemakers, these use to be unipolar, single wired devices that paced only the right ventricle. Modern pacemakers, such as CRT-P pacemakers may have 12 or more leads. Even more dramatically, in the neurostimulator field, spinal cord stimulators have evolved from 8 channels to 32 channels and even more. For retinal stimulators, initial devices only had 8 channels (8 pixels) to create an image for a blind person. However, prototypes and devices on the drawing board, now have hundreds, if not thousands of channels. In the past, when the channel count was low, electrical connections were relatively easy to make and could be done by using discrete connections, such as BGA dots, solder connections or syringe-dispensed conductive adhesives. However, when channel counts get very high and channels are very close together, such former connection concepts become unworkable. Accordingly, there is a need for making an electrical connection for active implantable medical devices where the pitch (the spacing between adjacent conductors) is small, and the channel count (the number of feedthrough conductors) is very high. There is another trend and that is the elimination of feedthrough wires through the hermetically sealed feedthroughs for AIMDs. The reason for this is that feedthrough wires are generally installed in alumina type insulators and are gold brazed to form both a mechanical and a hermetic seal. The problem with these prior art techniques, even though they were very successful and very biocompatible, is that they use up a lot of space. In other words, they are large in diameter. When the channel counts are very, very high, it is simply not possible to have a leadwire, an associated gold braze and the sputter layers. Increasingly, using sintered vias, instead of those with a gold braze leadwire, are becoming more popular. These co-sintered vias, for example, as described by U.S. Patent Application Pub. No. 2018/0197661, the contents of which are incorporated herein fully by reference. By definition, hermetic seals for AIMDs pass from a body fluid side to a device side. The body fluid side is the device oriented towards the leadwires, which pass through body tissues and either deliver therapy pulses or sense biological signals. On the device side, the hermetic seal conductive pathway is connected to AIMD internal circuitry, including power sources. The present invention will address novel uses of anisotropic conductive layers to make connections to hermetic seals for active implantable medical devices, both on the device side and on the body fluid side. For the body fluid side application, as will be described, the anisotropic conductive layers must be biocompatible, non-toxic, and biostable.

SUMMARY OF THE INVENTION

An exemplary embodiment of the present invention is a filter feedthrough (210) for an active implantable medical device (AIMD, 100). An electrically conductive ferrule (112) is configured to hermetically seal an opening (115) of a housing (116) of the AIMD (100). The ferrule is configured to separate a body fluid side opposite a device side. The ferrule includes a ferrule opening (113) extending between and to the body fluid side and the device side. When the ferrule is attached to the opening of the housing of the AIMD, the body fluid side resides outside the AIMD housing and device side resides inside the AIMD housing. An insulator (160) hermetically seals the ferrule opening. The insulator is configured to separate the body fluid side and the device side. A first conductive pathway (114, 117, 185, 186, 186W) is hermetically sealed to and disposed through the insulator between the body fluid side and the device side, the first conductive pathway being in non-electrically conductive relation with the ferrule. A feedthrough capacitor (132) is disposed on the device side, the feedthrough capacitor comprises: at least one active electrode plate (148) disposed parallel and spaced from at least one ground electrode plate (146), wherein the at least one active and ground electrode plates are disposed within a capacitor dielectric (147, 149); a capacitor active metallization (144) electrically connected to the at least one active electrode plate and in non-electrically conductive relation with the at least one ground electrode plate; and a capacitor ground metallization (142) electrically connected to the at least one ground electrode plate and in non-electrically conductive relation with the at least one active electrode plate. An anisotropic conductive layer (212') is disposed on the device side, where the anisotropic conductive layer is electrically connecting the capacitor active metallization to the first conductive pathway.

In other variations of the exemplary embodiment, the anisotropic conductive layer (212') may comprise a plurality of electrically conductive particles (262, 262') disposed within an electrically insulative matrix (213).

The anisotropic conductive layer may comprise at least one conductive location, wherein the at least one conductive location may comprise at least one electrically connected particle (262') of the plurality of electrically conductive particles, the at least one electrically connected particle physically abutted on both a first end (263a) opposite a second end (263b), wherein the first end may be electrically connected to the capacitor active metallization and the second end may be electrically connected to the first conductive pathway. In at least another embodiment, the ACL includes the at least one electrically conductive particle and the conductive location.

The anisotropic conductive layer may comprise at least one nonconductive location, wherein the at least one nonconductive location comprises at least one electrically insulated particle (262) of the plurality of electrically conductive particles, the at least one electrically insulated particle in electrical non-conductive relation with the at least one electrically connected particle. In at least another embodiment, the ACL includes the at least one nonconductive location.

The at least one conductive location may include at least one conductive protrusion abutting and electrically connected to the at least one electrically connected particle. In at least another embodiment, the ACL includes the at least one conductive protrusion.

The anisotropic conductive layer may be selected from the group consisting of a film, a paste, a tape, and an adhesive.

The plurality of electrically conductive particles may be selected from the group consisting of metallic particles, metal-coated particles, electrically conductive composite particles and electrically conductive coated polymer, glass, glass-ceramic, or ceramic particles.

The first conductive pathway may comprise a leadwire (114), wherein the at least one conductive protrusion is an extended end of the leadwire or a nail head end (114NH) of the leadwire. The leadwire (114) may comprise two different materials (114 and 117) electrically connected.

The anisotropic conductive layer may be at least partially disposed between the insulator and the feedthrough capacitor, wherein the feedthrough capacitor may comprise a leadwire (111) disposed on the device side electrically connected to the capacitor active metallization, wherein the at least one conductive protrusion may be an extended end of the leadwire or a nail head end (111NH) of the leadwire.

The ferrule may include at least one surface (113) disposed on the device side with at least one pocket (248) formed in the at least one surface, and a gold pocket pad (250) may be disposed within the at least one pocket.

The capacitor ground metallization may be disposed on an exterior surface of the feedthrough capacitor and including an electrical connection material (152) electrically connecting the capacitor ground metallization to the gold pocket pad disposed within the at least one pocket.

The insulator may be alumina and hermetically seal the ferrule opening by a first gold braze (150), wherein the first gold braze and the gold pocket pad are not physically touching one another.

The insulator may be glass and hermetically seal the ferrule opening by a first glass seal.

The insulator may be alumina and hermetically seals the ferrule opening by a first gold braze (150), wherein the capacitor ground metallization may be disposed on an exterior surface of the feedthrough capacitor and including an electrical connection material (152) electrically connecting the capacitor ground metallization to the first gold braze.

At least a first edge (252) of the feedthrough capacitor may extend beyond a first outermost edge (256) of the ferrule, and wherein at least a second edge (254) of the feedthrough capacitor may not extend beyond a second outermost edge (258) of the ferrule.

The capacitor dielectric may have a k value greater than zero and up to 200, or a k value greater than 200 and up to 1000.

The capacitor ground metallization may not be disposed on an exterior surface of the feedthrough capacitor and may be disposed within a ground via hole in the feedthrough capacitor, wherein the ferrule may include a peninsula (139) or a bridge (141) extending into the ferrule opening, wherein a ground leadwire (111) may be electrically connected to the capacitor ground metallization, wherein the ground lead wire may be at least partially disposed within the ground via hole and electrically connected to the peninsula or the bridge.

The capacitor ground metallization may be at least partially disposed on an exterior surface of the feedthrough capacitor and is electrically connected to the ferrule, and a second capacitor ground metallization (142') may be electrically connected to the at least one ground electrode plate and may be disposed within a ground via hole in the feedthrough capacitor, wherein the ferrule may include a peninsula (139) or a bridge (141) extending into the ferrule opening, wherein a ground leadwire (111) may be at least partially disposed within the ground via hole and electrically connected to the second capacitor ground metallization, wherein the ground lead may be electrically connected to the peninsula or the bridge.

The capacitor ground metallization may be at least partially disposed on an exterior surface of the feedthrough capacitor and may be electrically connected to the gold pocket pad, and a second capacitor ground metallization (142') may be electrically connected to the at least one ground electrode plate and may be disposed within a ground via hole in the feedthrough capacitor, wherein the ferrule may include a peninsula (139) or a bridge (141) extending into the ferrule opening, wherein a ground leadwire (111) may be at least partially disposed within the ground via hole and electrically connected to the second capacitor ground metallization, wherein the ground lead may be electrically connected to the peninsula or the bridge.

A metal addition (251) may be electrically connected to the gold pocket pad, wherein the metal addition is a different material in comparison to the ferrule, and wherein at least a portion of the metal addition is disposed above the at least one surface (113) of the ferrule, wherein the anisotropic conductive layer electrically connects the capacitor ground metallization to the metal addition.

The insulator may comprise alumina ceramic, wherein the first conductive pathway may comprise a composite fill co-sintered with the alumina ceramic or a substantially pure platinum fill co-sintered with the alumina ceramic, the fill extending from the body fluid side to the device side, wherein the first fill end is disposed at or adjacent to the device side of the insulator body, and wherein the second fill end is disposed at or adjacent to the body fluid side of the insulator body, wherein the composite fill comprises a ceramic reinforced metal composite comprising alumina and platinum and a substantially pure platinum fill or a metallic wire. A metallic end cap may be co-sintered into the composite fill, wherein at least a portion of the metallic end cap extends beyond a device side surface of the insulator and is electrically connected to the capacitor active metallization by the anisotropic conductive layer.

Thus, the present invention relates to a filtered feedthrough that is attachable to an active implantable medical device (AIMD), the filtered feedthrough comprising: a ferrule configured to be installed in an opening of a housing of the AIMD, the ferrule comprising a ferrule opening extending to a ferrule body fluid side opposite a ferrule device side, wherein, when the ferrule is installed in the opening of the AIMD housing, the ferrule body fluid side and the ferrule device side reside outside the housing and inside the housing, respectively; and an insulator hermetically sealed in the ferrule opening, the insulator having at least one via hole extending therethrough to an insulator body fluid side and an insulator device side; an insulator conductive pathway disposed through and hermetically sealed to the insulator in the at least one via hole, wherein the insulator conductive pathway comprises an insulator conductive pathway body fluid side end disposed adjacent to the insulator body fluid side and an insulator conductive pathway device side end disposed adjacent to the insulator device side; a filter capacitor disposed on the ferrule device side, the filter capacitor comprising: a dielectric substrate supporting at least one active electrode plate interleaved in a capacitive relationship with at least one ground electrode plate, wherein the dielectric substrate extends to a dielectric substrate device side opposite a dielectric substrate body fluid side; a first passageway disposed through the dielectric substrate; a capacitor active conductive pathway extending through the first passageway in the dielectric substrate and being electrically connected to the at least one active electrode plate, wherein a capacitor active conductive pathway device side end resides adjacent to the dielectric substrate devise side and a capacitor active conductive pathway body fluid side end resides adjacent to the dielectric substrate body fluid side; and a capacitor ground metallization disposed on an outer surface of the capacitor dielectric substrate and being electrically connected to the at least one ground electrode plate, an anisotropic conductive layer disposed between the capacitor dielectric substrate body fluid side and the insulator device side and comprising an electrically insulative matrix supporting a plurality of electrically conductive particles, wherein the anisotropic conductive layer comprises: a first thickness that is longitudinally aligned with the capacitor active conductive pathway body fluid side end and the insulator conductive pathway device side end; and a second, greater thickness where the capacitor active conductive pathway body fluid side end and the insulator conductive pathway device side end are not longitudinally aligned, wherein the first thickness provides at least one longitudinally aligned electrically conductive particle being in contact with the capacitor active conductive pathway body fluid side end and the insulator conductive pathway device side end to thereby provide electrical continuity from the capacitor active conductive pathway device side end to the insulator conductive pathway body fluid side end; and a first electrically conductive material electrically connecting the capacitor ground metallization to the ferrule.

In one embodiment of the present invention, at least one of the capacitor active conductive pathway body fluid side end and the insulator conductive pathway device side end is proud of the respective capacitor dielectric substrate body fluid side and the insulator device side, and wherein the first thickness of the anisotropic conductive layer is longitudinally aligned with the at least one proud capacitor active conductive pathway body fluid side end and the insulator conductive pathway device side end, and wherein the second, greater thickness resides where the at least one proud capacitor active conductive pathway body fluid side end and the insulator conductive pathway device side end are not longitudinally aligned.

BRIEF DESCRIPTION OF THE DRAWINGS

The accompanying drawings illustrate the invention. In such drawings:

FIG. 3A is an exploded isometric view of the unipolar capacitor of FIG. 3;

FIG. 11 is an isometric view illustrating a prior art rectangular feedthrough capacitor, which has the same number of poles (4, quadpolar) as previously illustrated in FIG. 10A;

FIG. 12 is an isometric view illustrating the hermetic seal subassembly ready to receive the capacitor of FIG. 11;

FIG. 13 is taken generally from section 13-13 from FIG. 11 showing the active electrode plates;

FIG. 14 is taken generally from section 14-14 from FIG. 11 showing the ground electrode plate;

FIG. 32A is an isometric view illustrating an internally grounded feedthrough capacitor exploded away and ready for installation on internally grounded hermetic seal assembly;

FIG. 32B is similar to FIG. 32A now showing the electrode plate structure of the capacitor;

FIG. 32C is similar to FIG. 32A now showing the capacitor mounted;

FIG. 39 is an isometric view similar to FIG. 36, except that the ground pin is part of a ferrule peninsula;

FIG. 42 illustrates an isometric view of a prior art chip capacitor also known as a multilayer ceramic capacitor or MLCC;

FIG. 43 is a side sectional view taken from section 43-43 from FIG. 42;

FIG. 44 is taken from section 44-44 from FIG. 43;

FIG. 45 is taken from section 45-45 from FIG. 43;

FIG. 48 is a side sectional view similar to FIG. 47 now showing the use of a conductive metallic insert used to compress the conductive spheres of the anisotropic conductive layer;

FIG. 48A is an enlarged sectional view taken along lines 48A-48A of FIG. 48;

DETAILED DESCRIPTION OF THE PREFERRED EMBODIMENTS

Figure 18:
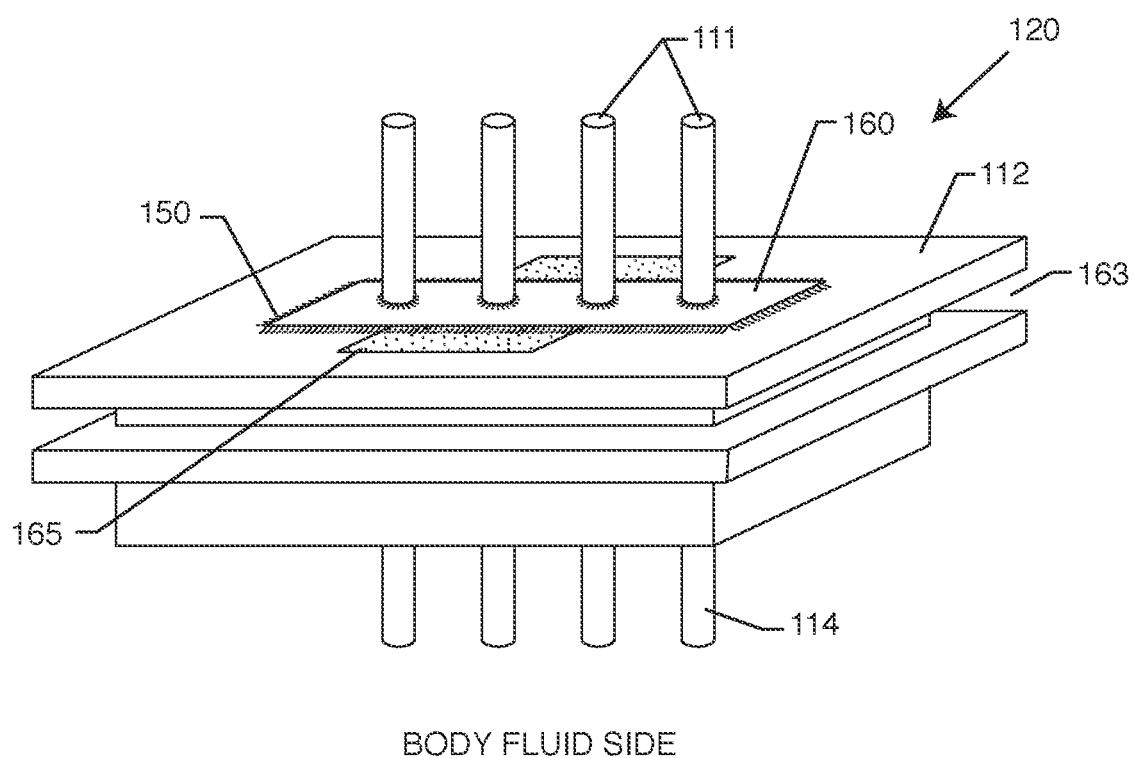
FIG. 18 is an isometric view showing the use of gold braze bond pads that are one embodiment of a novel feature of the '596 patent.
Figure 19:
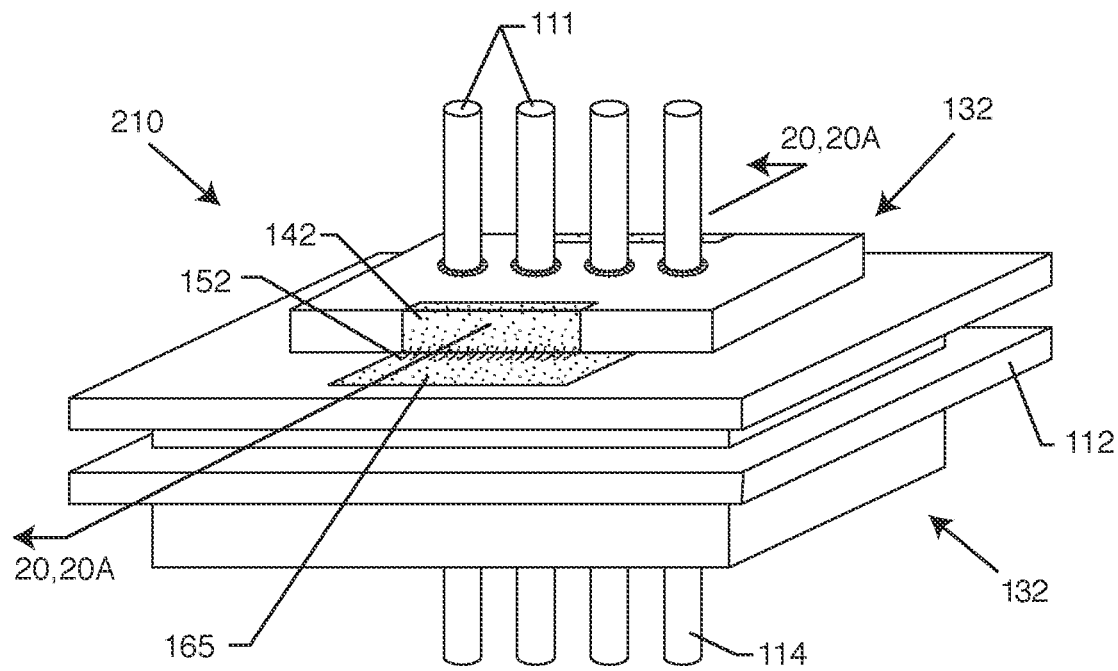
FIG. 19 is an isometric view with a feedthrough capacitor installed and now showing that the feedthrough capacitor ground metallization is electrically attached by a thermal-setting conductive adhesive directly to the gold bond pad area.
Figure 20:
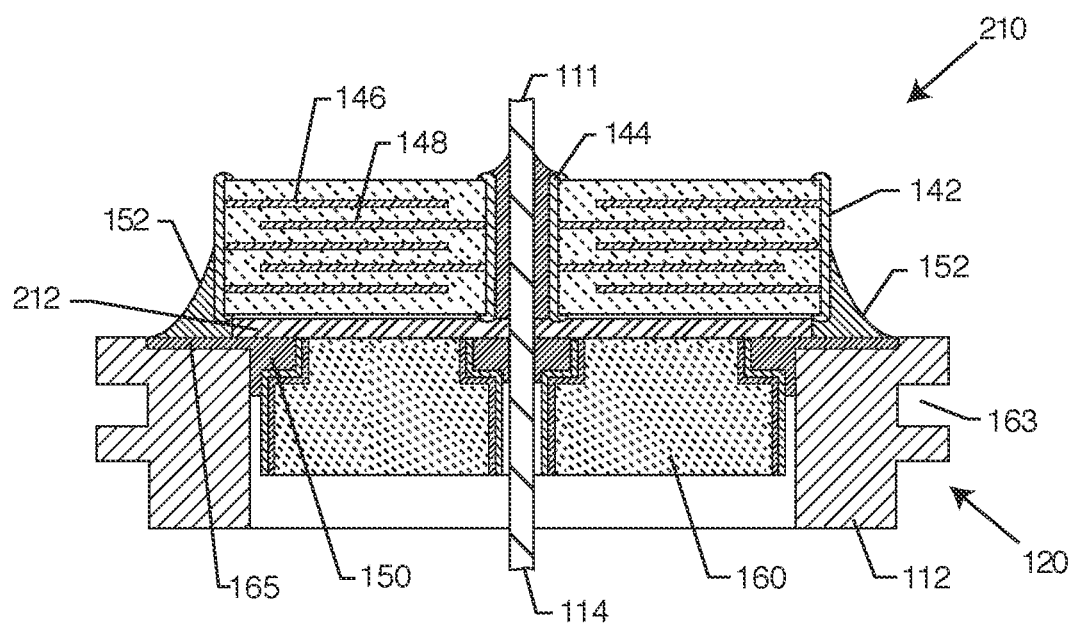
FIG. 20 is a side sectional view taken from section 20-20 from FIG. 19.
Figure 20A:
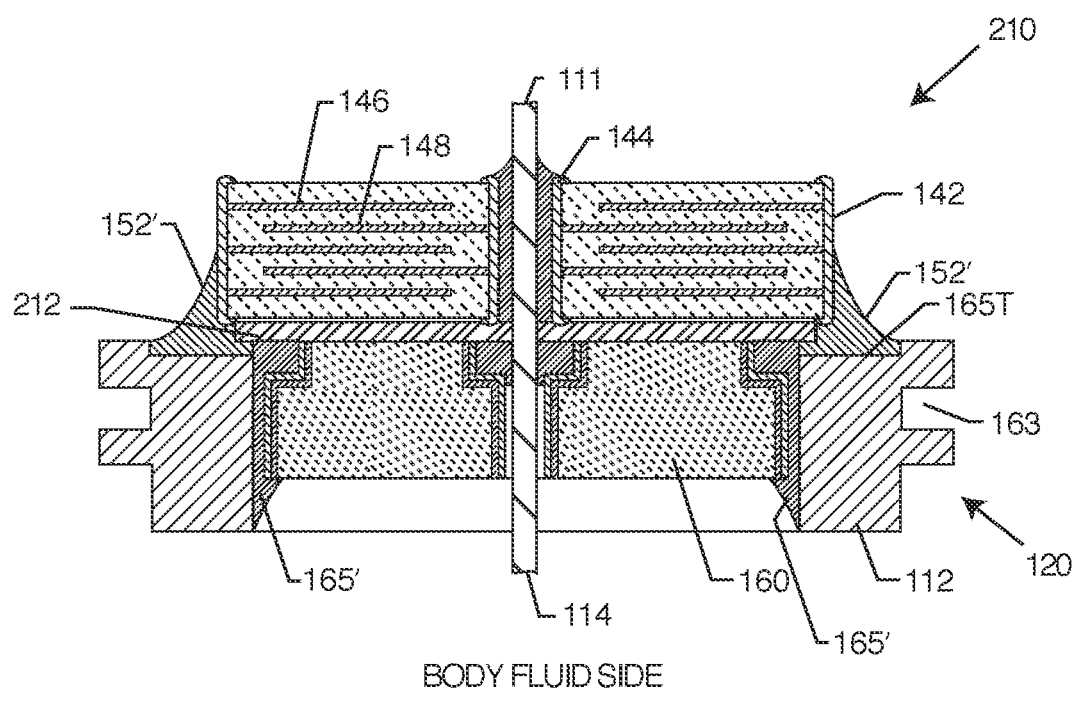
FIG. 20A is another side sectional view taken from section 20A-20A from FIG. 19 and now shows a more realistic structure of what happens to the gold braze of the gold bond pad area.
Figure 21:
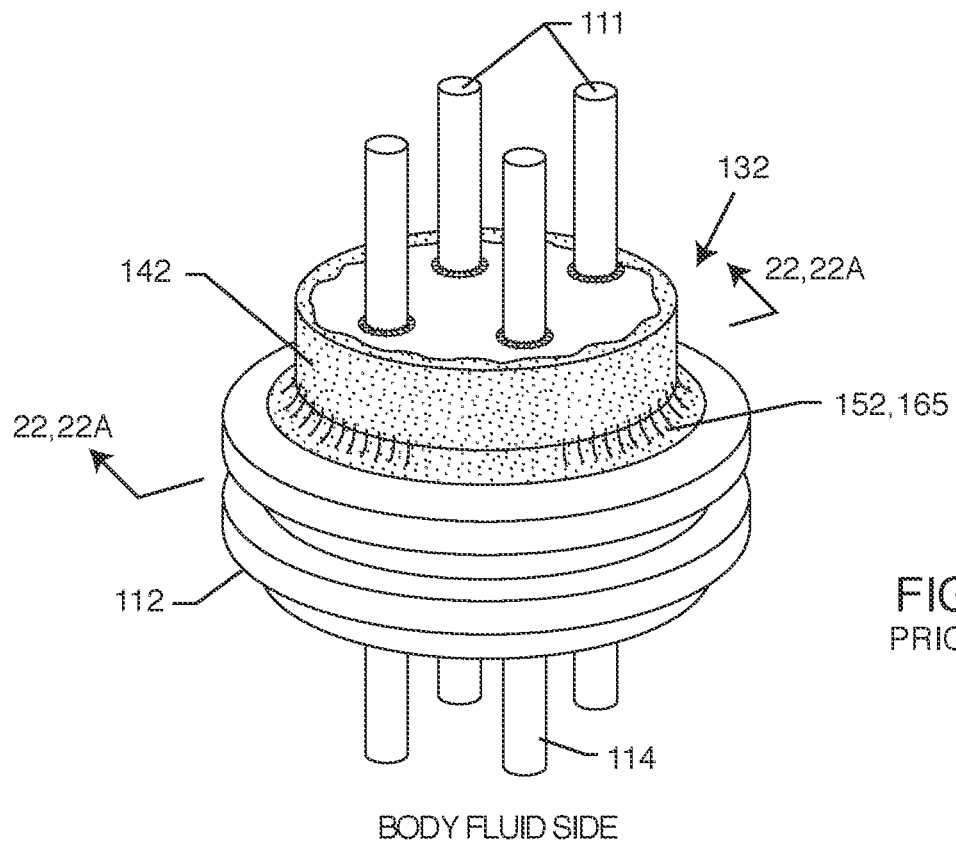
FIG. 21 is an isometric view taken from FIG. 23 of the '779 patent.
Figure 22:
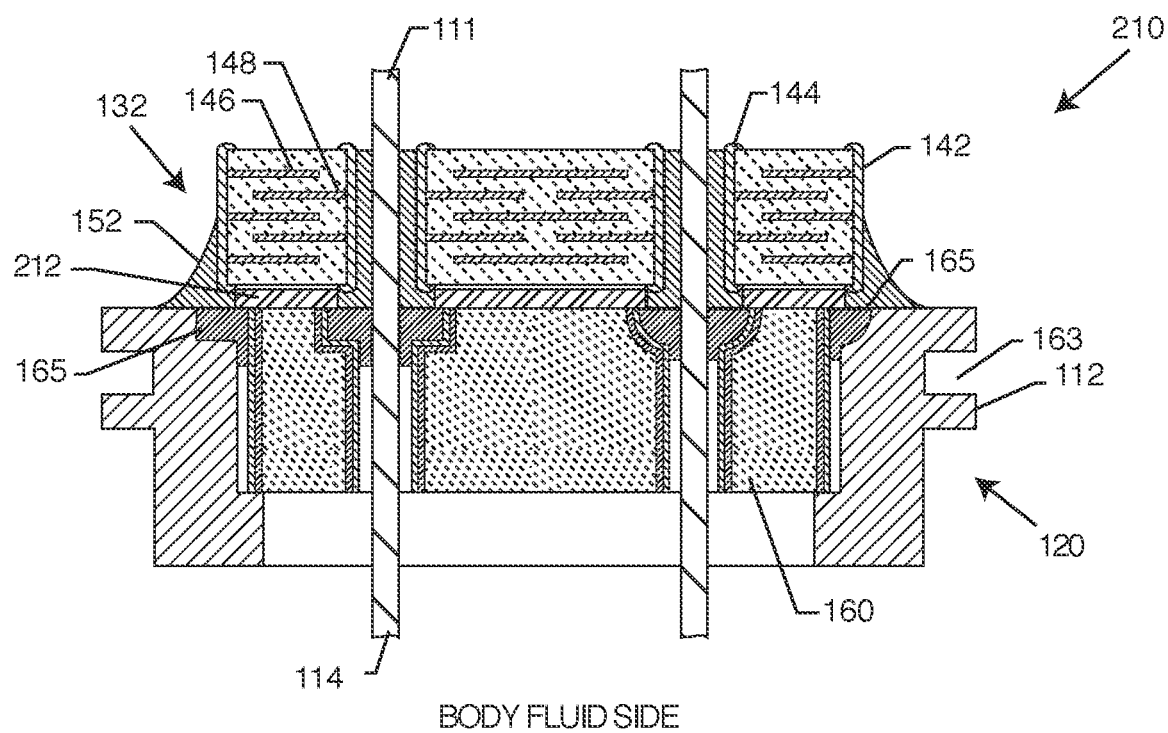
FIG. 22 is a side sectional view of the structure of FIG. 21 taken along lines 22-22.
Figure 22A:
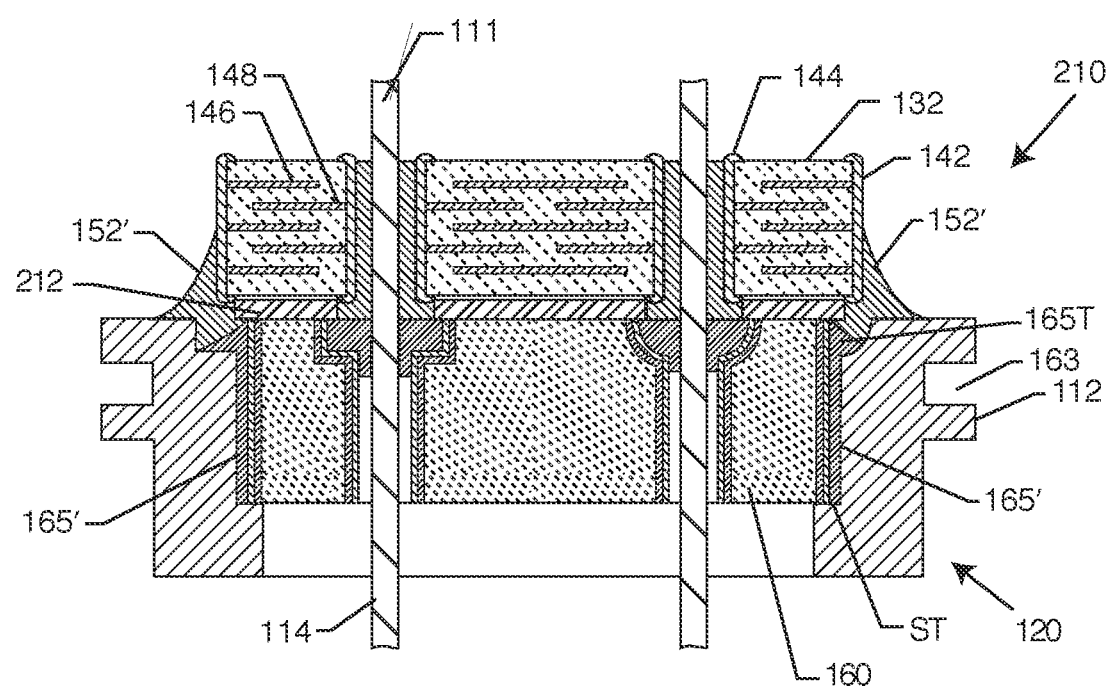
FIG. 22A is another side sectional view taken from section 22A-22A from FIG. 21 which is similar to FIG. 22, but now illustrates what really happens to the gold braze during high-temperature gold braze furnace reflow operations.
Figure 23:
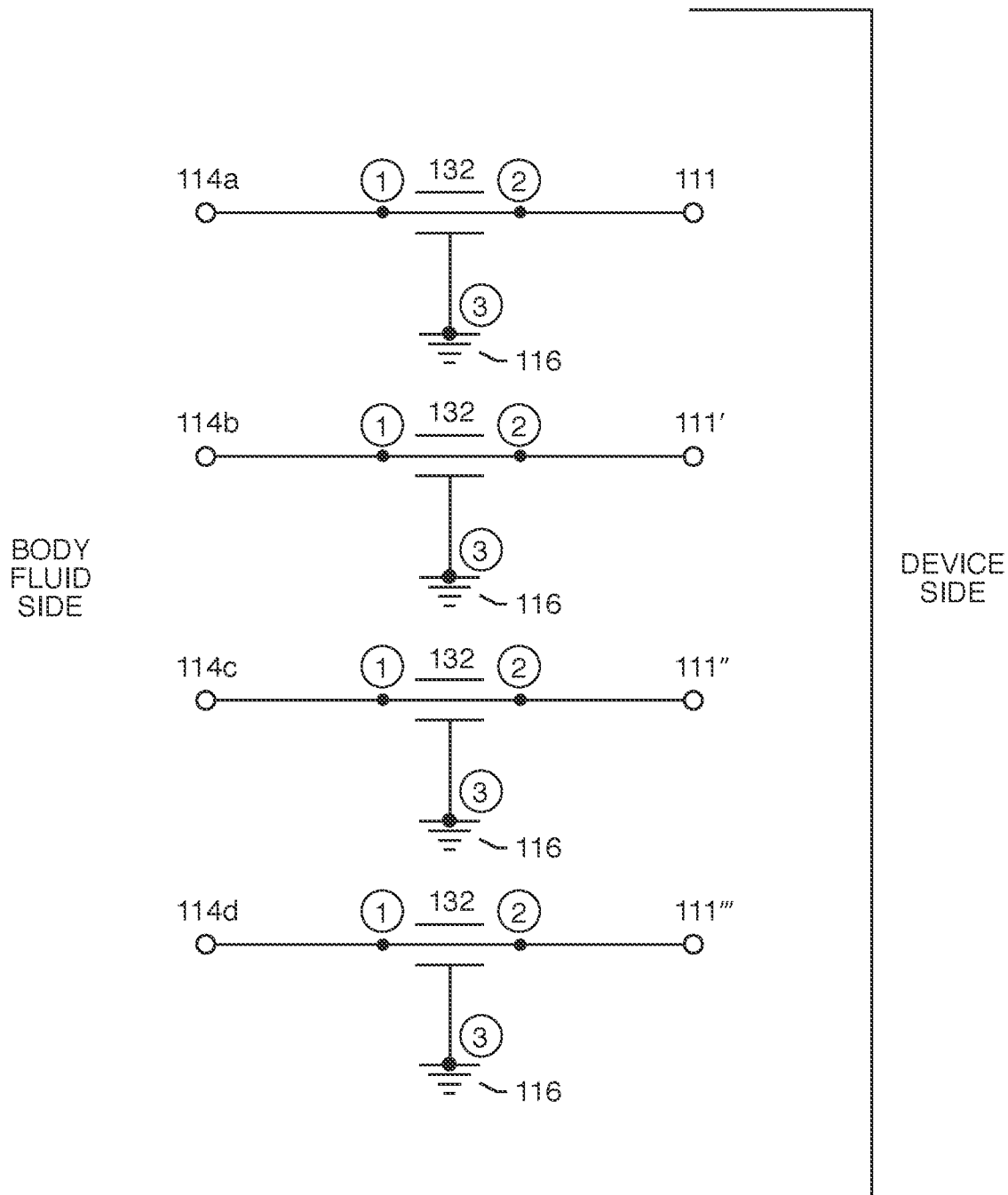
FIG. 23 is an electrical schematic taken from FIGS. 20 through 22A.
Figure 24:
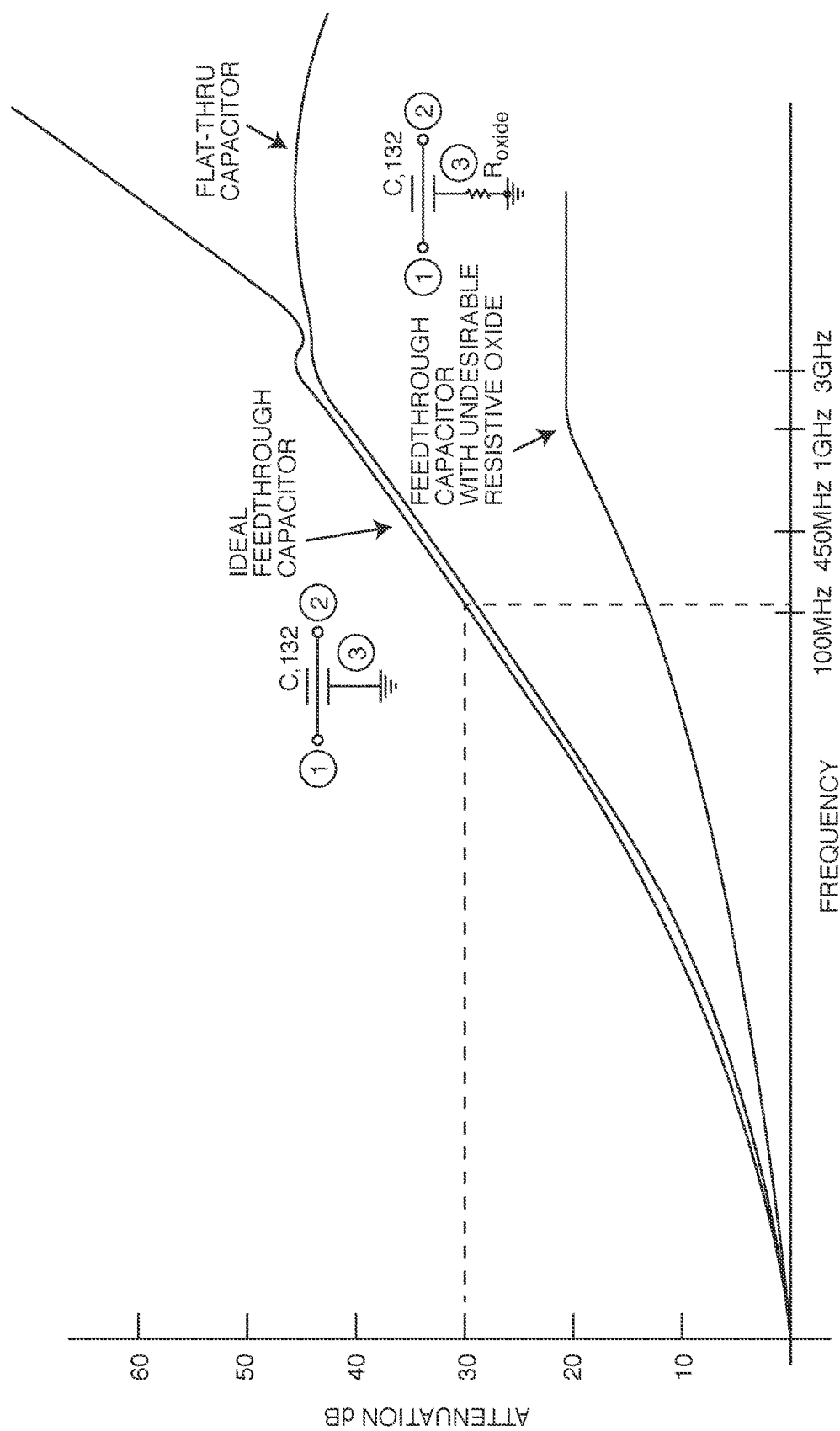
FIG. 24 is a graph illustrating filter performance otherwise known as attenuation or insertion loss curves versus frequency.
Figure 25A:
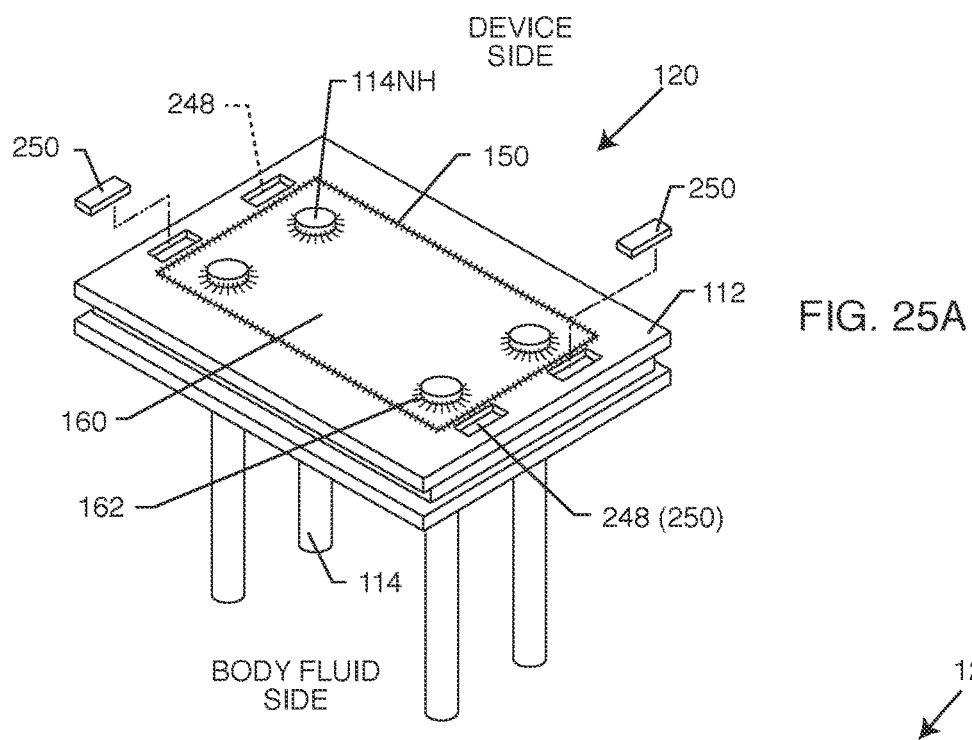
FIG. 25A is similar to FIG. 48 of the '596 patent but now shows only a gold braze disposed with the ferrule pocket and the leadwire has a nail head structure.

FIG. 25A is similar to FIG. 18 in that, provision has been made to attach the capacitor ground metallization to non-oxidized structures on the surface of the ferrule 112. In the case of FIG. 25A, these are called gold pocket pads. The pocket is formed by machining or by forming the ferrule such that it has a swimming pool-type pocket 248. A gold braze preform 250 is brazed at the same time the other brazes 150 and 162 are formed. The gold braze 150 of the hermetic seal, between the insulator 160 and the ferrule 112 is discontinuous from the gold braze 250 that may fill the gold pocket pad 248. A number of other oxide resistant materials other than gold can be used. Gold pocket pads are more thoroughly described in U.S. Patent Application Pub. No. 2018/0236244, the contents of which are incorporated herein fully by reference.

Figure 25B:
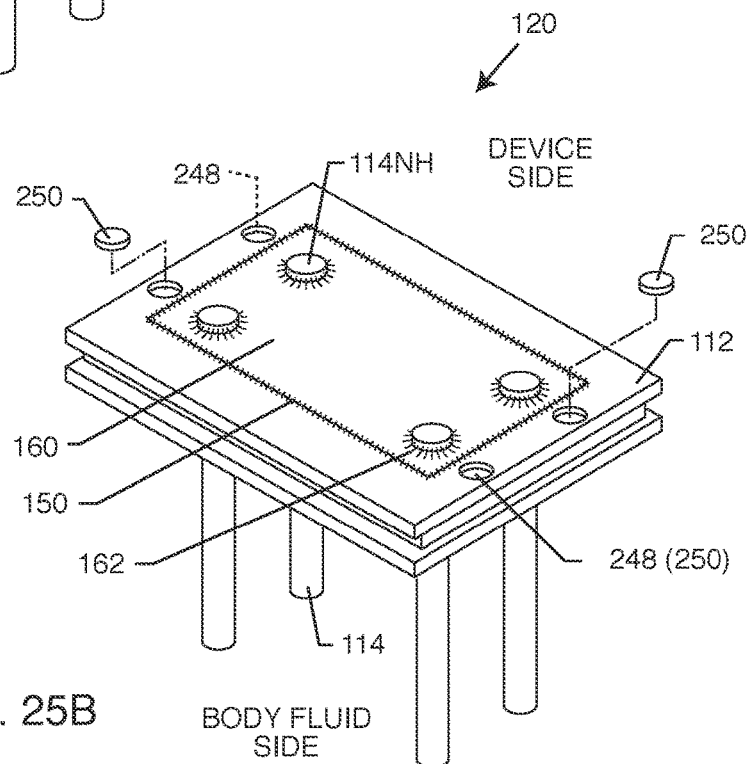
FIG. 25B is similar to FIG. 49 of the '596 patent but now shows only a gold braze disposed with the ferrule pocket and the leadwire has a nail head.

FIG. 25B is very similar to FIG. 25A, except that instead of being rectangular, the gold pockets and pocket pads are round.

Figure 26:
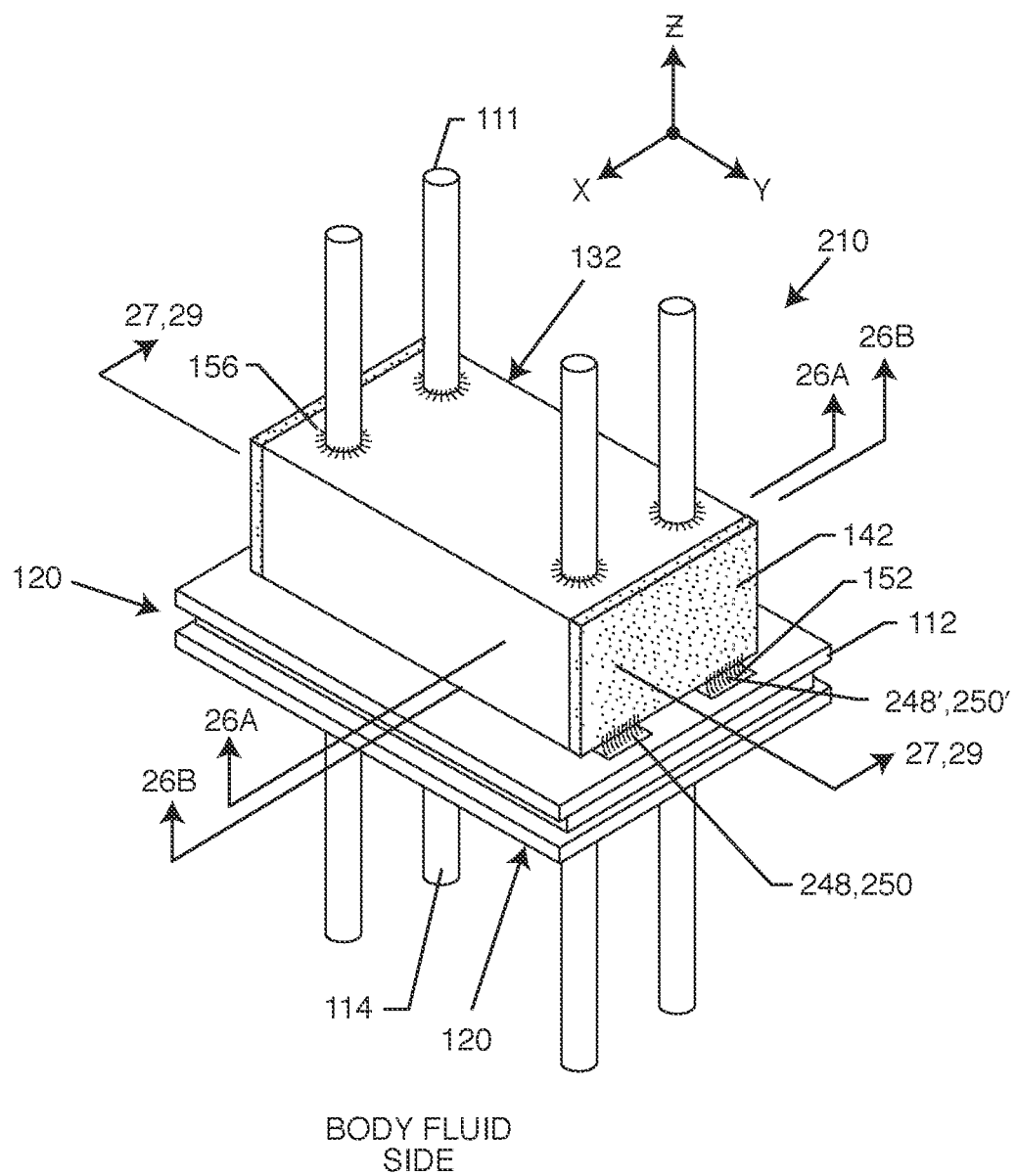
FIG. 26 is similar to FIG. 50 of the '596 patent but now shows how the feedthrough capacitor makes an electrical connection utilizing the anisotropic conductive layers of the present invention.

FIG. 26 illustrates placement of a rectangular quad polar feedthrough capacitor 132 onto the hermetic terminal subassembly previously illustrated in FIG. 25A. As will be seen, leadwires 111-114 are discontinuous, as will be illustrated in FIG. 27. The quad polar feedthrough capacitor 132 has ground metallizations 142 on each end. The ground metallization is electrically connected 152 with a solder or a thermal-setting conductive adhesive to the oxide resistant pocket pad 250, which is preferably of gold, for example.

Figure 26A:
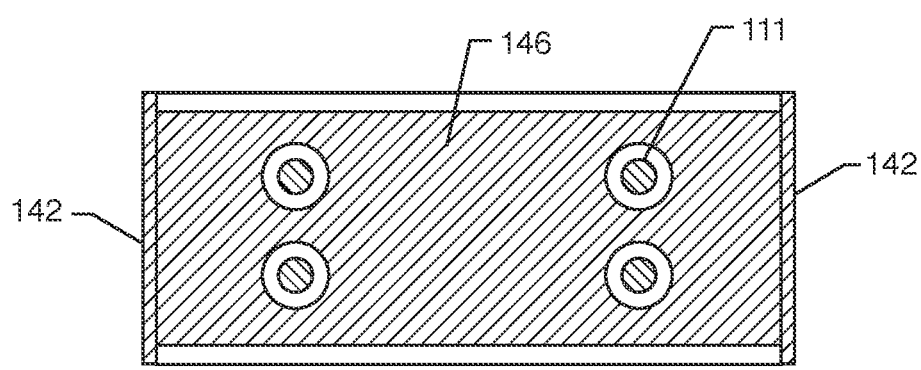
FIG. 26A is taken generally from section 26A-26A from FIG. 26 and illustrates the ground electrode plates of feedthrough capacitor.

FIG. 26A is taken from section 26A-26A from FIG. 26 and illustrates the ground electrode plates 146 of the quad polar capacitor 132.

Figure 26B:
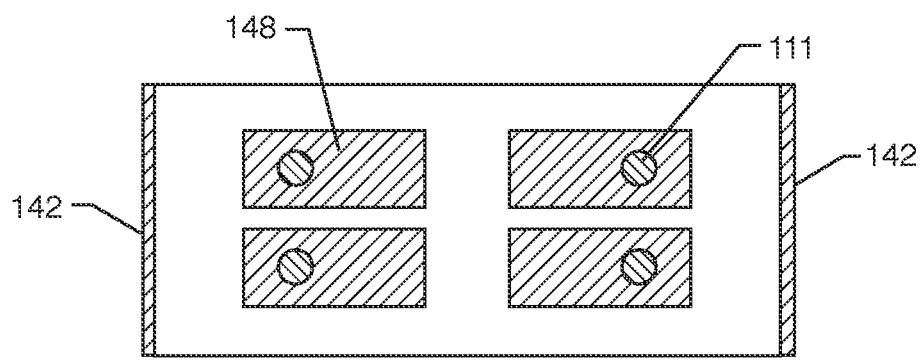
FIG. 26B is taken generally from section 26B-26B from FIG. 26 and illustrates the feedthrough capacitor's four active areas.

FIG. 26B is taken from section 26B-26B from FIG. 26 and illustrates the four active electrodes 148. It is the overlap of the active electrodes over the ground electrodes that determines the capacitance value.

Figure 27:
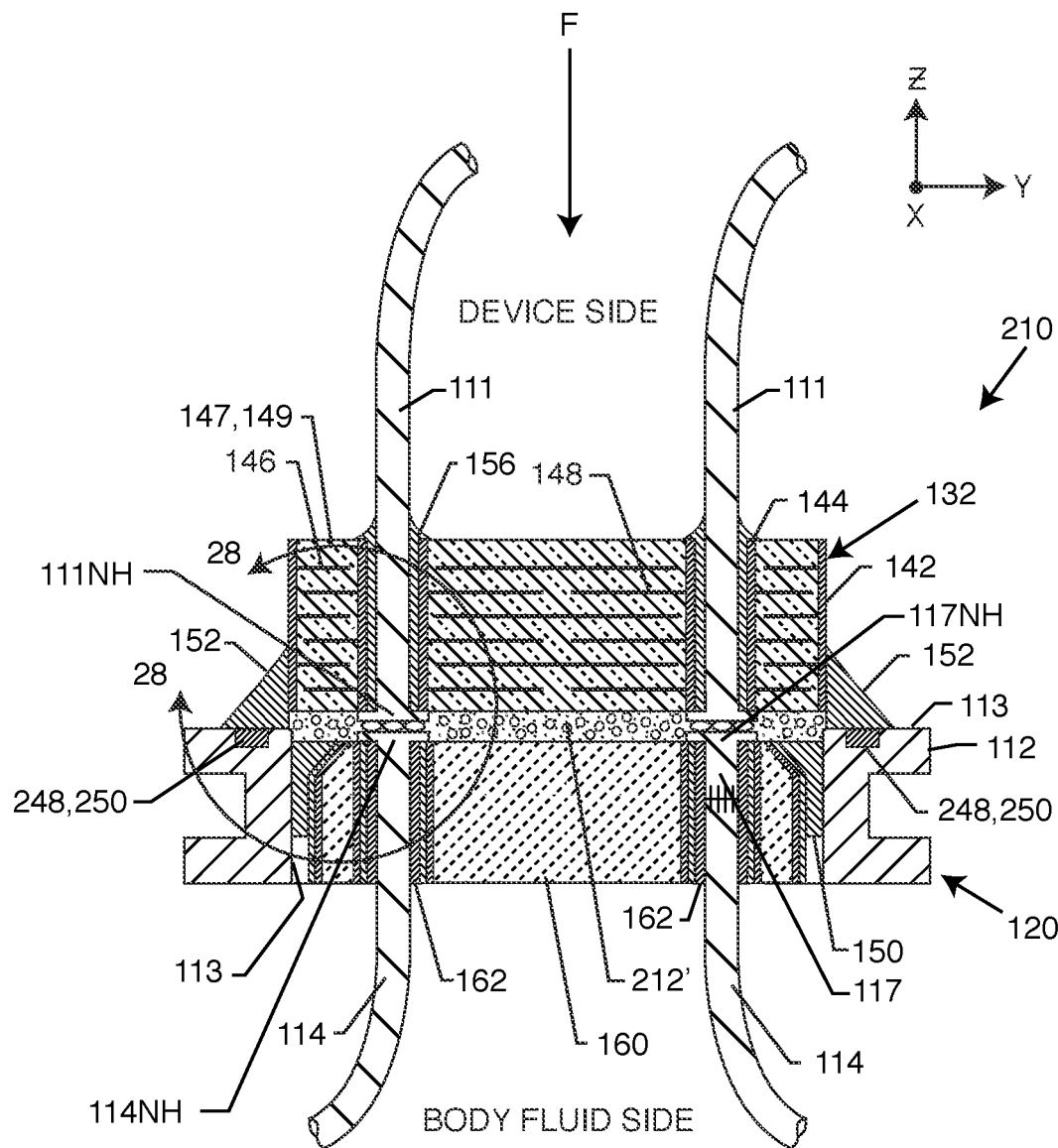
FIG. 27 is a side sectional view taken generally from section 27-27 from FIG. 26 and illustrates the feedthrough capacitor with gold pocket pad attachments shown in cross-section.

FIG. 27 is taken from section 27-27 from FIG. 26. FIG. 27 illustrates the quad polar feedthrough capacitor in cross-section disposed on the hermetic seal subassembly 120. In this case, the leadwire 111, 114 is discontinuous. Referring back to FIG. 25A, one can see on the body fluid side of the hermetic seal, the leadwire 114 terminates in a nail head structure 114NH that sits above the surface of the hermetic seal insulator 160. The feedthrough capacitor subassembly 132 of FIG. 27 includes leadwire 111 and its integral nail head 111NH, as indicated. In general, the feedthrough capacitor is made in a completely different manufacturing process area than the hermetic terminal subassembly 120. In a separate manufacturing operation, the feedthrough capacitor 132 is attached to the hermetic seal subassembly 120. Before this attachment is made, the leadwires 111, 111NH are first mechanically and electrically attached to the feedthrough capacitor passageway metallization 144. This is done with a solder or thermal-setting conductive adhesive 156, as indicated.

In accordance with the present invention, an anisotropic conductive layer (ACL) 212' is disposed between the device side of the hermetic seal insulator 120 and the bottom of the feedthrough capacitor subassembly 132. As taught herein for any of the embodiments disclosed, it will be understood by those skilled in the art that the anisotropic conductive layer could be a film, paste, tape, adhesive, epoxy or the like that has an electrically insulative matrix 213 with a plurality of conductive particles 262 disposed therein, the conductive particles also generally in non-conductive relation to one another. Accordingly, throughout this application the anisotropic conductive layer can and will be referred to as an anisotropic conductive adhesive (ACA) or an anisotropic conductive film (ACF).

In more detail, anisotropic conductive adhesives (ACA) may comprise films, pastes, tapes or epoxies. Anisotropic conductive films (ACF) or tapes may be supplied in reels wherein the film or tape only needs to be cut to a suitable size and placed between the feedthrough capacitor 132 and the hermetic seal subassembly 120. Anisotropic conductive pastes (ACP) or epoxies may be applied either by printing or by dispensing with a syringe. It is contemplated that the method of manufacture will align with the selected ACL type.

The conductive particles within the matrix may comprise metallic particles, metal-coated particles, electrically conductive composite particles, or electrically conductive coated polymer, glass, glass-ceramic, or ceramic particles. Conductive additives, fillers, particles, materials or components to the adhesive, matrix, epoxy or resin in order to obtain a degree of electrical conductivity by its addition may include metals, carbon particles, conductive fibers, platelets, flakes, tubes, foils, whiskers, or irregularly shaped conductive constituents. Metal coated particle core options include polymers, composites, meshes, screens, braids, foamed materials, custom fiber or wire forms, pressed powders, pressed material clumps, either as formed or infiltrated with either an elastomeric, semi-rigid or rigid material prior to coating. The conductive particles may be compressible, rigid or combinations thereof. Either the matrix for the particles, the conductive particles within the matrix, or both the matrix and the conductive particles there within may be homogeneous or heterogeneous, where the matrix may be of a single homogeneous material, a composite of more than one material, a thermoplastic-thermoset polymer composite, a composite of two materials having different softening and/or cure temperatures, or an epoxy resin. The matrix and/or resin materials may be designed to strengthen a joint, manage thermal expansion and/or shrinkage, tolerate assembly or tolerate operational, intermittent, or continuous, perturbations such as shock, vibration or temperature extremes. The conductive particle size within the matrix may be all the same or of different sizes, the average size having a distribution defined by application use. The conductive particle shape may be spherical, elliptical, elongated, rectangular, triangular, square, cubic, trapezoidal, tabular, irregular, dendritic, flake, platelet, fiber, tubular, angular, symmetric and/or asymmetric.

As used herein, the terms polymer, film, tape, resin, paste, matrix, epoxy, and resin are used interchangeably. Likewise, the terms additive(s), filler(s) and particle(s) are also used interchangeably. It will be appreciated by one of ordinary skill in the art that volume %>20 may be used for certain applications, for example, when custom formulations require specific particle size and/or shape distributions. In some cases, spacers may be added and/or applied to inhibit shorting. The word "matrix" as used herein means a material (substrate, carrier, medium, structure) in which something develops, as the electrically insulative matrix is subjected to heat and pressure to affect the electrical connections of the conductive particles disposed therein.

As used herein, the term "anisotropic" means that the adhesive matrix is electrically insulative in the X and Y axes while being electrically conductive at selected locations in the Z axis after heat and pressure is applied such that the conductive particles are selectively compressed. As defined herein the Z axis is generally defined as the longitudinal axis.

As shown in FIG. 27, when heating the feedthrough capacitor 132, the hermetic seal insulator 120 and the anisotropic conductive layer 212' there between, a force F is exerted against the feedthrough capacitor 132 which forces the leadwire nail heads 111NH of the leadwires 111 in the feedthrough capacitor 132 toward the leadwire nail heads 114NH of the leadwires 114 in the hermetic seal subassembly 120, thereby trapping the conductive particles within the space between the paired nail heads 111NH and 114NH. The applied force F compresses the heated anisotropic conductive layer 212' such that some of or a portion of the electrically insulative matrix flows from the space between the paired nail heads 111NH and 114NH leaving the conductive spheres there between to make an electrical connection between the leadwires 111, 114 of the feedthrough capacitor 132 and the hermetic seal subassembly 120. As the compression is only in the Z-axis direction, an electrical connection will be made in this direction only. Because anisotropic conductive layers have low conductive particle content, in areas where the conductive spheres have been not compressed, the spheres remain insulated by the adhesive/film/paste within which they reside and, therefore, do not conduct electricity.

Referring once again to FIG. 27, on the right side, shown is a two-part pin, wherein the leadwire 114 has a secondary leadwire portion 117. The two-part pin comprising the secondary leadwire portion 117 and the leadwire portion 114 are both captured by the gold braze 162. The nail head portion 117NH then makes contact with the conductive particles. To reduce cost, the materials 114 and 117 can be different as the material 117 can be of a lower cost as it does not have to be biocompatible or biostable. FIG. 27 shows the two-part pin welded thereon, which is optional.

Thus, this thermo-compression bonding comprises simultaneously applying heat and pressure to an assembly stack-up comprising an ACL disposed between at least two component surfaces. Heat and pressure are continuously applied until the embedded particles within the matrix (adhesive/film/paste matrix) sufficiently bridge, thereby electrically connecting two conductor surfaces, and is held at temperature and pressure until sufficient curing of the matrix achieves adhesion and/or curing. The electrical connection bridge is formed when the conductive particles become locked between the conductive areas of the mating surfaces. Under pressure and heat, the non-conductive matrix shrinks and forms a stable mechanical connection between two surfaces while the conductive particles within the matrix coalesce forming the electrical connection paths between at least two conductive elements on a surface or between two mating surfaces. Because of the anisotropy, ACLs may be deposited over an entire contact region without concern of shorting between conductors. Moreover, as an example ACLs easily enable connection for high-density conductors of greater than 100 (or 1000) and/or multi-conductor components requiring ultra-fine pitch connections of less than 0.04 mm. Pitch capability of ACLs are customizable by adjusting conductive filler particle shape, size and/or distribution.

ACL conductive particle content may be as low as from about 1% to about 5%. Alternatively, conductive particle content may range from about 1% to about 20%. Yet, another alternative is a conductive particle content ranging from about 1% to about 50%. While a low volume loading is typically used because low loading is generally insufficient for inter-particle contact and essentially prevents electrical conductivity in the X-Y axes (X-Y plane) of the adhesive, loading may be particularly important when the filler or particles are compressible, as the application of vertical pressure during bonding elongates particles, increasing the possibility for inter-particle contact.

In addition to allowing the adhesive to flow, the applied heat also cures the anisotropic conductive layer, such that it adheres or becomes adhesive to both the capacitor and at least one of the hermetic seal insulator or ferrule mounting surfaces. When the heat and the force is removed, the capacitor 132 is then firmly attached to the hermetic seal subassembly 120, and the conductive spheres remain in place and in electrical contact with nail heads 111NH and 114NH.

Figure 28:
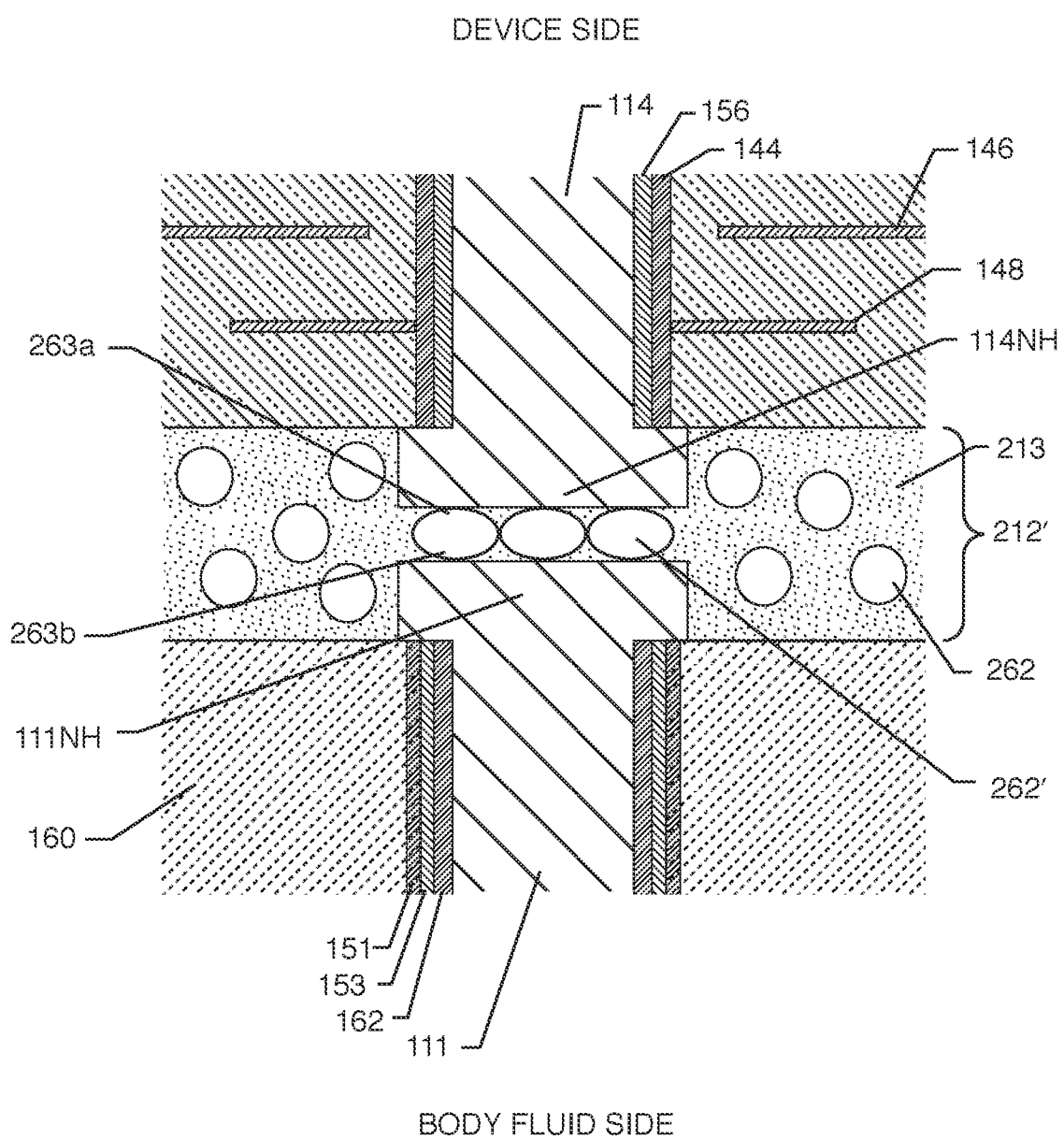
FIG. 28 is an enlarged side sectional view taken along lines 28-28 of FIG. 27 better showing how the conductive particles within the anisotropic conductive layer are captured thereby creating an electrical connection.

This is better understood by referring to FIG. 28, which is taken from section 28-28 from FIG. 27. FIG. 28 shows a blow-up of the two paired nail heads 111NH and 114NH in electrical contact with the conductive spheres. FIGS. 27 and 28 depict the trapped spheres (262, 262') with transformed shapes (262') due to the compressive force applied. However, depending on the conductive particles within the adhesive used to make the electrical connection, the particles may retain their original shape. In the case where the particles maintain their original shape, this means that the particles are rigid, such as a solid metal, a clad or an electroplated solid metal. In this case, if the solid metal particle was compressed between two solid metal nail heads, electrical contact would only be at the tangent points of the particles. Therefore, it would be desirable to use contact pads that are at least somewhat flexible. In other words, it is desirable to use contact pads that have a lower durometer than a solid metal. Another example would be the use of a conductive elastomer, such as a conductive rubber. A thin conductive rubber pad can be disposed on at least one surface so that when the ball is compressed, it indents into the conductive rubber thereby increasing its electrical contact area. Having at least one of the ball or conductive particles being compressed, or at least one of the mounting areas or surfaces being compressed, is important to guarantee the long-term electrical stability of the electrical connection. For example, as long as a flexible ball is compressed within its elastic limit, it will push against its mated surfaces in such a way that the electrical contact is maintained. The same is true if the ball is rigid and at least one of the mounting surfaces is compressible within its own elastic limit, such that it will always apply a longitudinal force (along the Z axis) through the conductive particle itself.

Referring again to FIG. 28, in the area between the nail heads, one can see spheres 262' in contact with each other and with the nail heads 111NH and 114NH. Outside the area of the nail heads, one can see that these spheres 262 are not in compression and are also electrically isolated from each other. Now referring back to the area between the two nail heads 114NH and 111NH, one can see that these conductive spheres are in conductive relationship at their top 263a and at their bottom 263b with the two respective nail heads. This creates a conductive pathway through the leadwire 111 to the device side leadwire 114.

Figure 29:
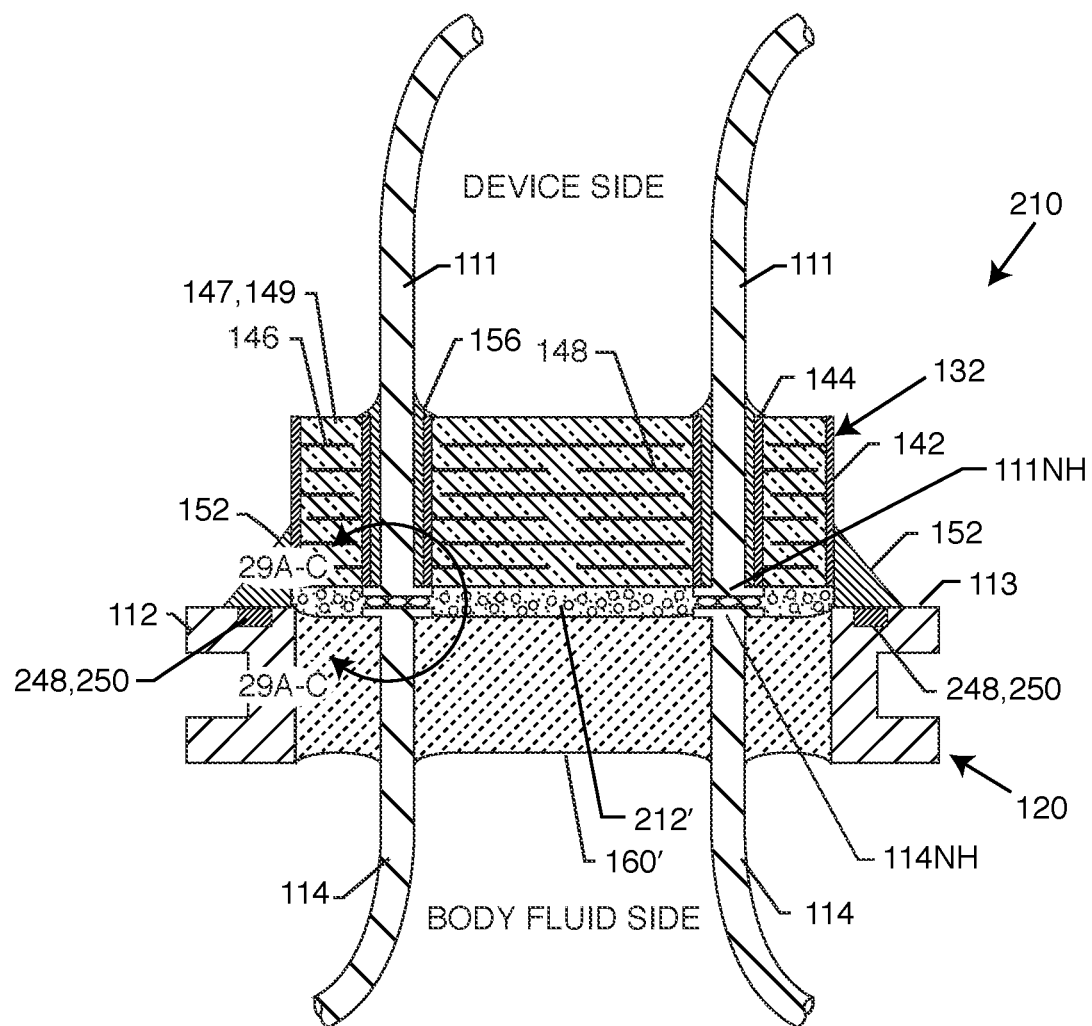
FIG. 29 is a side sectional view of another embodiment taken generally from section 29-29 from FIG. 26 and illustrates that the hermetic seal may be of glass.
Figure 29A:
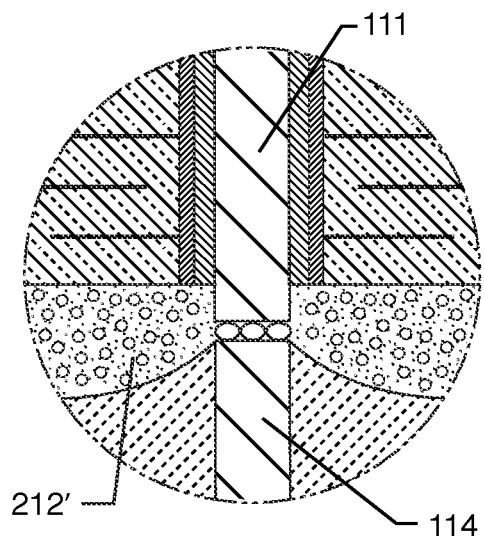
FIG. 29A is an enlarged side sectional view of one embodiment taken along lines 29A-29A from FIG. 29.
Figure 29B:
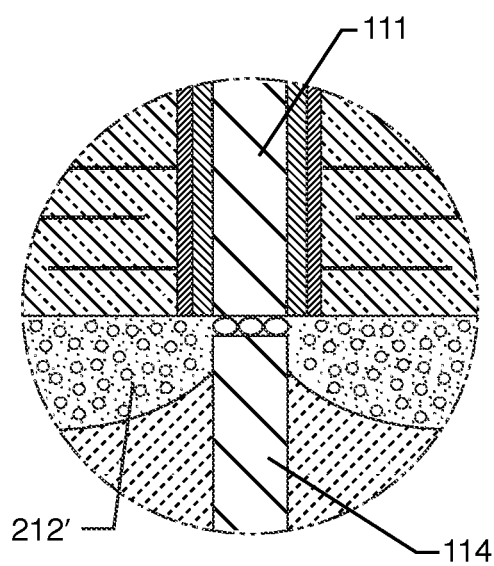
FIG. 29B is an enlarged side sectional view of one embodiment taken along lines 29B-29B from FIG. 29.
Figure 29C:
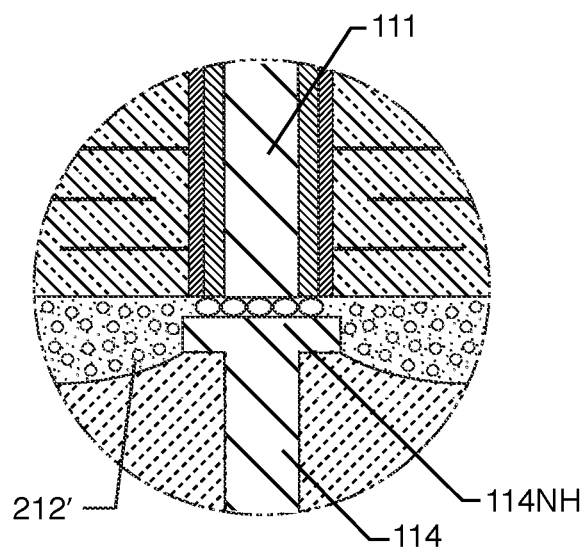
FIG. 29C is an enlarged side sectional view of one embodiment taken along lines 29C-29C from FIG. 29.

FIG. 29 is very similar to FIG. 27, except that the hermetic seal insulator is a glass seal or glass-ceramic seal 160', This eliminates the need for gold braze connections 162 and 150, as previously illustrated in FIG. 27. Fusion or compression glasses form their own mechanical and hermetic attachment both to the inside of the ferrule and to the leadwires 114. However, in a similar fashion as indicated in FIG. 27, there are opposed nail heads 111NH and 114NH, as previously described in FIG. 27. These opposed nail heads compress the conductive spheres within the anisotropic conductive film 212' and create conductive pathways along the leadwires from the body fluid side 114 to the device side 111. FIG. 29A, FIG. 29B and FIG. 29C are taken from FIG. 29, as indicated. FIG. 29A indicates that instead of nail heads, the leadwire 111 protrudes and compresses the conductive spheres that are trapped between the opposed leadwire ends 111, 114. The word "trapped" means compressed in that, the conductive spheres, in this area, form an electrical connection from the body fluid side lead 114 to the device side lead 111. FIG. 29B illustrates that the body fluid side leadwire may protrude and the device side leadwire 111 may be flush. FIG. 29C indicates that the body fluid side leadwire 114 may have a nail head structure 114NH which opposes a flush device side leadwire 111. It will be appreciated that there could also be a device side leadwire 111 with a nail head 111NH opposite a non-protruding body fluid side leadwire 114, as illustrated in FIG. 29A.

Figure 30:
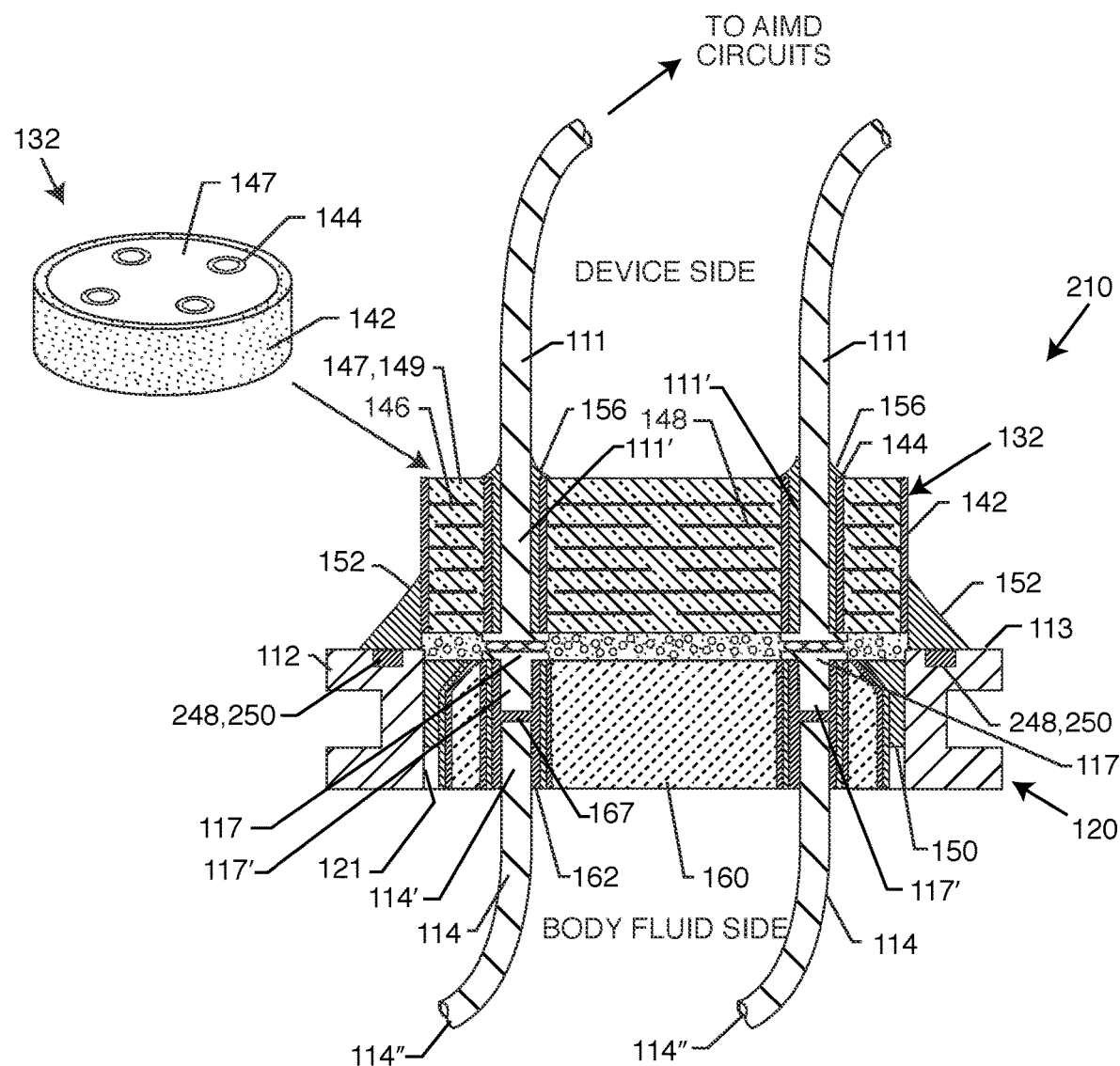
FIG. 30 is a side sectional view very similar to FIG. 27 now illustrating the body fluid side leadwire can be made from different materials to reduce cost.

FIG. 30 is very similar to FIG. 27 but illustrates the use of much less expensive leadwire materials. In this figure, the filtered hermetic seal subassembly 210 of FIG. 30, one can see that the body fluid side leadwire 114 is discontinuous in that, it has an end that is at least partially disposed within the passageway through the hermetic seal insulator 160. That end is illustrated as end portion 114'. The other end of the lead 114" would be routed to implanted human tissue-stimulating electrodes (not shown). There is then a short nail head segment 117', 117, as illustrated. As previously described, this allows for the compression of the conductive spheres of the ACF film in selected area between the body fluid side lead 114 and the device side lead 111.

Figure 31:
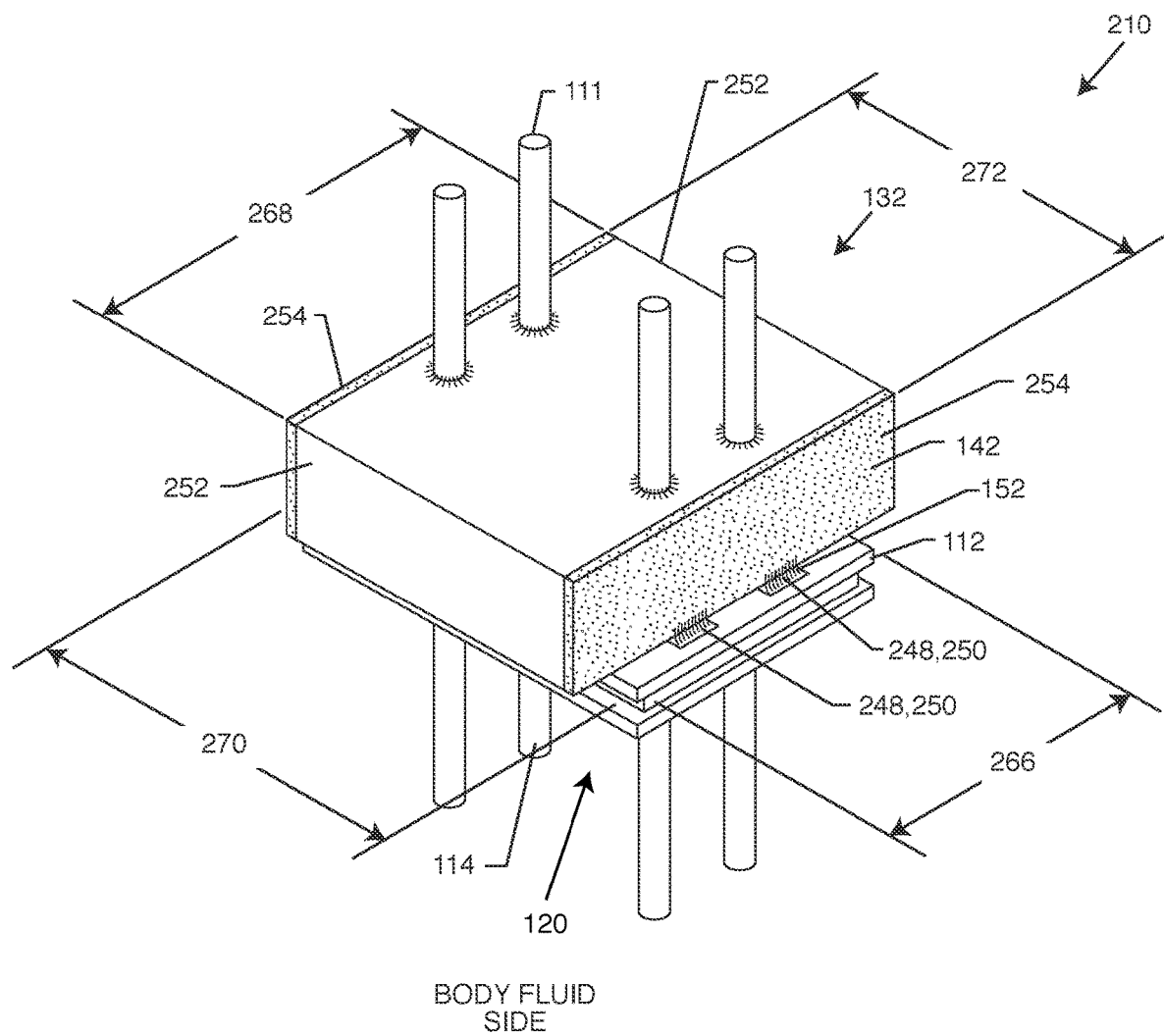
FIG. 31 is an isometric view similar to FIG. 26 now showing an overhanging capacitor for an increase in effective capacitance area.

FIG. 31 is very similar to FIG. 26, except in this case, the feedthrough capacitor 132 overhangs 268 the ferrule edge 266, as indicated. Overhanging capacitors are especially useful for increasing the effective capacitance area (ECA) of the capacitor, therefore, making it more volumetrically efficient. Overhanging capacitors were first described in U.S. Patent Application Pub. No. 2018/0236244, the contents of which are incorporated herein fully by reference.

FIG. 32A illustrates an internally grounded feedthrough capacitor 132 exploded away and ready for installation on internally grounded hermetic seal assembly. The hermetic seal assembly, in this case, have 8 active pins (octopolar), 1 telemetry pin and 1 centrally located internal ground lead or pin 111gnd. The ground pin is electrically grounded to the ferrule through a peninsula structure 139. The internal ground lead or pin is either gold-brazed or laser welded to this peninsula thereby forming a very low impedance and low resistance connection to the ferrule 112. A gold braze 150 hermetically seals the insulator to the ferrule 112. Gold brazes (not shown) mechanically and hermetically seal the leadwires 114 to the insulator 160. Item T is an RF telemetry pin and must not be filtered since it needs to freely pass high-frequency programming signals from a remote programmer (not described). Referring once again to FIG. 32A, one can see that the body fluid side leadwires or pins 114 terminate in nail heads 114NH that are generally proud of the device side surface of the insulator 160. The feedthrough capacitor 132 does not yet have its nail head leadwires installed. As shown, device side leadwire 111, 111NH is ready to be soldered and installed 111NH, 111 in each one of the active passageways by solder or conductive adhesive. Also shown is one ground leadwire 111gnd that is also installed into the capacitor.

Accordingly, the hermetic feedthrough assembly of FIG. 32A has 8 active pins that can deliver therapeutic pacing pulses and/or sense biological signals, a telemetry pin, that might also be called an active pin, and a ground pin 111gnd. In FIG. 32B, one will notice that there is no active electrode plate 148a associated with the telemetry pin. Referring once again to FIG. 32A, the feedthrough capacitor 132 is novel and that no ground electrodes are brought to its perimeter or outside diameter surface and accordingly, there is no ground or perimeter metallization 142 at all.

U.S. Pat. No. 5,905,627 describes internally grounded capacitors, the contents of which are incorporated herein fully by reference. Also, describing internally grounded capacitors are U.S. Pat. Nos. 6,529,103 and 6,765,780, the contents of which are also incorporated fully herein by reference.

FIG. 32B shows the feedthrough capacitor 132 of FIG. 32A exploded, such that one can see its active electrode plates 148a and 148h and also its ground electrode plates 146. As shown, any number of these can be interleaved and sandwiched construction to achieve the desired capacitance value.

Figure 32D:
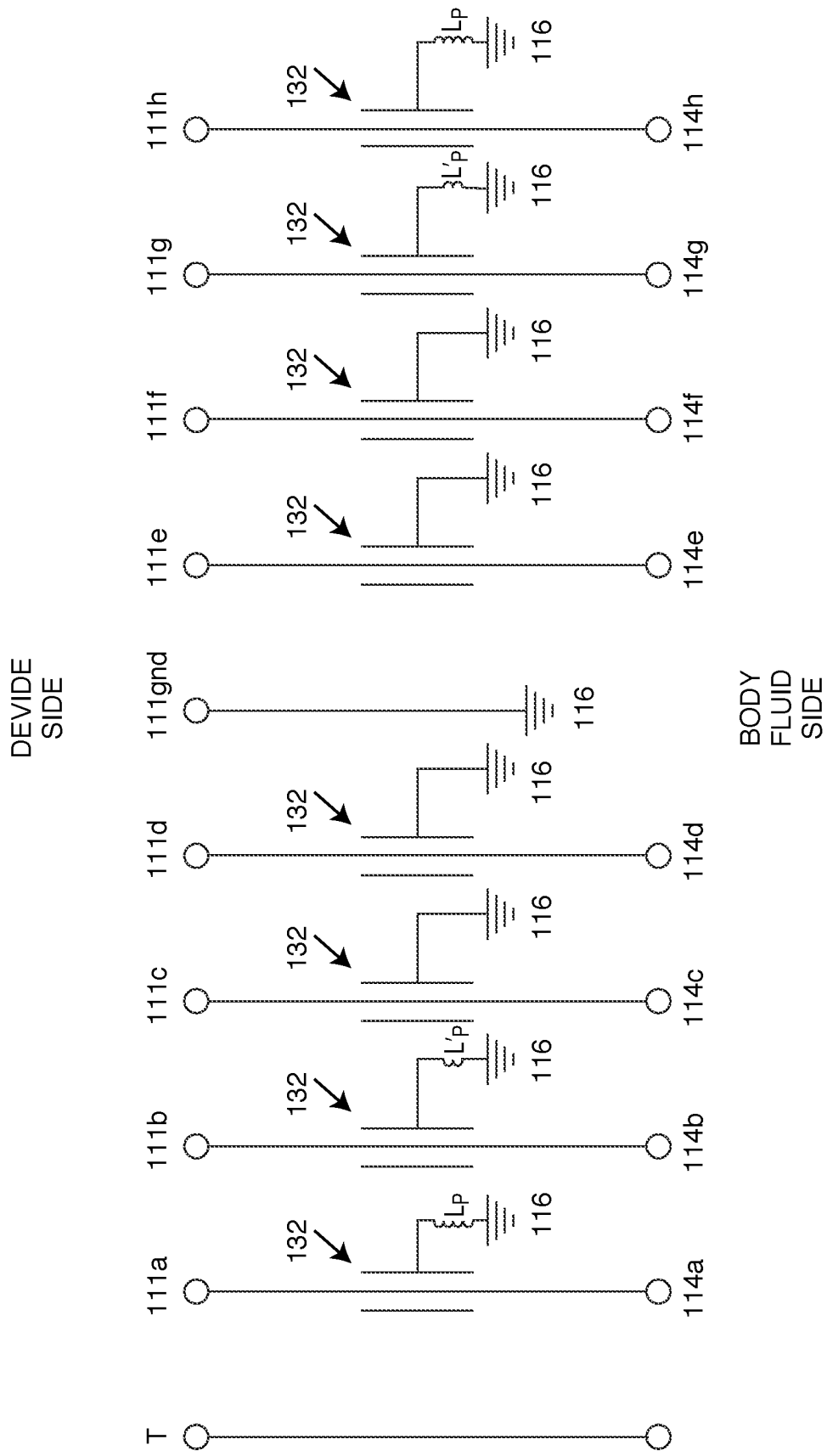
FIG. 32D is an electrical schematic illustrating that the pins 111c-f that are closest to the ground 111gnd have little to no (insignificant) parasitic inductance.

FIG. 32C shows the feedthrough capacitor 132 of FIG. 32A mounted to the hermetic seal terminal and ferrule 112. Since there is no external metallization on the feedthrough capacitor, there is no electrical connection required for the ferrule 112 at all. Internal ground lead 111gnd is generally of non-oxidized material, such as palladium or platinum or alloys thereof. Accordingly, a very low resistance connection is made from the capacitor ground electrode plate 148 and 146 through ground pin 111gnd and in turn, to ferrule 112. However, referring back to FIGS. 32A through 32C, there is a serious downside. This is because the active pins that are furthest from the ground pins, which would include active pins 148a and 148h are a very long distance away from the single ground 111gnd. Undesirably, inductance builds up across the ground electrode plates 146, such that this inductance undesirably ends up in series with a capacitor's ground electrical path. This parasitic inductance is highly undesirable since inductances at high-frequency will provide an inductive reactance in series with the feedthrough capacitor. This is very much analogous to an undesirable ohmic loss in this area. Schematic diagram, FIG. 32D, illustrates that the pins 111c-f that are closest to the ground 111gnd have little to no (insignificant) parasitic inductance. However, the outer most pins 111a, 111b, 111g and 111h do have this parasitic inductance LP and L'P, which can seriously degrade filter performance. The solution to this problem is attempted as shown in FIGS. 37 through 42 of U.S. Pat. No. 6,765,780 (i.e., '780 patent), the contents of which are incorporated herein fully by reference.

Figure 33:
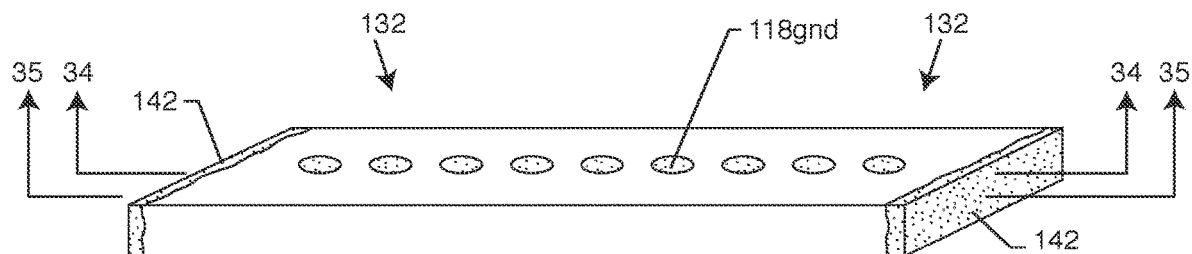
FIG. 33 is an isometric view of an internally grounded and externally grounded feedthrough capacitor (i.e. "hybrid" capacitor) taken from FIG. 37 of the '780 patent.
Figure 34:
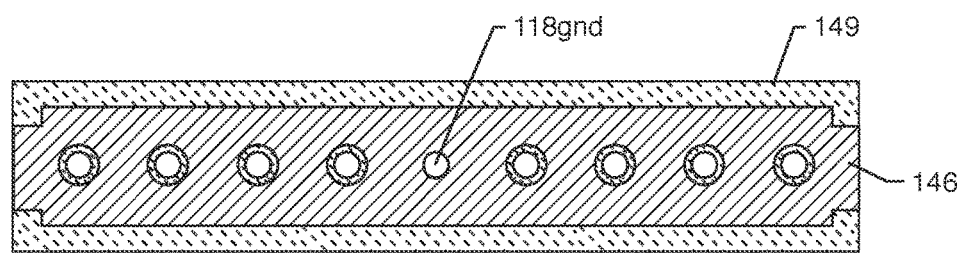
FIG. 34 is taken from section 34-34 from FIG. 33.

FIG. 33 herein is an isometric view of the internally grounded and externally grounded feedthrough capacitor taken from FIG. 30A of the '780 patent. This is best understood by referring to the cross-sectional view shown herein as FIG. 34, which is taken from section 34-34 from FIG. 33. This illustrates the ground electrode plate 146. As one can see, the ground electrode plate 146 is configured such that it will be in electrical contact with ground pin 118gnd. It is also brought out to the short ends (the left and right side of a rectangular feedthrough capacitor), such that a ground metallization 142 can be placed on both ends. The internally and externally grounded feedthrough capacitor, as illustrated in FIGS. 33 through 38 herein, are defined as hybrid internally grounded feedthrough capacitors. The word hybrid comes from the fact that they have an internal ground feedthrough passage as well as external metallizations 142. This multipoint or hybrid grounding system is important, such that each of the active passageways represented by pins 111 in FIGS. 37 and 38, all have a high degree of filter performance (insertion loss). This long and narrow feedthrough capacitor cannot be solely grounded by 118gnd only. This is because the outermost pins or the furthermost pins from 118gnd would have highly degraded insertion loss due to the inductance build up across the internal electrode plates. Accordingly, by also grounding the feedthrough capacitor across its ends, at metallization locations 142, a second and third low inductance path is created. Accordingly, all of the pins of the feedthrough capacitor will offer a high degree of filter performance.

Figure 35:
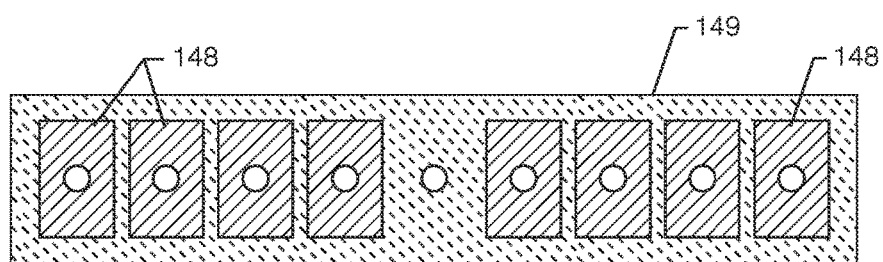
FIG. 35 is taken from section 35-35 from FIG. 33 and illustrates the eight active electrode plates.

Referring to FIG. 35, one will realize that the telemetry pin T that was previously described in FIGS. 32A and 32B, has been eliminated for simplicity. Accordingly, in FIGS. 33 and 35, only active pins for the feedthrough capacitor are shown.

FIG. 35 is taken from section 35-35 from FIG. 33 and illustrates the 8 active electrode plates 148. FIG. 42 of the '780 invention shows the capacitor in cross-section with an electrical connection from the capacitor ground metallization 914 to gold braze pad areas 946, which in accordance with that invention, are a continuous part of the hermetic seal between the ferrule and the insulator 924. As previously described, a negative of this construction is that the gold braze 946 will flow due to gravitational forces during high-temperature gold braze furnace operations, when the gold becomes molten or liquid.

Figure 36:
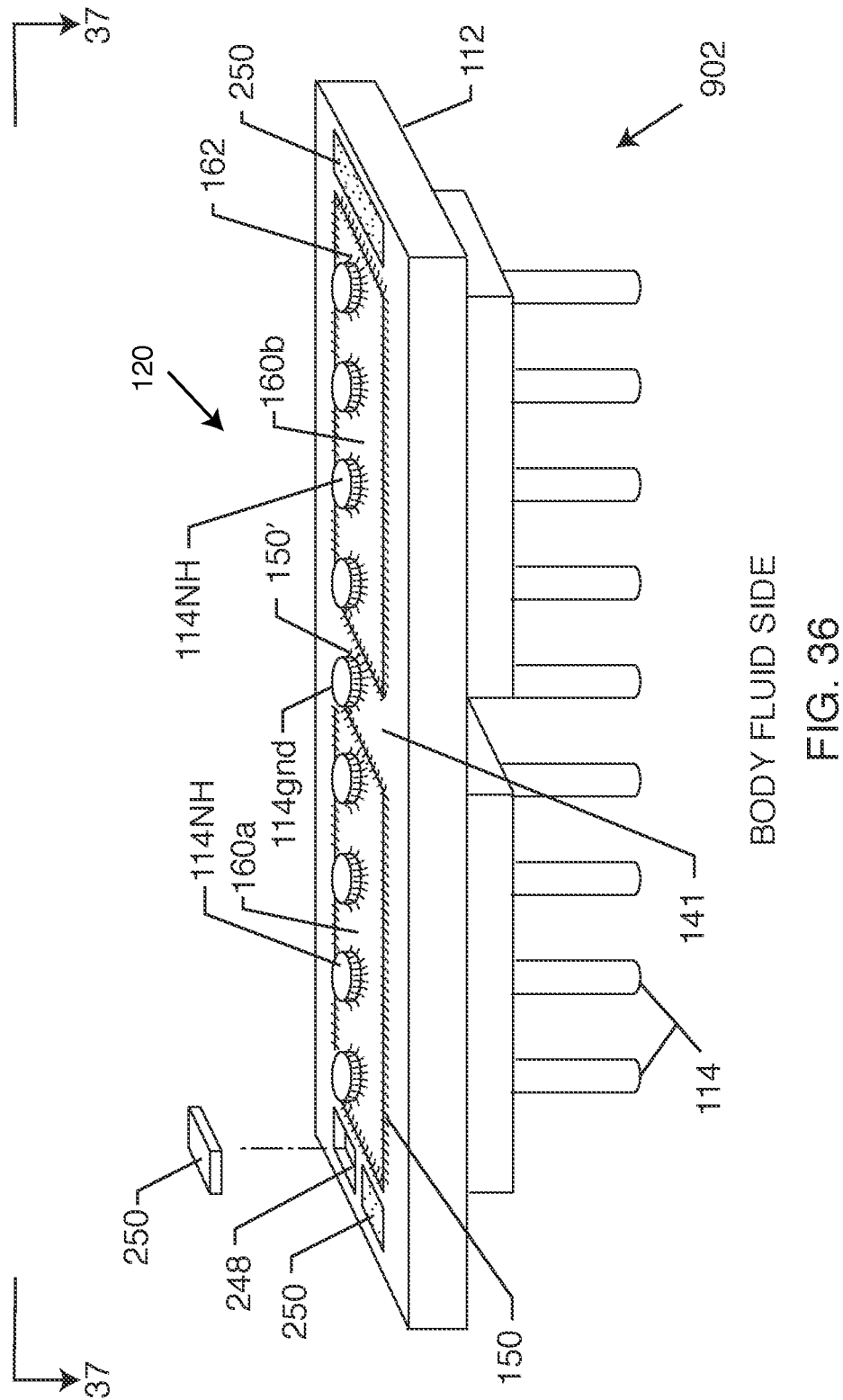
FIG. 36 is an isometric view similar to FIG. 40 of the '780 patent now illustrating a hermetic feedthrough utilizing nail headed leadwires and gold pocket pads for the present invention.

FIG. 36 illustrates the present invention wherein, FIG. 42 of the '780 invention has been modified in accordance with the present invention. That is, there are one or more pocket areas 248 formed that have solid bottoms and side walls (like a swimming pool) that fully contains the gold preform and contact area 250. As illustrated on the left side of FIG. 36, these pockets 248 can be discontinuous or as shown on the right side, they can be joined together and continuous. The resulting broadband and high-frequency performance of such an arrangement overcomes any problems with the previously described parasitic inductances. In other words, it is now assured that every one of the pins has proper high-frequency and broadband and filter performance (attenuation or insertion loss).

Figure 37:
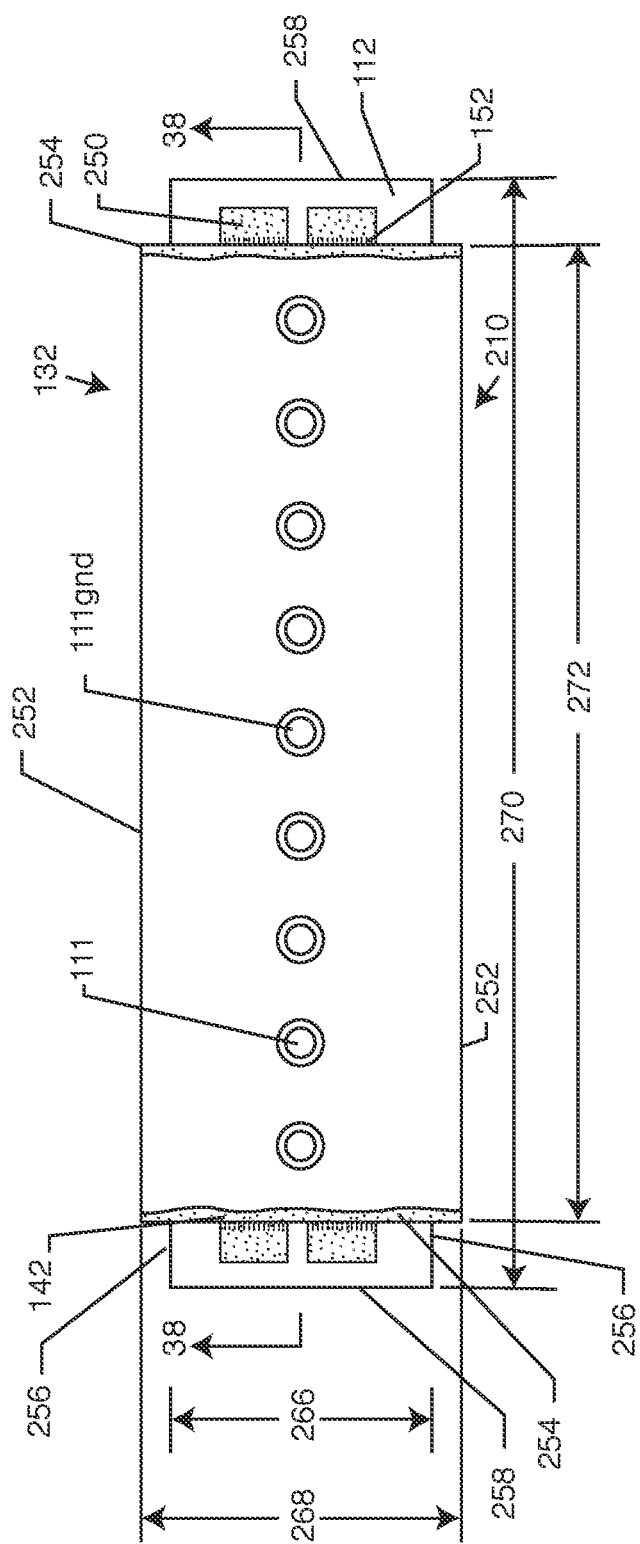
FIG. 37 is a top view taken along lines 37-37 from FIG. 36 now illustrating the feedthrough capacitor of FIG. 33 mounted onto the hermetic terminal of FIG. 36, except that in this case, the rectangular feedthrough capacitor is wider (overhanging) than the ferrule for an increase in effective capacitance area.

FIG. 37 illustrates the feedthrough capacitor of FIG. 33 mounted onto the hermetic terminal of FIG. 36, except that in this case, the rectangular feedthrough capacitor is wider 268 than the ferrule 266. As previously described, this greatly improves volumetric efficiency. Referring back to FIG. 32A, it will be appreciated that one or more telemetry pins could also be added to the structure as illustrated in FIG. 37. In this case, the telemetry pin would not be associated with a capacitor active area. Referring back to FIG. 37, one can see that an advantage of this construction is the capacitor and the ferrule have both been kept relatively long and narrow, so they will fit into an AIMD without unduly increasing its thickness. As previously described, this is very important so that the resulting AIMD be thin so that it is comfortable in a patient tissue pocket. It will also be appreciated that instead of the inline pins, as illustrated in FIG. 37, the pins may be staggered, as previously illustrated in FIGS. 32A, 32B and 32C.

Referring once again to FIG. 37, at least a first edge 252 of the feedthrough capacitor extends beyond a first outermost edge 256 of the ferrule. Furthermore, at least a second edge 254 of the feedthrough capacitor does not extend beyond a second outermost edge 258 of the ferrule. This then allows for the ground metallizations of the capacitor to be connected to the gold pocket pads 250 while also allowing for an increase in effective capacitance area due to the larger capacitor size.

Figure 38:
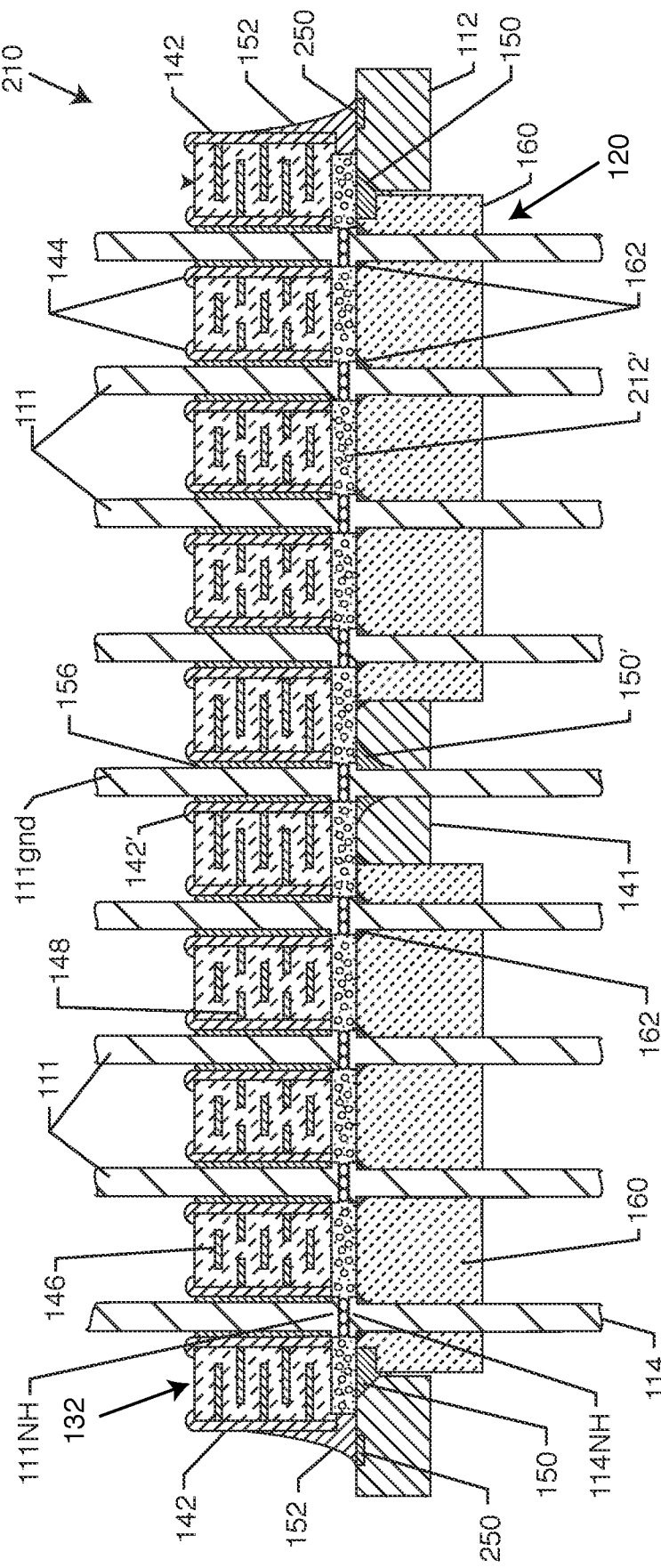
FIG. 38 is a side sectional view taken generally from section 38-38 from FIG. 37.

FIG. 38 is a sectional view taken from section 38-38 from FIG. 37. The capacitor internal ground pin 111gnd is shown electrically connected to the capacitor internal ground metallization through electrical connection material 156. The capacitor ground metallization 142 on the right and the left-hand side, is shown electrically connected 152 to the novel pocket and gold braze areas 250 of the present invention. As one can appreciate, the end pins are no longer very far from ground and accordingly, do not have too much parasitic inductance. In other words, this hybrid internally grounded filter has greatly improved and reliable high-frequency performance.

Referring back to FIG. 38, one can see that the device side leadwires 111 incorporate a nail head 111NH and the body fluid side leadwires 114 also incorporate a nail head structure 114NH in accordance with the present invention. This allows the conductive particles to be compressed in the area to create conductivity between the body fluid side leads 114 and the device side leads 111.

Figure 38A:
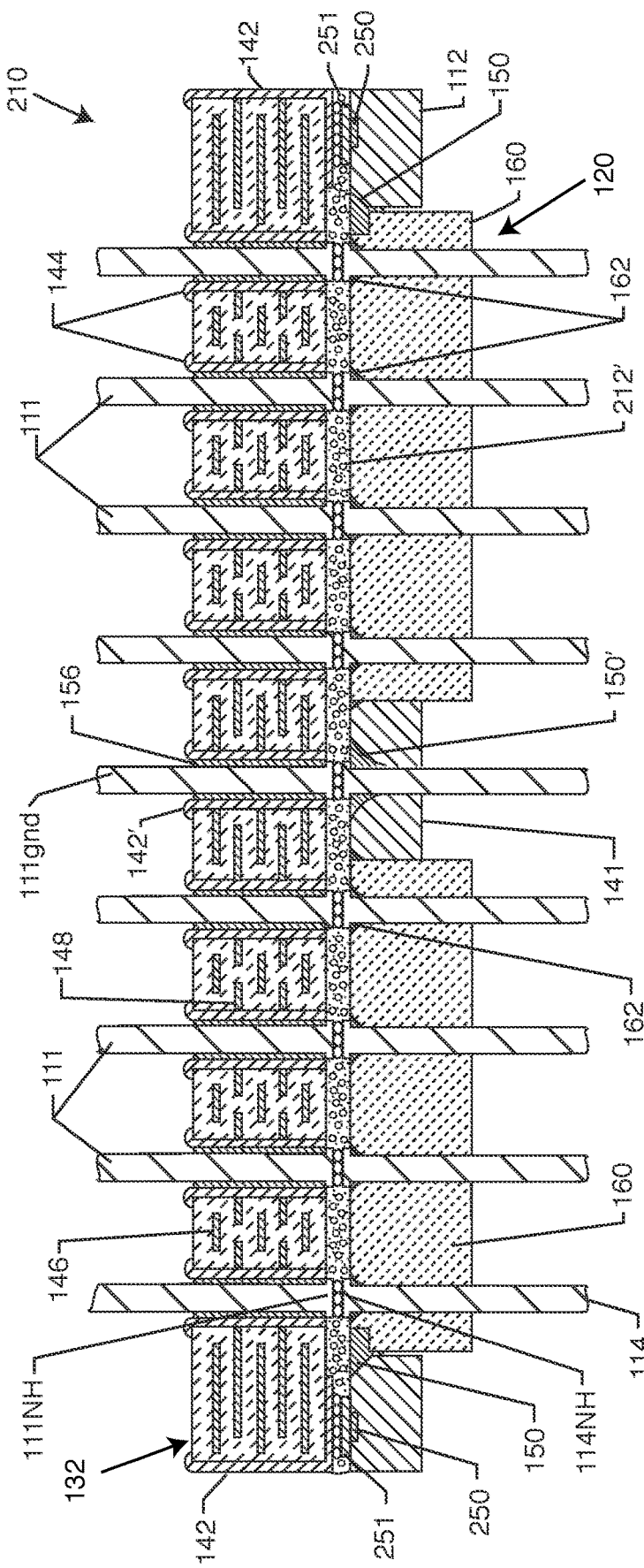
FIG. 38A is a side sectional view taken generally from section 38-38 from FIG. 37 and is similar to FIG. 38, however now the metallization on the capacitor is disposed on at least a portion of the capacitor underside to facilitate electrical attachment with a metal addition to the gold braze pocket pad.

FIG. 38A is very similar to FIG. 38, except the feedthrough capacitor 132 has been widened such that its ground metallizations 142 are disposed over and past the area of the gold pocket pad 250. In this case, there is metal addition 251 that has been co-brazed over the pocket pad. In one embodiment, the gold pocket pad could be of gold brazed material and the metal addition, which would form a proud nail head or rectangle 251 could comprise platinum. Metal additions, such as metal addition 251, is more thoroughly described in U.S. Pat. No. 9,931,514, the contents of which are incorporated herein fully by reference. Referring once again to FIG. 38A, one can see that by aligning the feedthrough capacitor ground metallization 142 over metal additions 251, one is able to use the anisotropic conductive film 212' to make all of the active and the ground connections at the same time. It is understood that there are manufacturing advantages in that, in one single step, all of the electrical connections are made.

FIG. 39 has a peninsula structure 139 to electrically connect the ferrule 112 to the ground pin 111gnd, as shown. This is in contrast to the bridge 150', 141 previously illustrated in FIG. 36. The elimination of the bridge, as illustrated in FIG. 36, means that instead of having two hermetic seal insulators 160a and 160b, one can have one single hermetic seal insulator 160. This offers manufacturing advantages in that, there are less piece parts.

Figure 40:
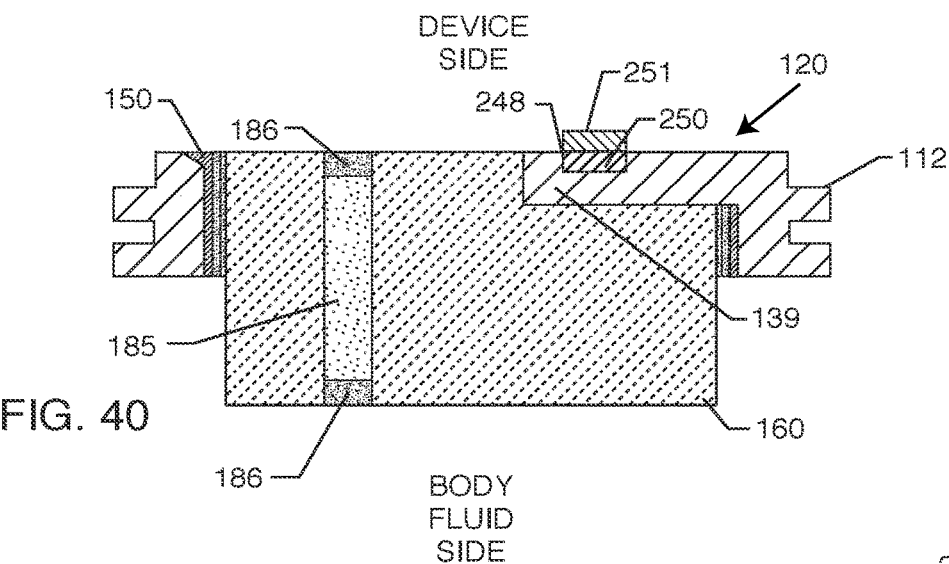
FIG. 40 is a side sectional view illustrating a unique hermetic seal subassembly wherein, a passageway through the hermetic seal insulator has been filled with a sintered or co-fired conductive paste.
Figure 47:
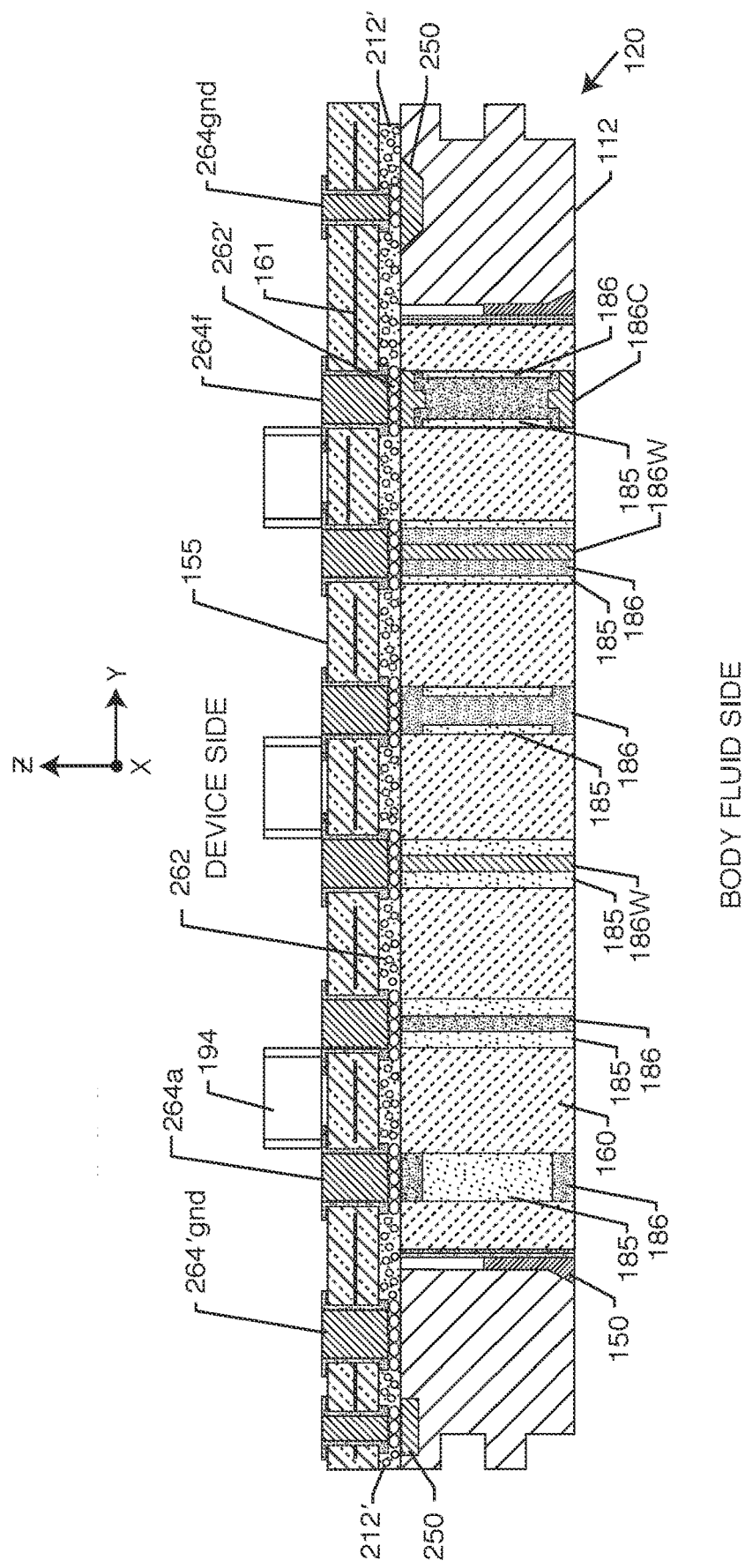
FIG. 47 is a side sectional view of another embodiment of the present invention illustrating a hermetic seal subassembly with various types of co-sintered and filled vias.

FIG. 40 illustrates a unique hermetic seal subassembly wherein, a passageway through the hermetic seal insulator 160 has been filled with a sintered or co-fired conductive paste. In the embodiment of FIG. 40 as illustrated, item 185 would comprise a CERMET or a CRMC (ceramic reinforced metal composite). The two end caps 186 would be of substantially pure platinum. However, there are many options and variations on this. It will be appreciated that the present invention applies to any type of filled passageway or via through an insulator that is co-sintered/co-fired. For example, the contents of U.S. patent application Ser. No. 15/797,278 are incorporated herein fully be reference. Also incorporated herein by reference are U.S. Pat. Nos. 8,653,384; 8,938,309; 9,233,253; 9,492,659; 9,511,220 and 9,889,306. It will also be appreciated that the present invention is applicable to any of the following U.S. patents, including U.S. Pat. Nos. 5,333,095; 5,751,539; 5,896,267; 5,973,906; 5,978,204; 6,765,779 and the like, the contents of all of which are incorporated fully herein by reference. Referring now again to FIG. 40, one will appreciate that any of the options or embodiments described in U.S. patent application Ser. No. 15/797,278 can be embodied in a co-sintered filled via. Referring only to the filled via, FIG. 47 illustrates many of these options.

Referring once again to FIG. 40, one will see that there is a metal addition 251 that has been co-brazed with the gold pocket 250, as indicated. This is important because the metal addition 251 is now proud of the device side surface of the ferrule 112 such that it can compress conductive particles of ACF films.

Figure 41:
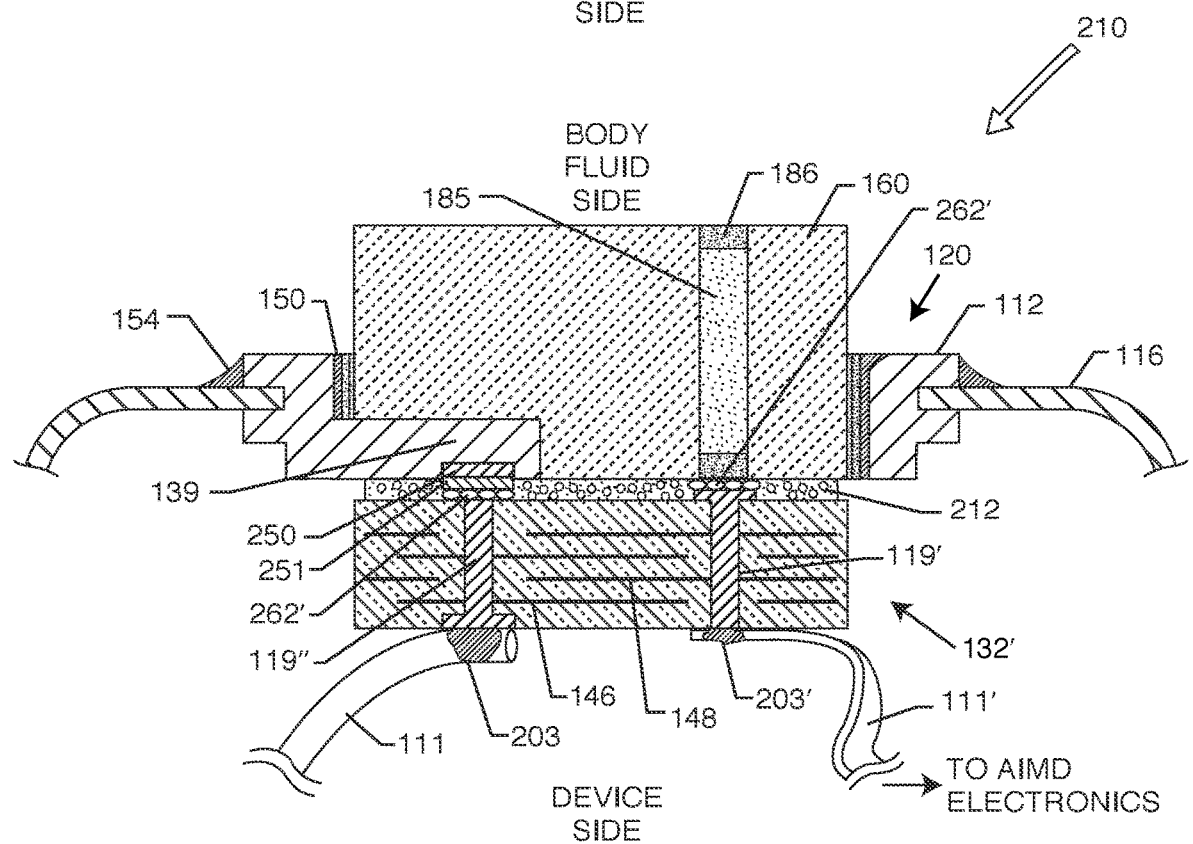
FIG. 41 is a side sectional view illustrating an internally grounded feedthrough capacitor mounted to the novel hermetic terminal subassembly of FIG. 40 utilizing an anisotropic conductive layer for electrical connection.

FIG. 41 illustrates an internally grounded feedthrough capacitor 132' mounted to the novel hermetic terminal subassembly 120 of FIG. 40. Importantly, the capacitor is internally grounded, which is shown on the left side via hole wherein, the capacitor via hole is electrically connected 202 directly to the gold braze pocket 250 and pad 251, in accordance with the present invention. The gold braze pocket and pad 251 provides an oxide-resistant connection to the peninsula structure 139 of ferrule 112. This ferrule peninsula 139 was previously illustrated, for example, in FIG. 39 herein.

The feedthrough capacitor of FIG. 41, on the left-hand side, has a filled passageway which may be filled with a termination paste, a solder or thermal-setting conductive adhesive or the like. It is noted on the left-hand side that this material is not proud of the ACF mounting surface between the capacitor and the hermetic seal subassembly 120. However, the presence of metal addition 251 provides a compression area such that the conductive spheres may be properly compressed and become conductive in the ACF film. A different structure is shown on the right-hand side of FIG. 41. In this case, the feedthrough capacitor has a nail head pin 119', such that the nail head stands up proud of the capacitor mounting surface. In this way, the conductive particles 262' are compressed between this nail head and the co-sintered conductive via 185, 186. On the device side of the feedthrough capacitor are shown leadwires which have either been soldered, resistance welded or the like, to the feedthrough capacitor conductive passageways so they can be routed to AIMD electronic circuits (not shown).

Figure 41A:
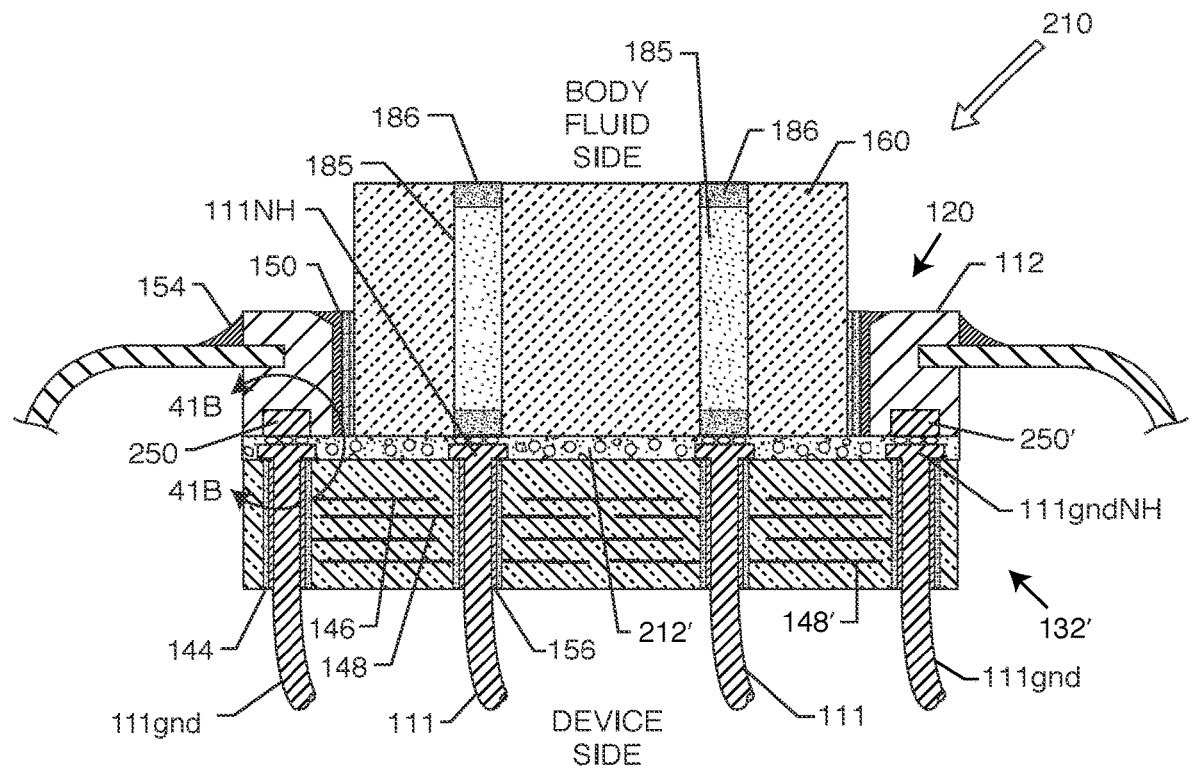
FIG. 41A is a side sectional view illustrating an embodiment having an internally grounded feedthrough capacitor with an increased size that is connected at multiple locations to the ferrule using the gold-filled pocket of the present invention.

FIG. 41A illustrates an embodiment of the internally grounded feedthrough capacitor 132', previously described in FIG. 41. In the cross section of the embodiment illustrated in FIG. 41A, the capacitor is shown to be significantly wider. The capacitor, in this case, is as wide as the adjacent ferrule 112. Referring once again to FIG. 41A, one will see that only two gold pocket pad areas 250 and 250' in accordance with the present invention. The two gold pocket pads 250 and 250' allow multipoint grounding of the capacitor's internal ground electrode plates 146. It will be appreciated that for long and rectangular capacitors there could be one, two or even a plurality of gold pocket pads 250, 250' . . . 250n provided in the ferrule. It will also be appreciated that the internally grounded feedthrough capacitor 132', as illustrated in FIG. 41A, could also overhang the ferrule 112, as previously discussed.

As previously discussed, the feedthrough capacitor 132' is manufactured in a separate manufacturing operation in the hermetic seal subassembly 120. After the feedthrough capacitor is manufactured, then the nail headed leads 111, 111NH are installed by soldering 156 or the like. These nail heads are important because they stand proud of the capacitor mounting surface such that they can compress the conductive spheres 262' in the ACF film 212'. When the capacitor's mounted against the hermetic seal insulator and against the ACF film, the ACF films are compressed in the area of the nail heads against the co-sintered conductive vias 185, 186, as illustrated. It will be appreciated that the ACF film is also compressed in the area of the ground nail heads 111gndNH, as indicated.

Figure 41B:
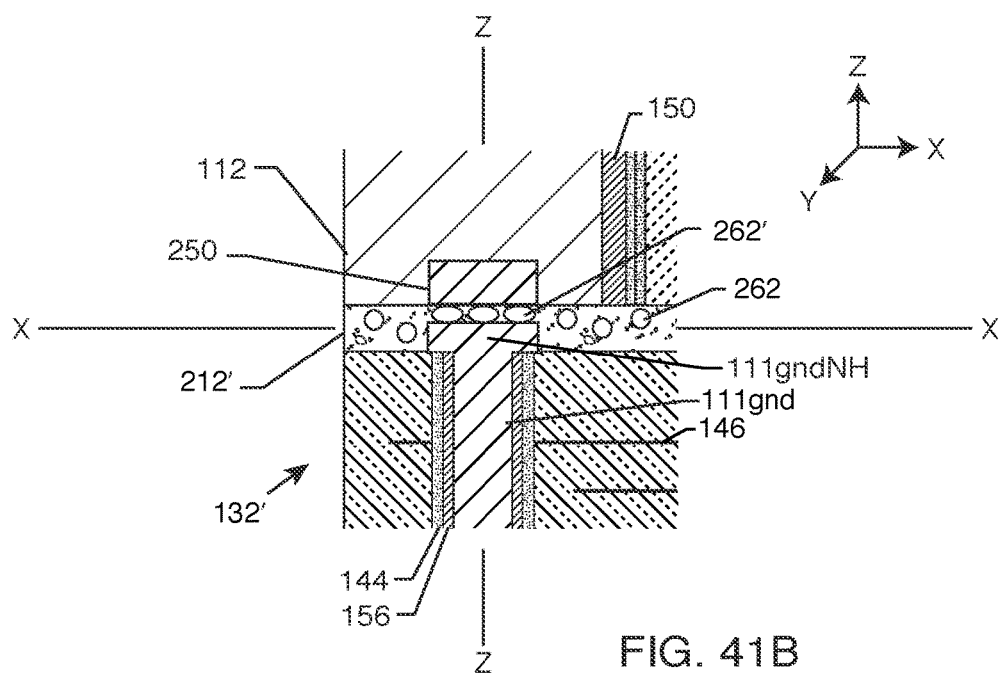
FIG. 41B is an enlarged sectional view taken along lines 41B-41B of FIG. 41A better showing the anisotropic conductive layer for making electrical connection to the gold-filled pocket of the present invention.

FIG. 41B is taken from section 41B-41B from FIG. 41A. This shows a close-up of a gold bond pad 250. The ground nail head 111gndNH abuts conductive spheres 262' and are compressed thereby making electrical connection between the ferrule, which is system ground 112, and the ground pin 111gnd, which is connected to the feedthrough capacitor's ground electrode plates. It can also be seen in FIG. 41B that the conductive spheres that are not compressed 262 remain electrically isolated and insulated, in accordance with the present invention.

FIG. 42 illustrates an isometric view of a prior art chip capacitor also known as a multilayer ceramic capacitor or MLCC. As shown, the capacitor 194 comprises a dielectric body with metallizations 142, 144 on either end. The reason the active metallization 142 and the ground metallization 144 are shown disposed on either side is that there is no polarity to such a capacitor, and it can be reversed. In other words, grounding only occurs when one side of the MLCC chip capacitor is connected to a ferrule 112. It is understood from reading this disclosure that the present invention may be utilized with the use of different types of capacitors, including types mounted on circuit boards, including but not limited to chip capacitors, MLCC, stacked film capacitors or tantalum chip capacitors.

FIG. 43 is a sectional view taken from section 43-43 from FIG. 42. Shown in section are two sets of electrode plates 146, 148. Again, these are numbered as 146, 148 indicating that either one can be active, or the other set can be ground. Such capacitors are known as 2-terminal chip capacitors. They are not coaxial and are not effective broadband filters up to very high frequency, such as a 3-terminal feedthrough capacitor. This is because they do have internal inductance and will at some frequency, self-resonate. However, when they are disposed physically very close to the point of leadwire ingress into an AIMD housing, they can still be effective EMI filters.

FIGS. 44 and 45 are taken from sections 44-44 and 45-45 from FIG. 43. These illustrate the right and left-hand electrode plate sets of the MLCC or chip capacitor 194. The overlap of these two electrode areas form what is known as the effective capacitance area or ECA.

Figure 46A:
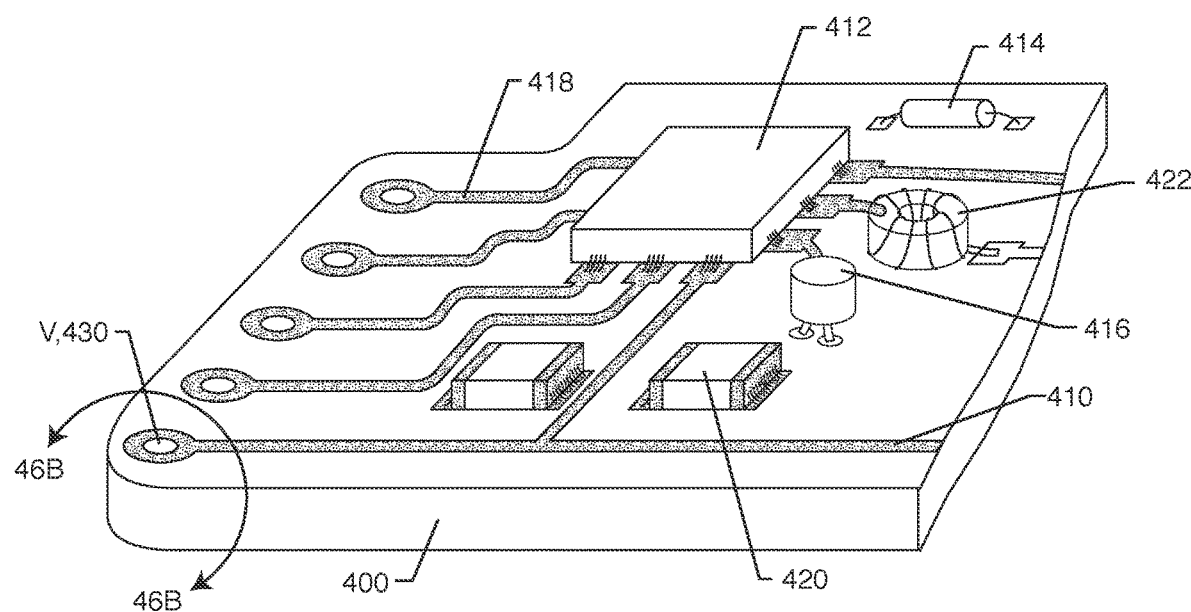
FIG. 46A is an isometric view of a circuit board utilizing anisotropic conductive layers to facilitate the making of electrical connections.

FIG. 46A is a circuit board 400 that would be mounted to a hermetic seal insulator, with the ACF films of the present invention. The circuit board 400 depicted in FIG. 46A represents any AIMD electronic circuit board that may either deliver therapeutic pulses to human tissues or sense human biological signals or both. For example, the circuit board 400 of FIG. 46A could be a circuit board for a neurostimulator, a retinal stimulator, a cochlear implant or the like. Referring once again to FIG. 46A, one will see that it has a number of electronic components that are illustrated for general representation. For example, element 110 could be an electronics microprocessor or ASIC electronics microcircuit and other electronic components are generally shown, such as capacitors, resistors 415, inductors 422, MLCCs 420, all which can be used for biologic sensing, therapeutic pulses, timing or even AIMD programming or reprogramming. The circuit board 400 may have a multiplicity of via holes V, 430. Only five are indicated here, but one would appreciate that there could be more. A circuit board would be mounted directly onto the hermetic terminal subassembly 120, as previously depicted in FIG. 46. The via holes can literally take on dozens of configurations. They could be conductive pads placed underneath or on the bottom of the circuit board. The circuit board could be multilayer 400 with active and ground traces or plates embedded on or within it. Underneath the board, there could be protruding bumps, partial vias, full vias, all of which would be configured in such a way to be connected to the hermetic seal by way of ACF film 262', as previously depicted in FIG. 46. Referring once again to FIG. 46A, one can see, in this particular case, these are eyelet via holes 430.

Figure 46B:
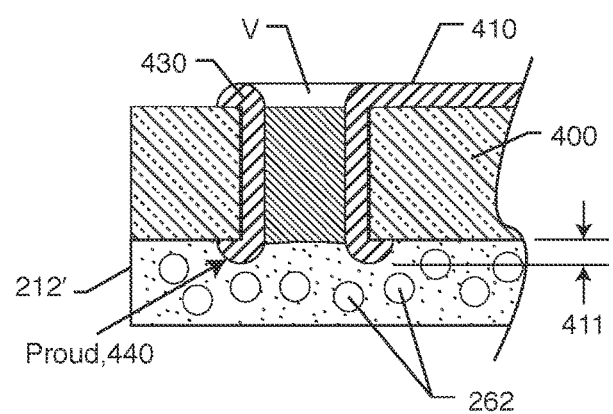
FIG. 46B is a side sectional view taken along the lines 46B-46B from the structure of FIG. 46A.

FIG. 46B is taken generally from section 46B-46B from FIG. 46A showing one of the eyelet via holes in cross-section. In this case, the eyelet V is a filled eyelet, and it has a proud surface 440, which would be disposed between the circuit board and the device side of the hermetic seal subassembly 120. Referring once again to FIG. 46B, one can see that the problem is that the circuit board vias or bumps or contact pads are not perfectly flat, in particular, in the area where they compress against the anisotropic conductive film 212'. The other disadvantage of such typically circuit board features is that they do not protrude out that far 411, such that this makes particle loading of the anisotropic conductive layer 212' very difficult. Not having some of the via holes contacting on some of the LCD crystals in a television set, i.e., not making electrical contact, is not a particularly big deal. This is because there are tens of thousands of connections and channels and few notices if a couple of the circuits aren't conducting. However, this same error becomes a disaster for an active implantable medical device where each and every electrode that's in contact with human tissue, is critically and vitally important. Referring once again to FIG. 46B, instead of an eyelet, if the via hole terminated at a contact pad or contact pads top and bottom, contact pads or solder bumps are generally curved. In another embodiment not shown, a curved or radius surface is also not ideal for compressing optimal compression of the conductive particles 262 in an anisotropic conductive layer 212'. One can see from simple geometry that pressing a curved surface down on the spheres will tend to move some of the conductive spheres laterally, thereby, compromising resistivity in the X-Y axis and/or compromising electrical conductivity in the Z axis (i.e., longitudinal axis).

Figure 46C:
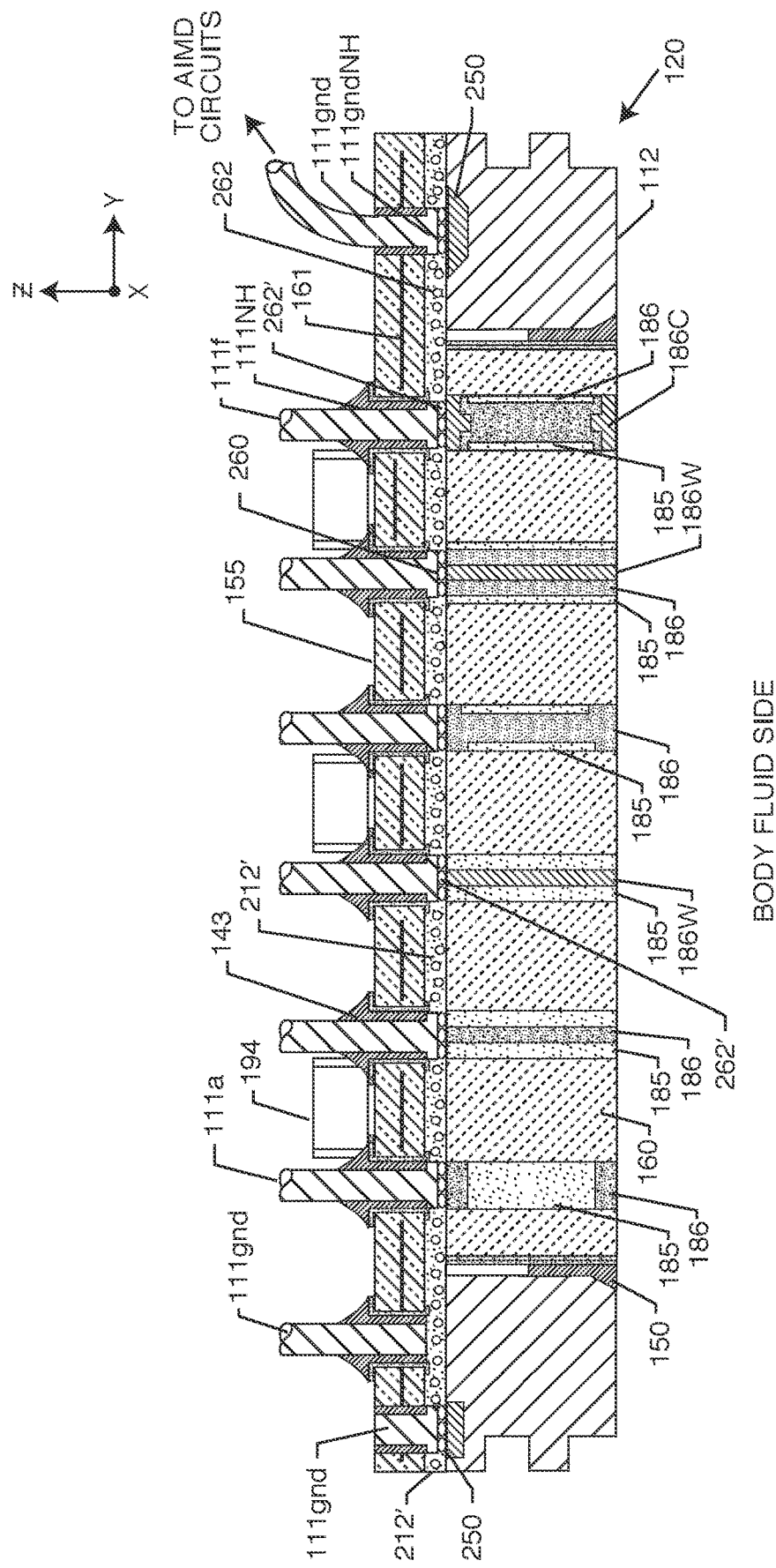
FIG. 46C is a side sectional view of another embodiment of the present invention showing the chip capacitor or MLCC capacitor of FIG. 42 mounted and installed directly on top of a hermetic seal feedthrough assembly.

FIG. 46C illustrates a hermetic seal subassembly with various types of co-sintered and filled vias, which are more thoroughly described in U.S. patent application Ser. No. 15/797,278. Referring once again to FIG. 46C, one can see that there is a circuit board 155 that is disposed on the device side of the hermetic seal insulator. The circuit board has at least one internal ground plate 161, as illustrated. It will be appreciated that the circuit board may have a number of internal ground plates or even an external ground plate. It will also be appreciated that the ground plates could be replaced by ground circuit traces. Various types of circuit boards and grounding techniques are more thoroughly described in U.S. Pat. No. 8,195,295, the contents of which are incorporated herein fully be reference. In accordance with the present invention, the circuit board internal ground plate 161 is grounded to the ferrule 112 through the novel pocket pads 250 of the present invention. It will be appreciated that a combination of external and internal ground plates may be embodied in the circuit board 147. One can see that there are ground vias in the circuit board that have ground pins 111gnd. On the left-hand side, this ground pin is very short and is disposed over the gold pocket pad 250 such that it can compress the conductive spheres due to the nail head structure. There is a ground lead 111gnd, shown on the left side of the circuit board. The ground connection is via the internal ground plate 161, which is routed from the ground pin 111gnd inside the circuit board to the ground via. This allows the ground pin 111gnd to be routed to AIMD electronic circuit board (not shown). On the right-hand side, there is only one ground via hole that is disposed directly over the gold pocket pad 250. This has a previously installed nail headed lead 111gnd, 111gndNH, as indicated. This case is more efficient in that, only one via hole is needed and one ground lead that could also be routed to the AIMD circuit board ground plane. Referring once again to FIG. 46C, one can see that there are a number of MLCC chip capacitors 194. These chip capacitors are disposed between the active leads 111a through 111f with the other side of the chip capacitor connected to the ground plate 161. In this case, each one of the active leads has an MLCC chip capacitor EMI filter. Such chip capacitor EMI filters are more thoroughly described in U.S. Pat. No. 8,195,295, the contents of which are incorporated herein fully by reference. Each one of the active leadwires 111 in the circuit board has a nail head end 111NH that stands proud in the mounting surface area between the bottom of the circuit board and the top (or device side) of the hermetic seal insulator. In this way, the nail head structures 111NH can compress the conductive particles 262' and the ACF film. Since the other conductive particles 262 are not compressed, they remain insulated within the film and are therefore, desirably electrically isolated.

The novel nail head structures 111NH and 111gndNH, as illustrated in FIG. 46C, overcome all of the limitations previously described in FIGS. 46A and 46B. The nail heads can be designed to stand more proud than typical circuit board techniques 411, illustrated in FIG. 46B. In addition, the nail head provides a very flat and rigid surface to which to compress the ACF film conductive particles 262'. Because of the reliably flat and standing proud nail heads, optimal conductivity is achieved in the Z direction while at the same time, in the X and Y planes, the particles remain uncompressed and well insulated within the film or adhesive structure and therefore, have a high insulation resistance.

Referring back to FIG. 41, the metal-insert 251 can also be placed connected to the conductive pathway 185, 186. The metal insert may be co-sintered or post-sinter attached. Referring to FIG. 46C, the metal insert 186C could extend proud of the insulator surface to facilitate the electrical connection by the conductive particles 262'. It will be understood that the metal insert can be described as a metal pad, a co-sintered metal pad, a metal BGA bump, a metal addition, a metal clip or such similar configurations.

FIG. 47 is a modification of FIG. 46C indicating that it would be possible to replace the nail head leadwires with special eyelets that have an especially thick proud surface, as illustrated, and a very flat surface, as illustrated. This would take a type of eyelet not previously seen before in typical circuit board manufacturing.

In summary FIG. 47 is very similar to FIG. 46C, except in this case, the circuit board via holes are solid filled eyelets. These eyelets desirably stand proud of the bottom of the circuit board so that they can desirably compress the conductive particles 262' of the ACF film only in locations where electrical conductivity is required. The eyelets of FIG. 47 are very similar to the eyelets previously described in FIGS. 46A and 46B herein. Referring once again to FIGS. 46C and 47, one of the embodiments or options shown for the co-sintered vias is one having a co-sintered solid wire 186W as shown. It will be appreciated that this solid wire 186W could stand proud on the device side of the hermetic seal insulator to therefore assist in compressing conductive particles 262' of the ACF film. Also shown are end caps 186C. It will also be appreciated that these end caps 186C, particularly on the device side of the hermetic seal insulator 160, could stand proud, again, for the purpose of helping to compress the conductive particles 262' of the ACF film.

FIG. 48 is very similar to FIGS. 46C and 47, except in this case, the via holes in the insulator have all been fitted with a nail head pin 260, which has been co-soldered or co-swaged in such a way that they stand proud of the bottom of the circuit board. Again, this is so that a proud surface is produced to compress the conductive particles 262' of the ACF film 212', in accordance with the present invention.

FIG. 48A is taken from section 48A-48A from FIG. 48. FIG. 48A indicates that the proud nail head surface 260 compresses the ACF conductive particles 262' directly against the gold braze pocket 250. This makes a very low impedance and low resistance electrical connection which provides for ideal high frequency EMI filtering. It will be appreciated that the vias and nail heads 300 of FIG. 48 and FIG. 48A could be readily applied to any circuit board, as illustrated previously in FIGS. 46A and 46B.

FIGS. 49, 50, 51 and 52 illustrate that it's possible to use an anisotropic conductive layer 212' on the body fluid side of a hermetic seal insulator to connect to a body fluid side leadwire 111 or a lead disposed in a header block, say, for an active implantable medical device. In general, ACLs designed for body fluid exposure are novel to the present invention and must meet the following criteria: the ACL film, resin, epoxy or polymer must itself be both biocompatible, biostable and non-toxic. Materials that suit this purpose would include the family of polyimides, polyamides, polyethylene terephthalates (PET), polydimethylsiloxane (PDMS), polytetrafluoroethylene (PTFE), ethylenetetrafluoroethylene (ETFE), parylenes, polyether block amide (PEBAX), polyetheretherketone (PEEK), polystyrenes, polysulfones, polypropylenes, polycarbonates, polyvinyl chloride (PVC), polyxylylene polymers, silicones, medical-grade adhesives and epoxies.

Also, importantly, the conductive spheres 262' disposed on the body fluid side in the ACL must also be biocompatible, non-toxic and biostable. This limits the ACL to use the following materials: palladium, niobium, platinum, iridium, titanium, carbon, gold, combinations thereof and/or alloys thereof. More specifically, carbon includes amorphous carbon, graphite, graphene, diamond-like carbon, vitreous carbon, pyrolytic carbon, carbon-carbon composites and/or combinations thereof. These carbon materials may comprise whiskers, platelets, sheets, fibers, needles, nano-tubes, spheres, crumpled balls, irregularly shaped carbon agglomerates or combinations thereof. The conductive spheres of the biocompatible ACL may also comprise a number of other biocompatible metals, such as tantalum, zirconium, hafnium, nitinol, ZrC, ZrN, TiN, NbO, TiC or TaC, stainless steel, cobalt-chromium (Co—Cr) alloys, molybdenum, silver and combinations thereof and/or alloys thereof. These materials may not be completely oxide resistant and therefore, to improve their conductivity, any of the following materials may be alloyed with any of the others, or may be such as coated, clad, or plated with a layer of any of the highly conductive oxide resistant biocompatible materials, for example, but not limited to, gold, platinum, palladium and the like. An example would be a titanium conductive sphere 262', which has been platinum, palladium or gold plated. Other metals that are ideal for conductive spheres 262' may include: the platinum group metals or noble metals, which also include palladium, rhodium, ruthenium, iridium, and osmium. As stated before, any of these materials can be additionally coated, clad, or plated with a layer of conductive oxide resistant materials. Stainless steels, in general, can also be considered to be conductive particles, particularly those offering biocompatibility, such as, but not limited to, alloy 316L.

Biocompatibility and non-toxicity means the materials used have to meet certain rigorous criteria. However, biostability, in the presence of electrical pulses, becomes a whole other matter. One needs to demonstrate that over time, the materials used do not migrate or electroplate in the presence of body fluids (saline) and electrical impulses. It is well known in the plating industry that one can plate precious metal, such as gold or platinum, onto other surfaces by the use of conductive paths and proper electrical polarities (electro-plating). Accordingly, the inventors had to take all of these properties into account to provide a list of materials that would make suitable candidates for implantation on the body fluid side.

Figure 49:
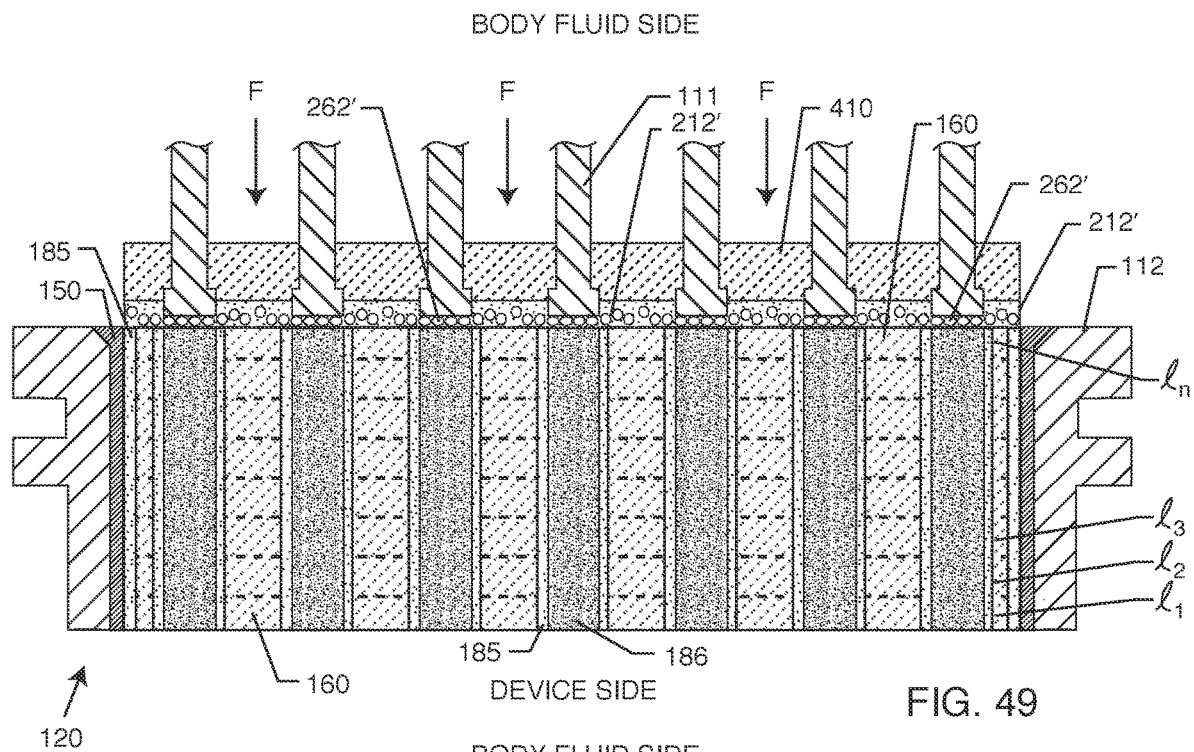
FIG. 49 is a side sectional view of another embodiment of the present invention showing a plurality of electrical connections being made utilizing anisotropic conductive layers.
Figure 50:
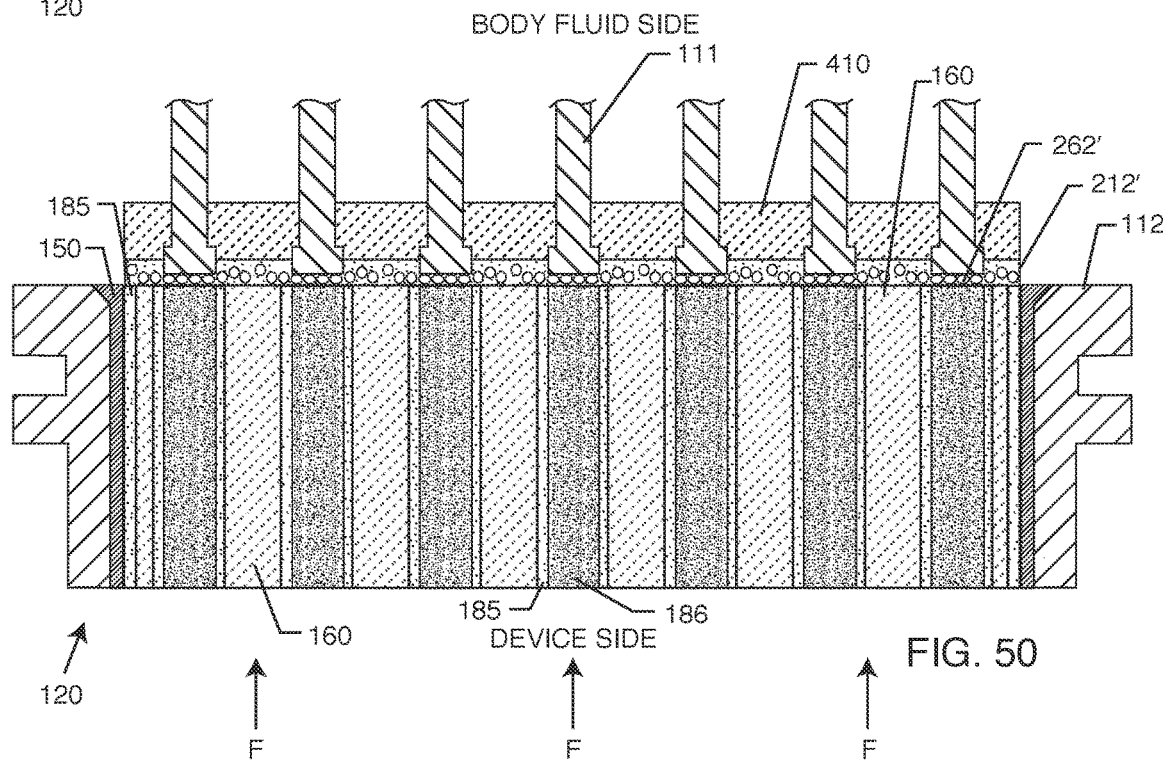
FIG. 50 is a side sectional view similar to FIG. 49, however the insulator was made of a monolithic structure whereas the insulator of FIG. 49 was made in layers.
Figure 51:
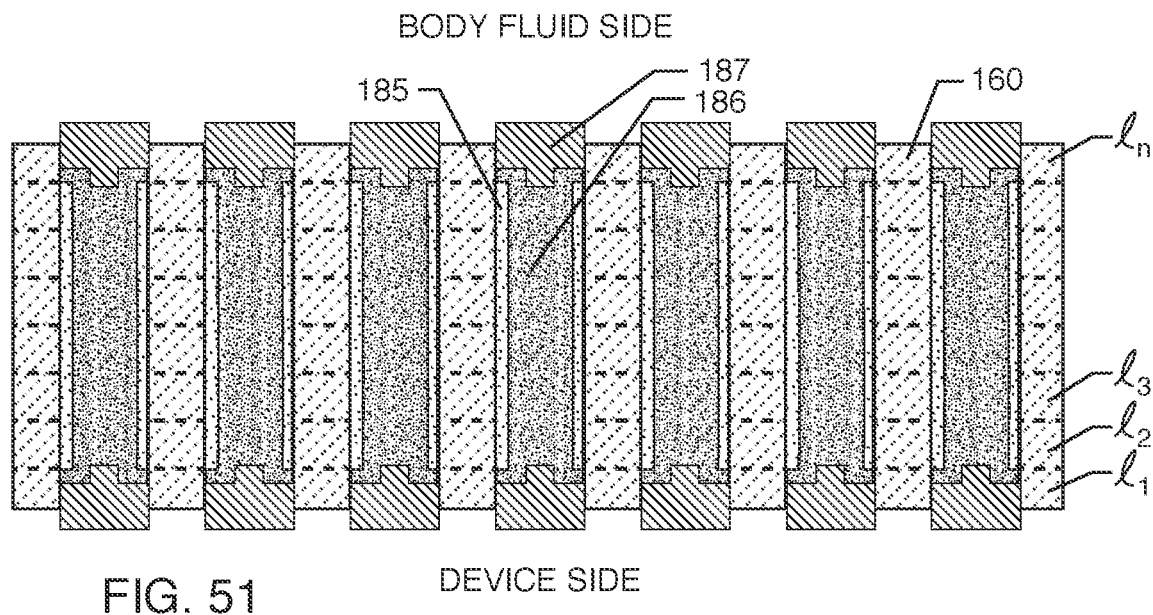
FIG. 51 is a side sectional view of a plurality of co-sintered vias with proud conductive inserts for making electrical attachment to the present invention.
Figure 52:
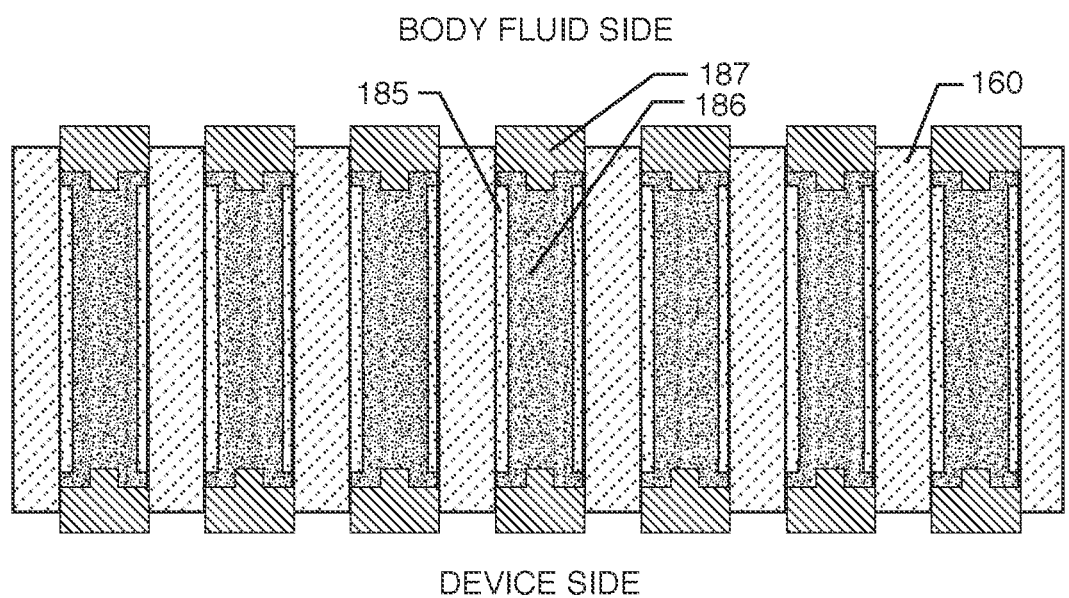
FIG. 52 is a side sectional view similar to FIG. 52, however the insulator was made of a monolithic structure whereas the insulator of FIG. 51 was made in layers.

FIG. 49 has a multilayer insulator 160 made by laminating a plurality of dielectric sheets whereas, in FIG. 50, the insulator is a formed powder insulator made by injection molding, green machining, powder pressing, or pressing powder into a die, herein defined as a pressed powder insulator 160. As indicated, there can be a variety of via holes 185, 186. As previously stated, there are seven via holes shown, but the present invention is applicable to AIMD hermetic seal subassemblies that have tens, hundreds or even thousands of vias that are of a very close pitch. In this case, material 185 is a ceramic reinforced metal composite, which is drilled and then filled with a substantially pure platinum 186. The CRMC 185, the platinum-paste 186 and the alumina insulator paste 186 are all co-fired to form a homogeneous and hermetic structure, as indicated. Various types of ceramic reinforced metal composite vias are more thoroughly described in U.S. Pat. No. 10,249,415, the contents of which are herein incorporated fully by reference. Referring once again to FIG. 49, one can see that there is a thin rigid substrate 410 through which all of the through pins 111 pass. This is on the body fluid side and this rigid plate 410 must be of a biocompatible non-conductive material (electrically insulative). For example, an ideal candidate would be a thin sheet of fired substantially pure alumina ceramic. It is not necessary that the pins 111 be held rigidly within the sub-plate or rigid plate 410. The purpose of this plate is so that forces F can be applied during the application of heat and a force to compress and cure the anisotropic conductive film 212' can be applied, such that the conductive particles 262' within the anisotropic conductive film 212' are selectively compressed in the areas where conductivity from the body fluid side pins 111 to the device side is achieved. No device side electrical connections are shown in this case since these have already been illustrated throughout this patent. For example, on the device side, one may attach a feedthrough capacitor, a filter circuit board or even a microelectronic circuit board. The thin sub-plate 410 could also be an alumina ceramic, which is co-fired against the pins 111 so the pins are held rigidly, but not necessarily hermetically. Alternatively, the thin sub-plate 410 may comprise: polyimide, polyamide, and polyamide-imide class of materials including Kapton, nylon, nylon 6, and nylon 6, 6,; the polyolefin class of materials including low-density polyethylene (LDPE), high-density polyethylene (HDPE), ultra-high molecular weight polyethylene (UHMWPE), polypropylene (PP), thermoplastic polyolefin (TPO), thermoplastic rubber or elastomer (TPR), and polyolefin alloys; the fluoropolymer class of materials including thermoplastic fluoropolymers, Teflon polytetrafluoroethylene (PTFE), TEFLON fluorinated ethylene propylene (FEP), Tefzel ethylene tetrafluoroethylene (ETFE), expanded polytetrafluroethylene (ePTFE), TEFLON perfluoroalkoxy (PFA) fluoroplastics, Halar ethylene chlorotrifluoroethylene (ECTFE); crosslinked polymers including polyethylene (XLPE) and irradiated polyvinylchloride (XLPVC); and polyvinyl chloride (PVC), polystyrene (PS), thermoplastic polyurethanes (TPU), and composites thereof. Additional material options include polyether ether ketone (PEEK), polyethylene terephthalate (PET), acrylic, Kynar polyvinylidene fluoride (PVDF), silicone rubber, Polyester Mylar, Kaladex polyethylene naphthalate (PEN), crosslinked polyalkene, and various other types of polymer materials. I addition to alumina, alternate ceramic material options include calcium oxide (CaO), porcelain, inert bioceramics or bioglasses, aluminosilicates, calcium-phosphate based ceramics, zirconia, calcium aluminum oxide, and electrically insulative silicon nitride. Referring once again to FIG. 49, one can see that the nail head end of leads 111 stands proud below the compression plate 410 so that, it can selectively compress conductive spheres 262', as indicated. This creates electrical conductivity in the z or longitudinal axis from each one of the insulator conductive vias, or otherwise known as conductive pathways, to each one of the respective body fluid side leadwires 111.

Referring once again to FIGS. 49 and 50, in FIG. 49, the force to compress the rigid holding plate 410 against the ACF film 212' to bond it and seat to the hermetic seal subassembly, in the case of FIG. 49, was shown coming from the top. In other words, from the rigid plate 410. FIG. 49 illustrates that the force can be applied from the other direction. In this case, a holding fixture (not shown) or a production fixture (not shown) would be drilled with the same number of holes as the pins 111. First, the rigid plate 410 would be placed directly aligned over the holes in the production fixture. Then each one of the nail headed leadwires 111 would be loaded into the fixture upside down. Tolerances are important, in that, they cannot be too loose, but they don't have to be tightly held within the fixture 410. The hermetic seal subassembly 120 consisting of the ferrule 112, the alumina insulator 160 and the co-sintered vias 185, 1986 have already been premanufactured in a separate manufacturing operation. This has been sintered into a solid monolithic and hermetic structure. So, the next step in the assembly process would be to place down an ACF film 212' over the nail headed end of all the pins 111 and then the hermetic seal subassembly would be brought down to the top and a force F, as indicated, would be applied to the device side of the hermetic seal thereby, compressing the ACL 212' against the rigid plate 410. As previously described, force and heat will be applied; first, to precure the ACL and then, a higher level of heat would be brought to finally cure it as an adhesive that would solidly bond the body fluid side surface of the hermetic seal subassembly 120 to the rigid plate 410. The advantage of the assembly process that's inverted, is this allows the rigid plate 410 to be significantly thinner. The reason for this is that it is fully mechanically supported by the production fixture (not shown) onto which it is seated.

Figure 53:
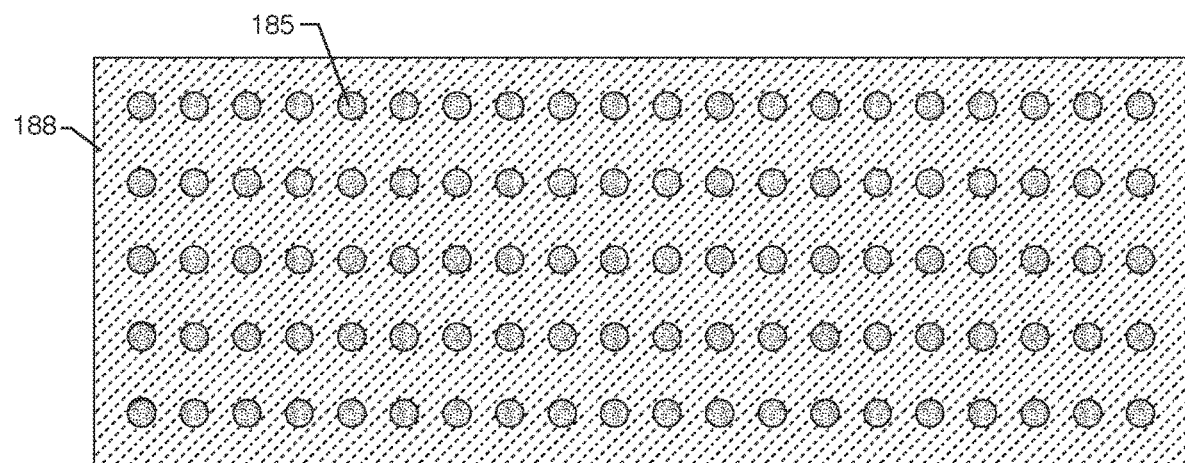
FIG. 53 is a top view of a rectangular hermetic feedthrough showing the possible plurality of electrical connections utilizing the structures of the present invention.
Figure 54:
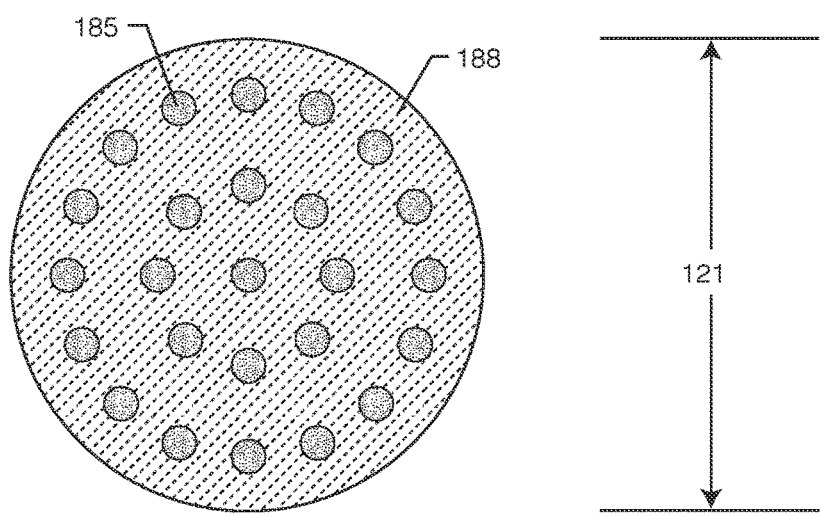
FIG. 54 is a top view of a round (discoidal) hermetic feedthrough showing the possible plurality of electrical connections utilizing the structures of the present invention.

FIGS. 53 and 54 are illustrations of top-down views of rectangular and round hermetic seal insulators simply indicating that in the present invention, high channel counts and high density are important, particularly for neurostimulators, such as retinal stimulators. FIG. 53 is a rectangular hermetic seal insulator whereas FIG. 54 is a round (discoidal) hermetic seal insulator having diameter 121. As previously mentioned, for a retinal stimulator there could even be hundreds, if not thousands, of such channels that are possible through the anisotropic conductive film structures of the present invention taught herein.

Figure 1:
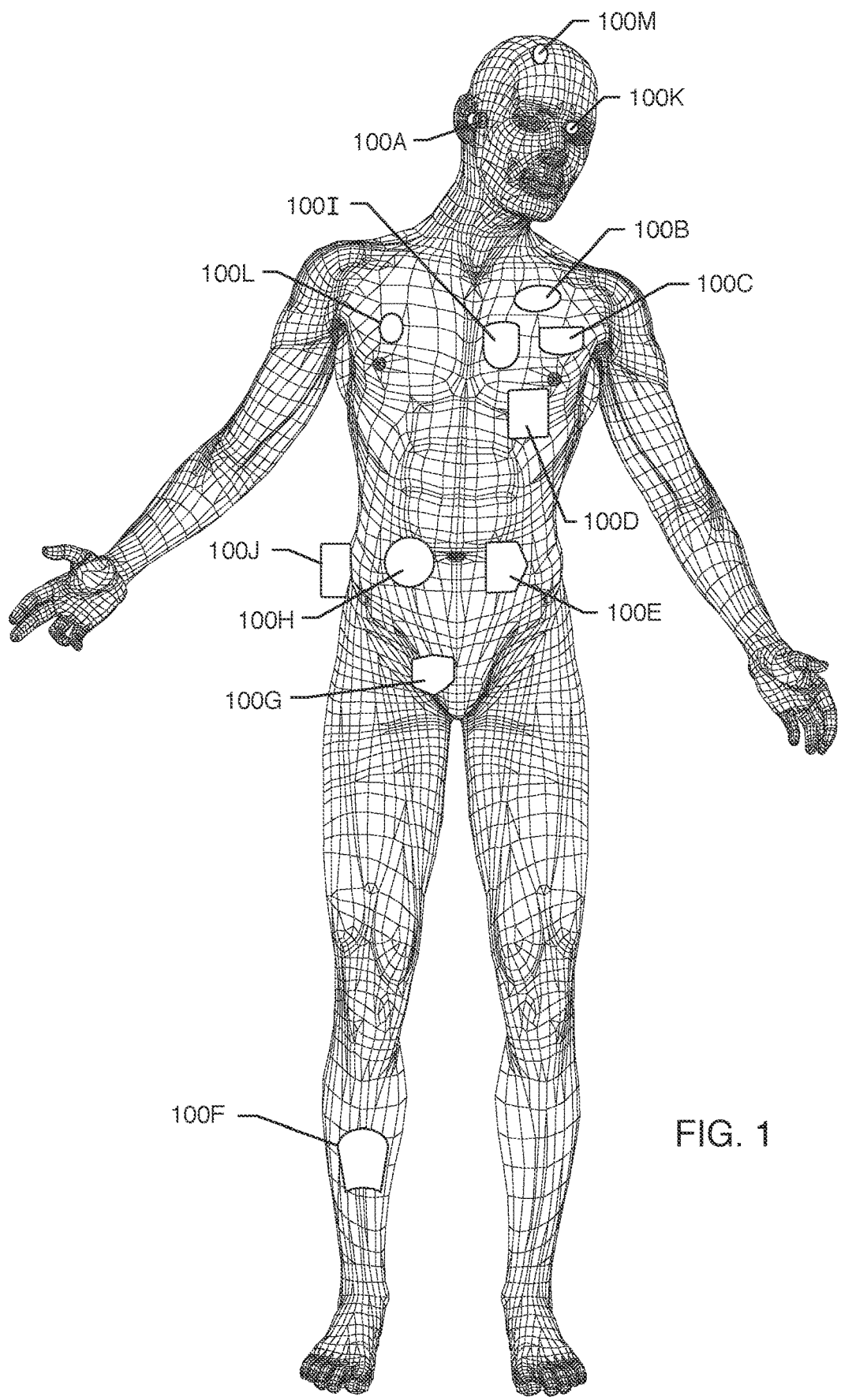
FIG. 1 is a wire-formed diagram of a generic human body showing a number of exemplary implantable medical devices.
Figure 2:
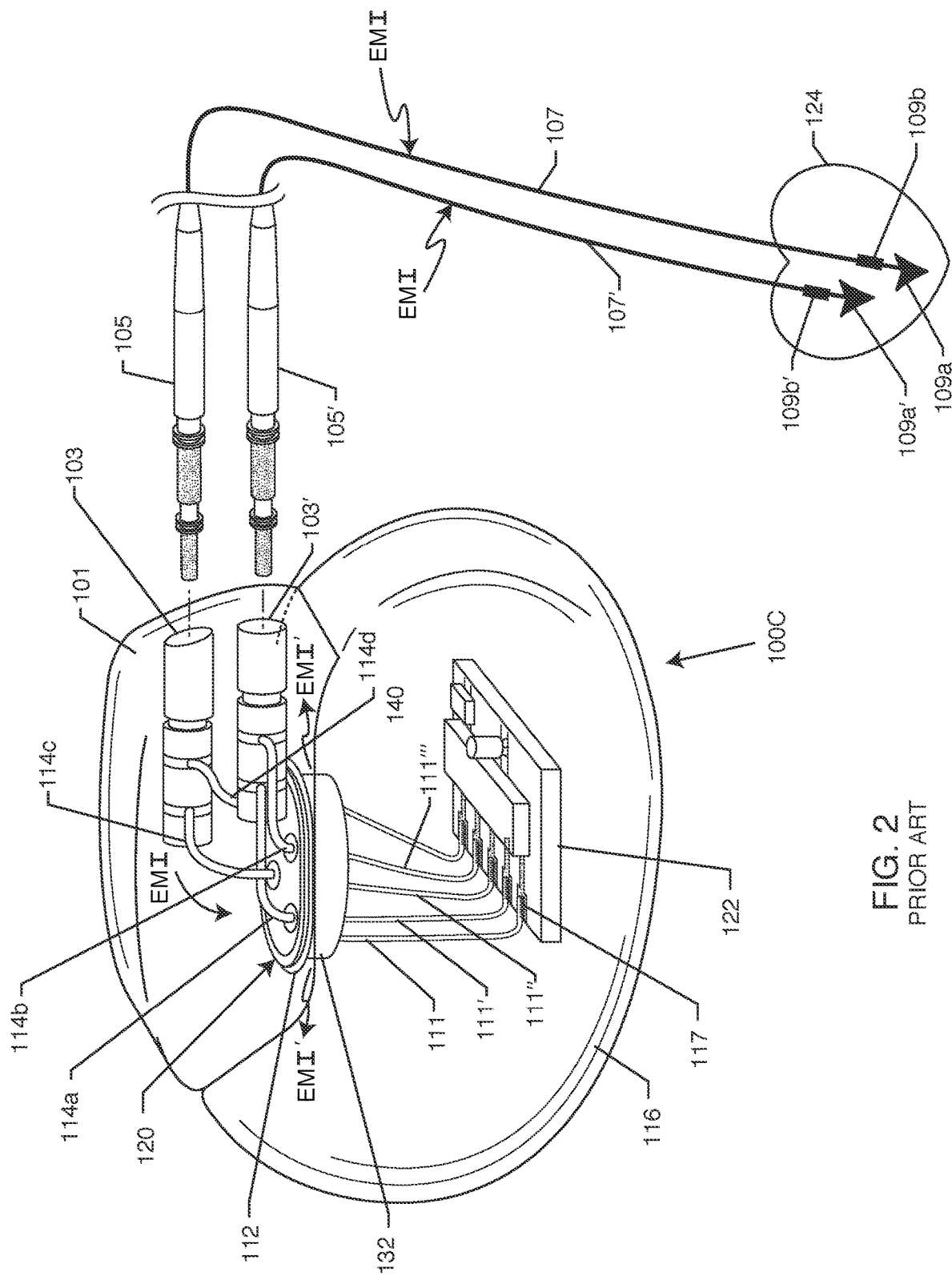
FIG. 2 is a side view of a prior art cardiac pacemaker.
Figure 3:
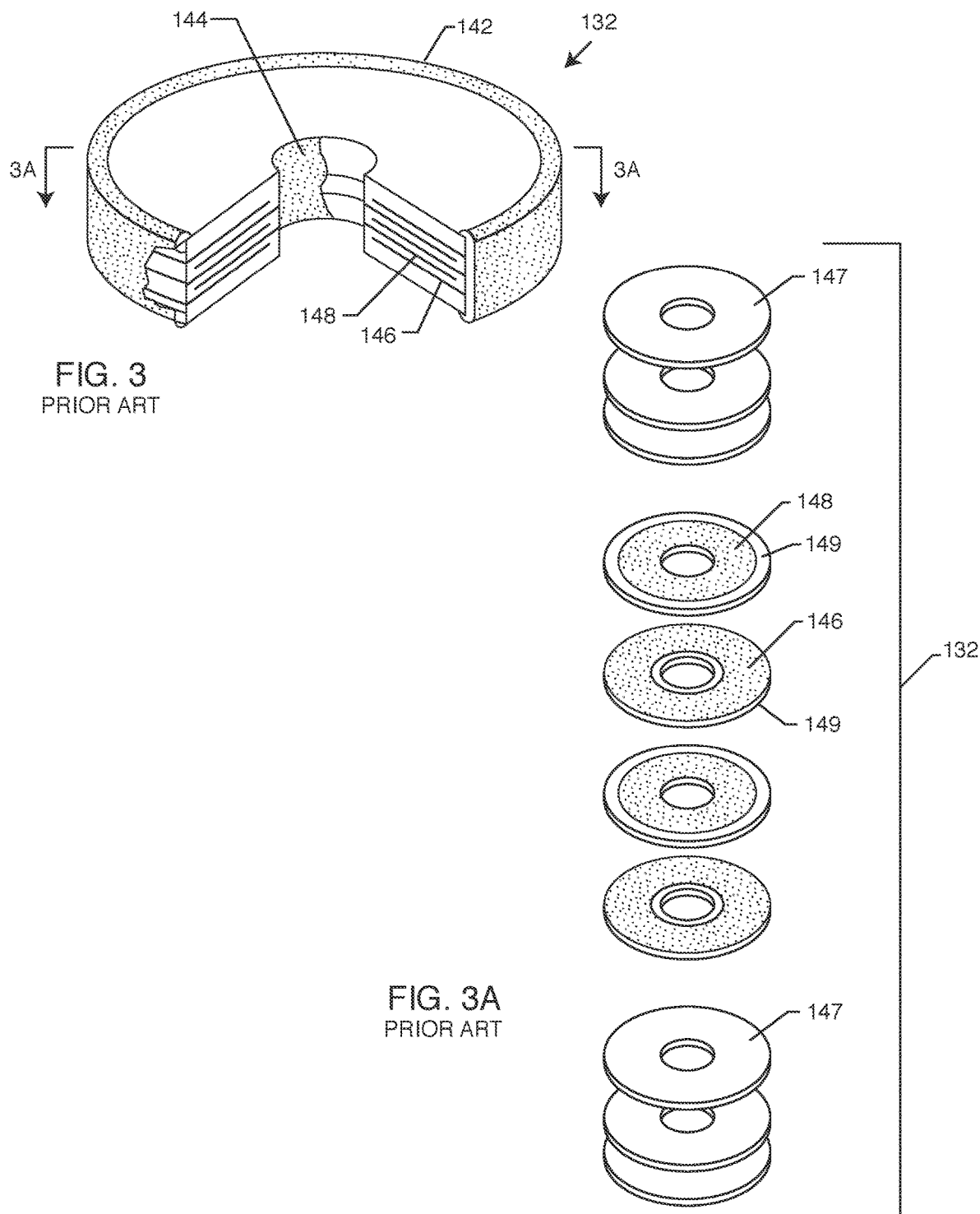
FIG. 3 is an isometric cut-away view of a prior art unipolar feedthrough capacitor.
Figure 4:
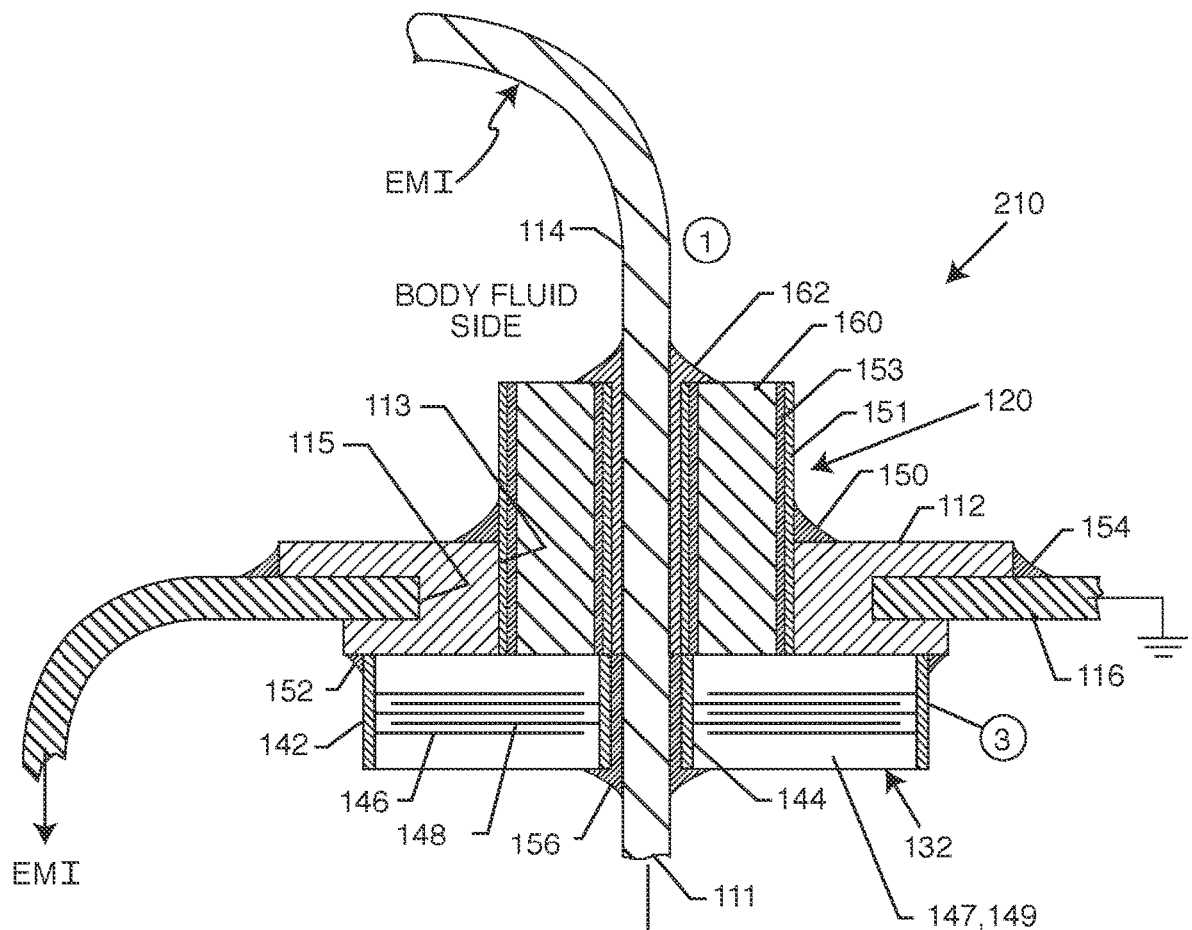
FIG. 4 is a sectional side view of a prior art hermetic feedthrough terminal.
Figure 4A:
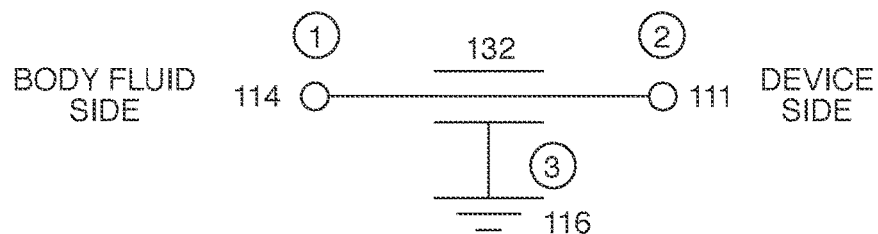
FIG. 4A is an electrical schematic of the structure of FIG. 4.
Figure 5:
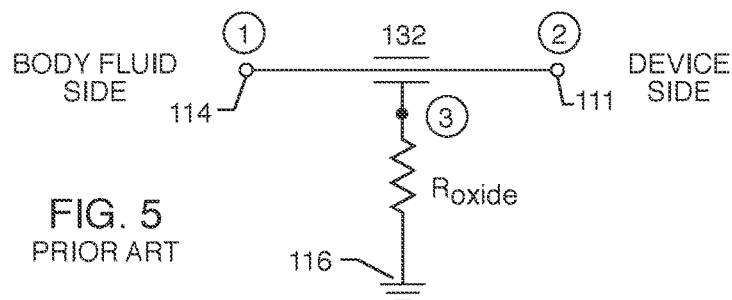
FIG. 5 is very similar to the schematic of FIG. 4A, except in this case, there is an oxide $R_{oxide}$.
Figure 6A:
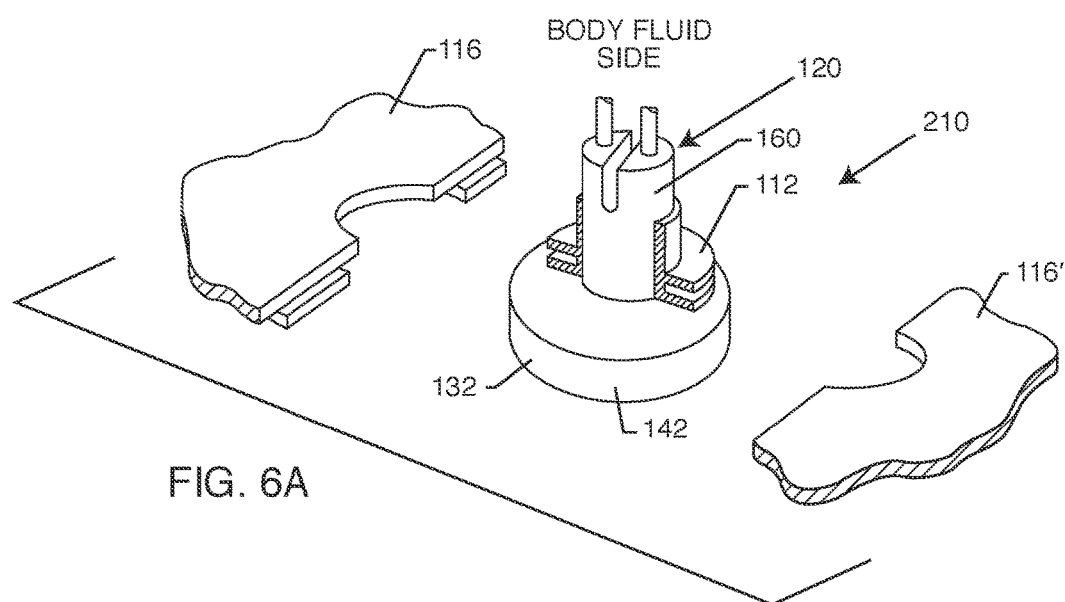
FIG. 6A is an isometric view taken from FIG. 21 of U.S. Pat. No. 5,333,095 where one can see that there is a feedthrough capacitor that is mounted onto a ferrule of a hermetic seal subassembly.
Figure 6B:
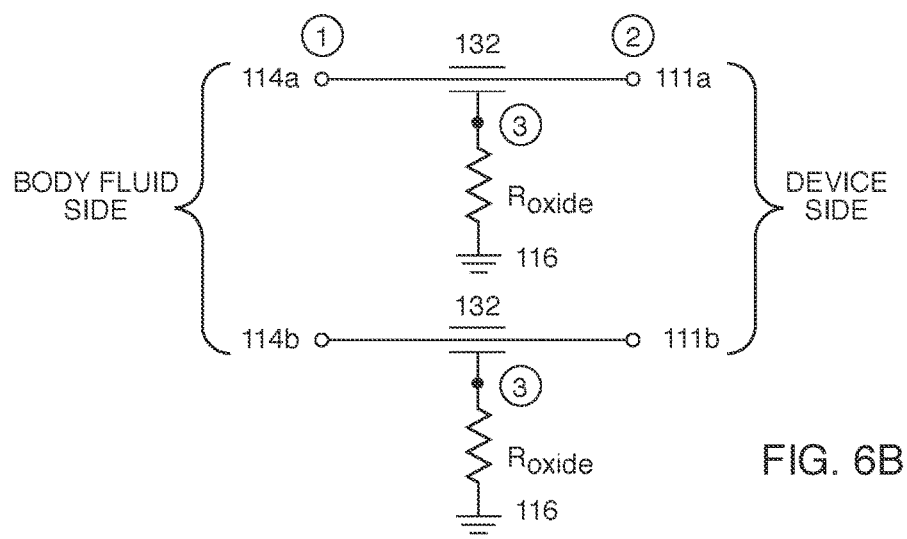
FIG. 6B illustrates the schematic of the bipolar feedthrough capacitor of FIG. 6A.
Figure 7A:
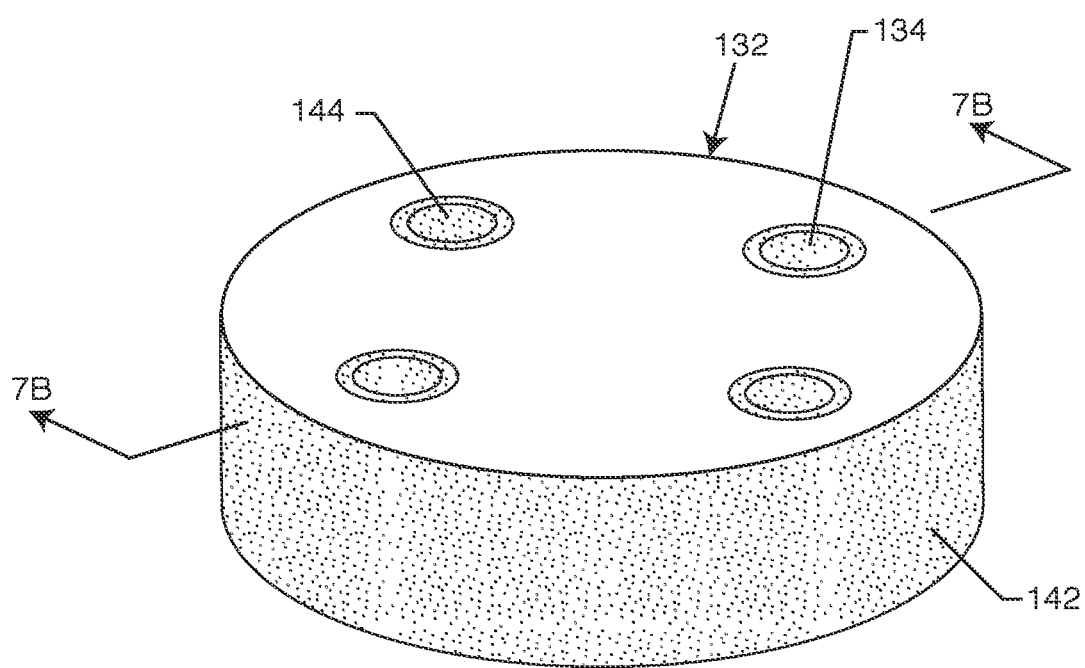
FIG. 7A is an isometric view illustrating a quad polar feedthrough capacitor.
Figure 7B:
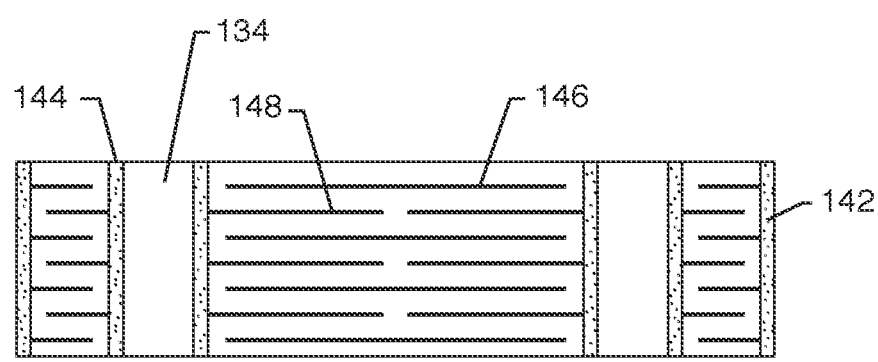
FIG. 7B is a sectional side view taken generally from FIG. 7B-7B from FIG. 7A, which illustrates the quad polar feedthrough capacitor of FIG. 7A.
Figure 8:
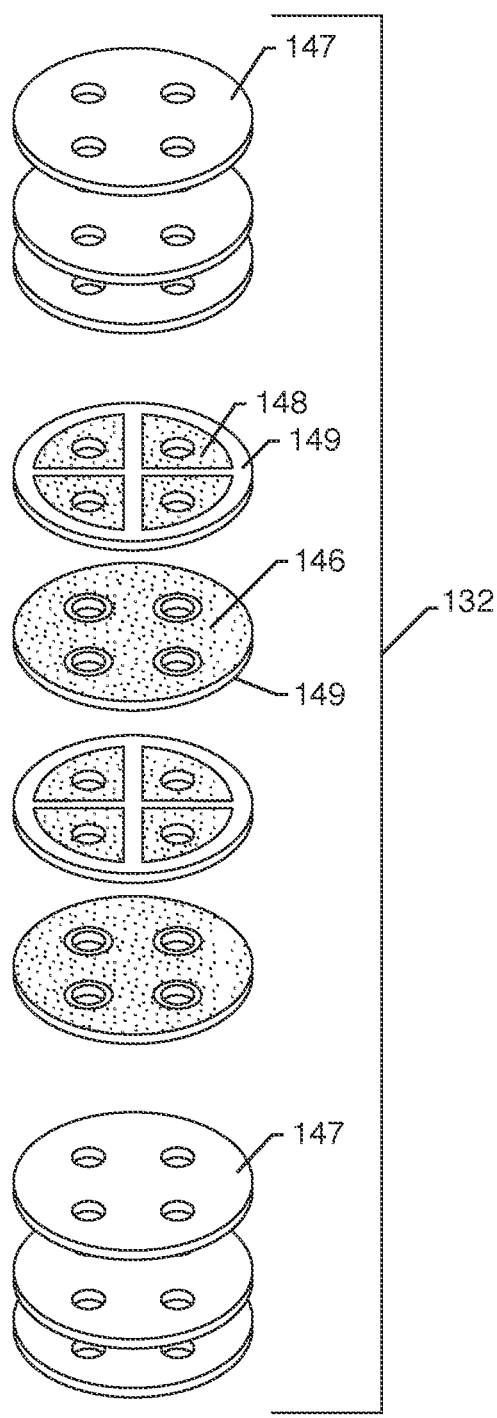
FIG. 8 is an exploded isometric view of the unipolar capacitor previously illustrated in FIGS. 7A and 7B.
Figure 9:
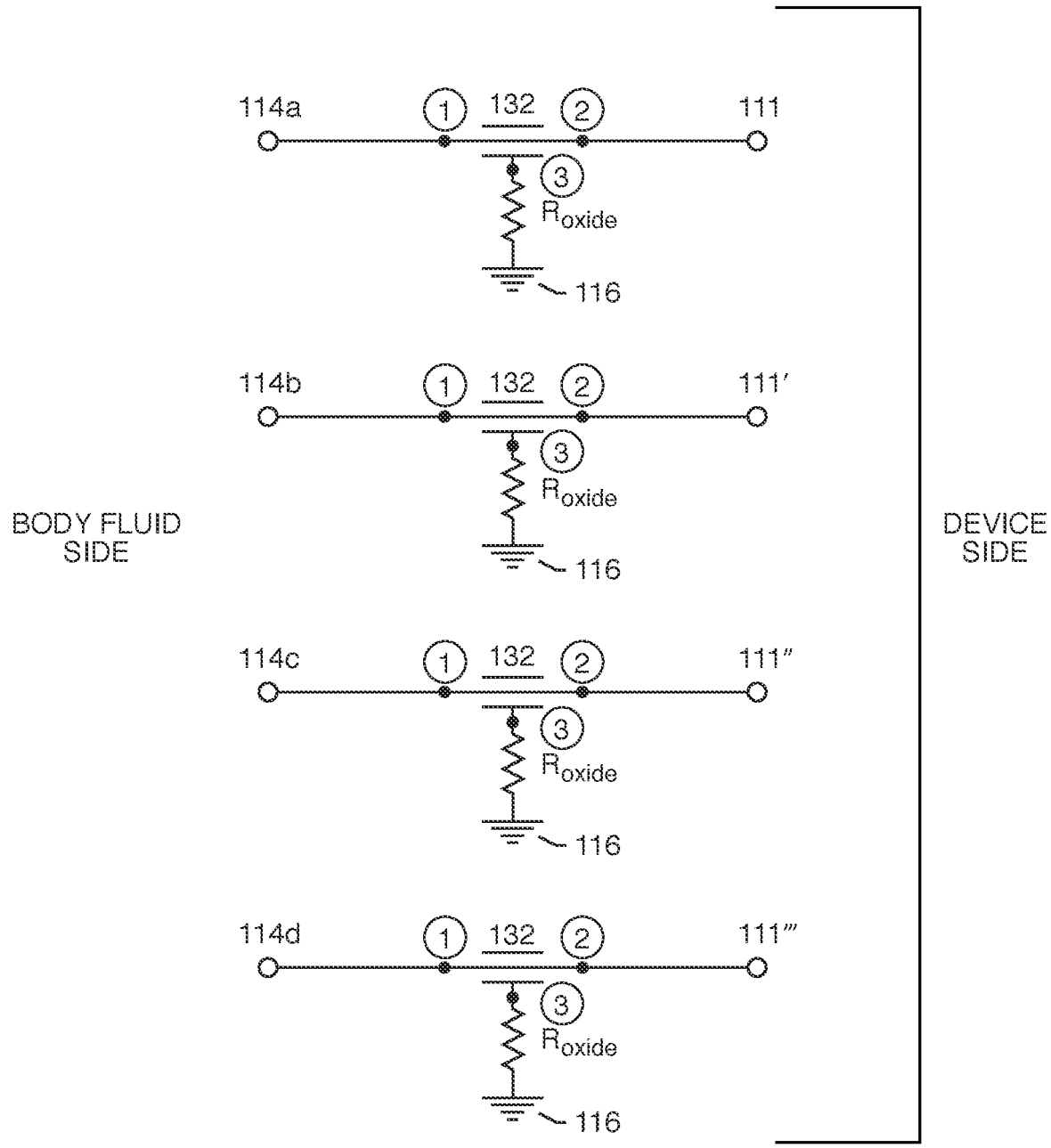
FIG. 9 is the electrical schematic drawing of the feedthrough capacitor of FIG. 8, but in this case, this is after the feedthrough capacitor has been installed to a hermetic seal ferrule and insulator with pins.
Figure 10:
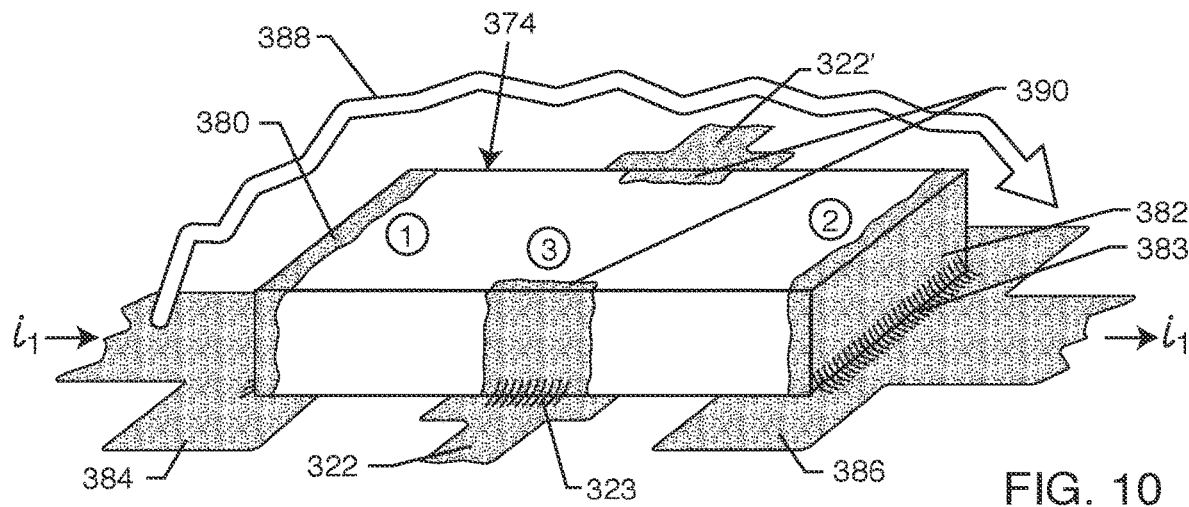
FIG. 10 is an isometric view illustrating a flat-thru capacitor.
Figure 10A:
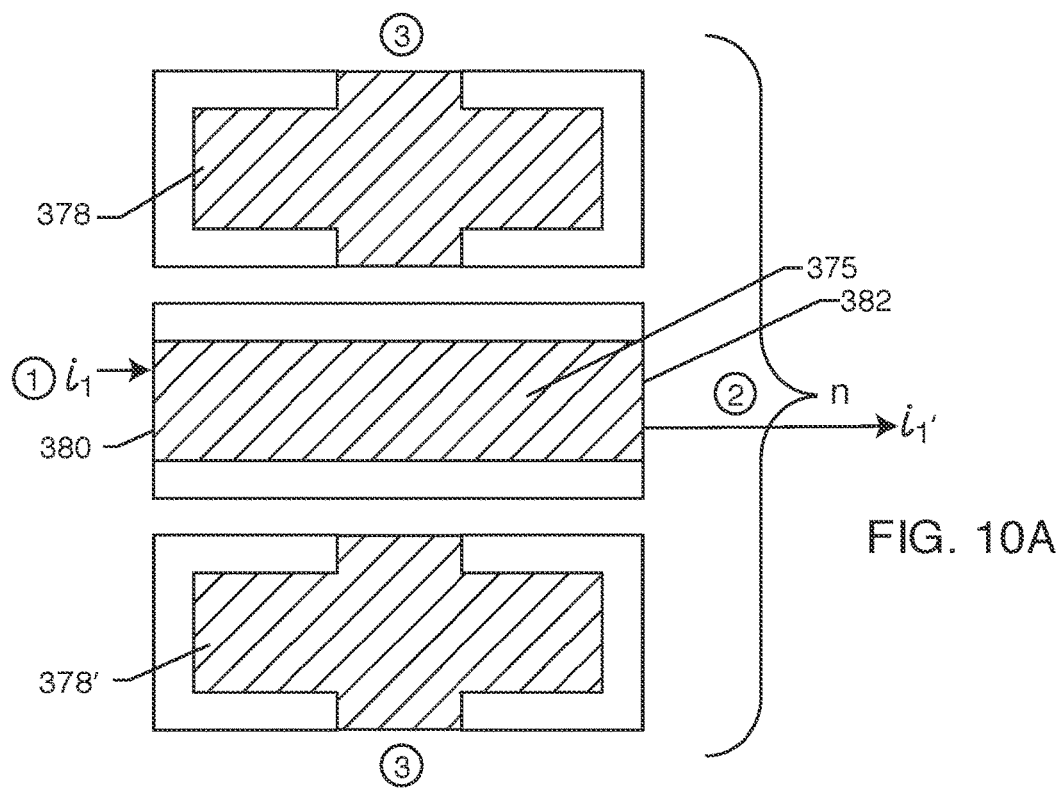
FIG. 10A is a sectional view through the structure of FIG. 10 illustrating the active and ground electrode plates.
Figure 15:
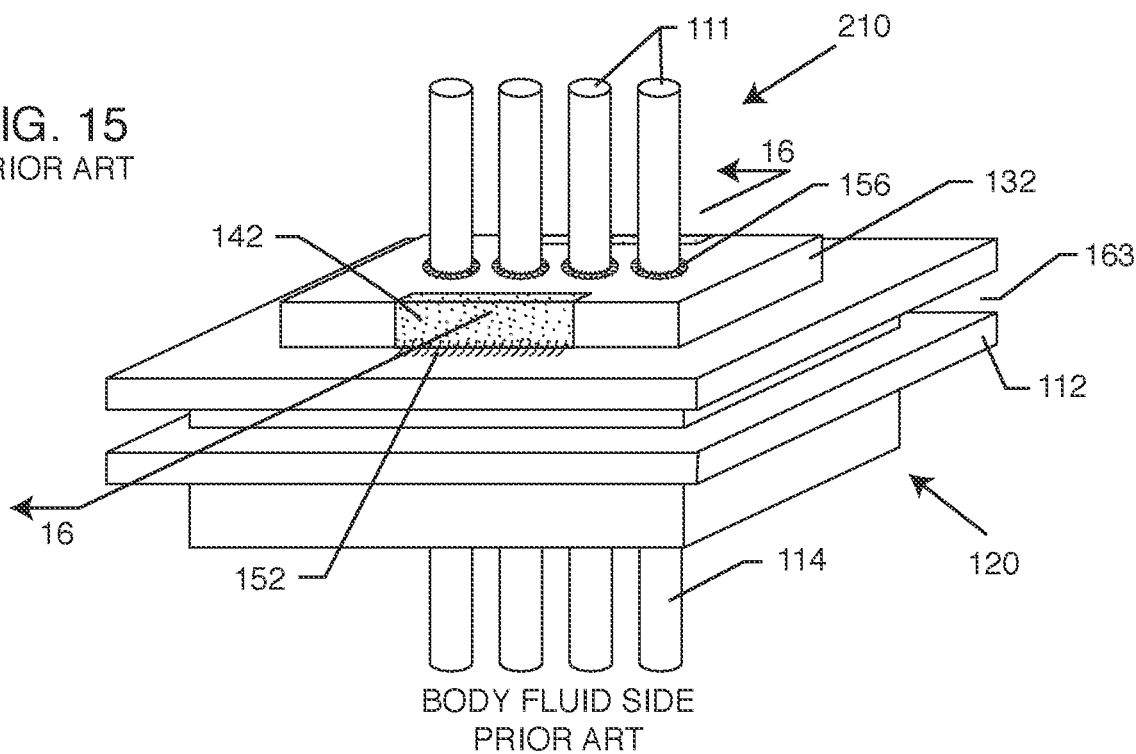
FIG. 15 is an isometric view illustrating the feedthrough capacitor installed to the hermetic seal assembly as previously described in FIGS. 11 and 12.
Figure 16:
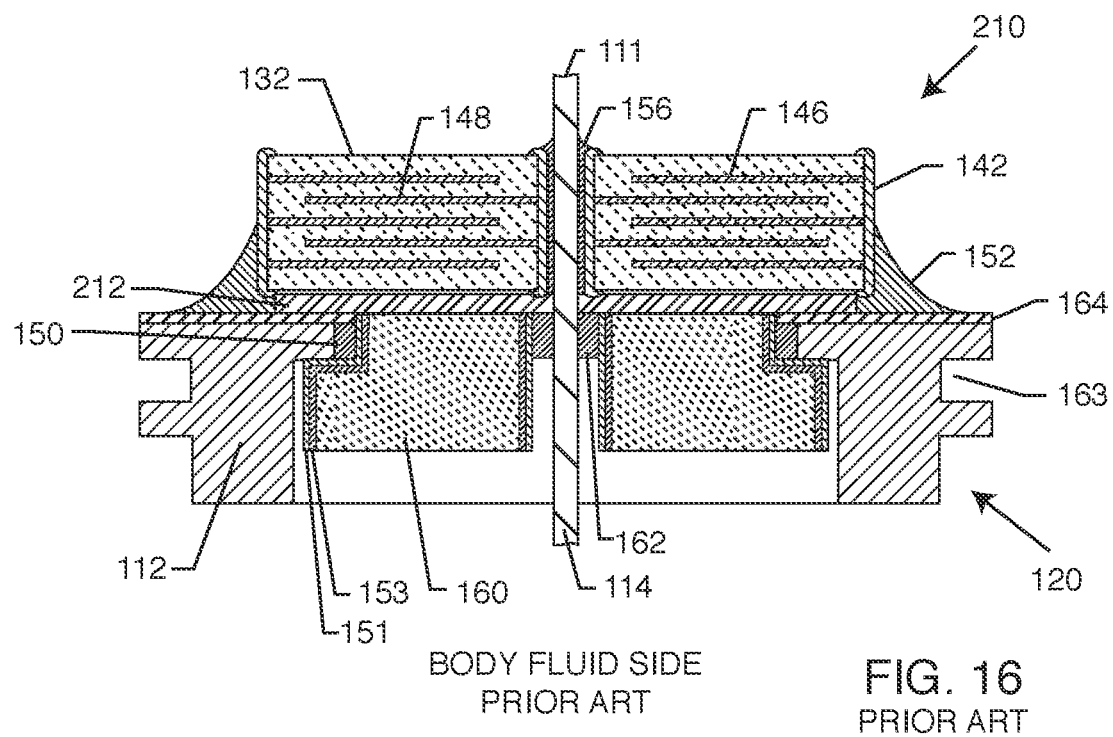
FIG. 16 is a side sectional view taken generally from section 16-16 from FIG. 15.
Figure 17:
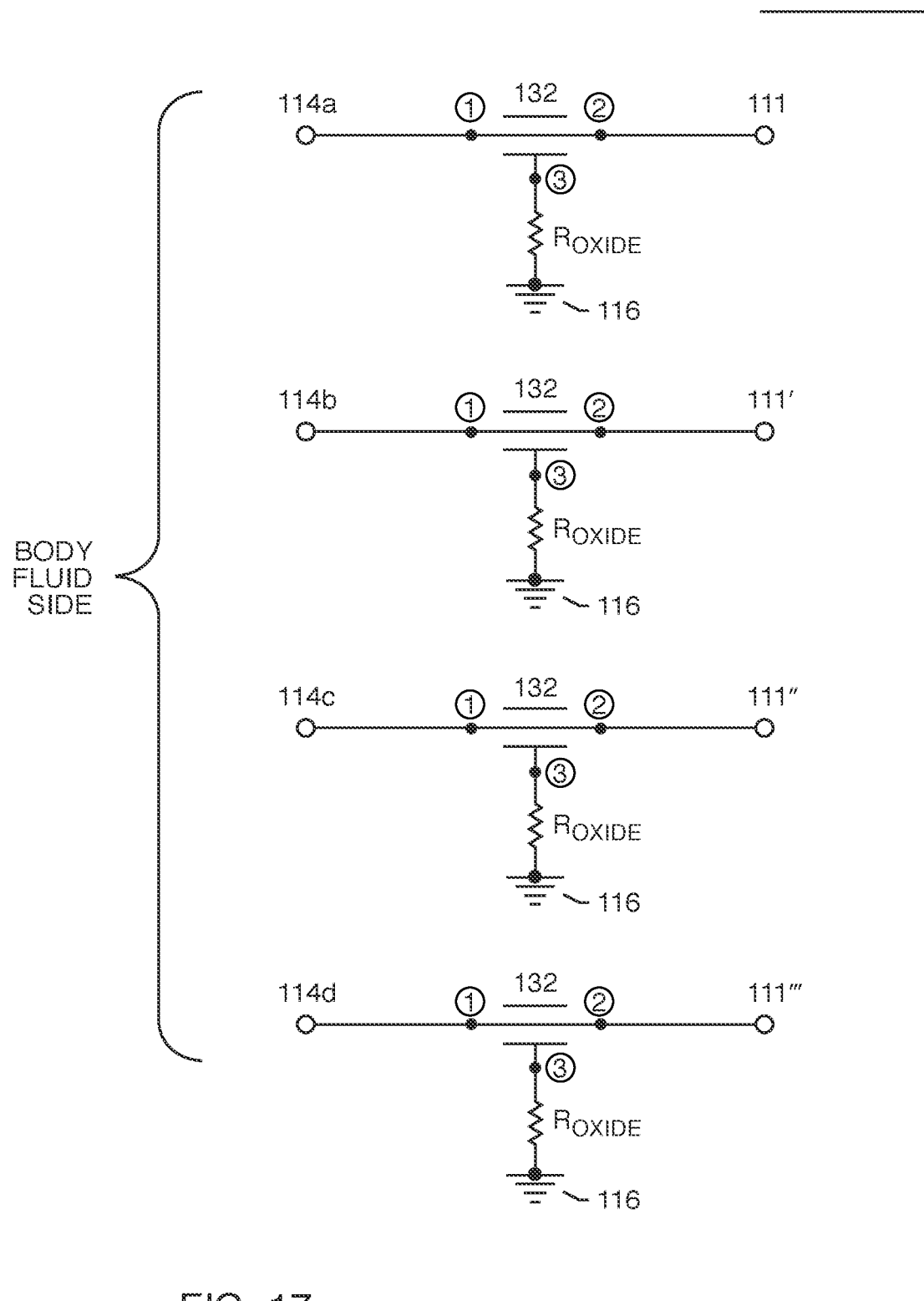
FIG. 17 is an electrical schematic diagram illustrating the undesirable presence of an oxide in the ground path of the quad polar feedthrough capacitor.

The inventors did a careful examination of the prior art and did find a case where ACF films are mentioned in conjunction with a hermetic seal for an implanted medical device. This is in U.S. Pat. No. 9,174,047, the contents of which are herein incorporated fully by reference. The following is quoted from the '047 patent from column 6, lines 28 through 42 and reads on FIG. 4B, and is as follows: "On the interior side of the electrical feedthrough (405), connections (407) may be made between the hybrid circuit (422) and the feedthrough (405). According to one illustrative embodiment, the hybrid (422) is attached to the underlying electrical feedthrough (405) using a blind attachment technique. Blind attachment refers to situations where only one side of a work piece is accessible for component assembly and making electrical connections. In this case, the hybrid circuit (422) may entirely cover the electrical feedthrough (405), rendering it not visible during the attachment process. The blind attachment may be done using a variety of methods, including, but not limited to the anisotropic conductive film, anisotropic conductive paste, conductive epoxy, conductive silicone, solder, ball grid array and other compatible approaches."

The problem with this kind of a laundry list spanning ACF films, solder and to other compatible approaches is that none of them are enabled. For example, nowhere in the '047 patent is the creation of proud flat surfaces done either on the hermetic seal side or on the circuit board side, that would lead to a reliable compression of conductive particles in an ACF paste or film. This contrasts with the present invention which goes to a great deal of effort to create nail heads or very proud flat surfaces to reliably compress particles in an ACF film. In addition, the '047 patent does not discuss primary filtering or feedthrough capacitor at all for an active implantable medical device. ACF films have been used many times to connect circuit boards to flexible circuit boards or to LCD screens and the like, however, no one has ever contemplated using ACF films to make a connection between a feedthrough capacitor and an adjacent hermetic feedthrough terminal for an AIMD. Importantly, feedthrough capacitors are disposed directly at the point of leadwire ingress to an AIMD to divert dangerous high-frequency energy immediately to the housing before it can enter and re-radiate to sensitive electronics. In addition, there is no mention whatsoever in the '047 patent (or any other prior art that the inventors can find) that contemplate the use of a biocompatible ACF film on the body fluid side of a hermetic insulator for an AIMD. It is well known that even if the AIMD has a header block, such as cardiac pacemaker, that the header block, which may be a plastic, such as Tecothane®, does not prevent over time the entry of body fluids due to a process known as bulk permeability. To understand bulk permeability, one needs to understand the military and space industry has outlawed any adjunct salient over a hermetic seal. A true hermetic seal is generally, in this context, a gold brazed alumina ceramic seal capable of leak rates greater than $1 \times 10-7$ std. cc He/s. To understand bulk permeability, one need look no further than the antique glass fishing floats that are sometimes found hanging on nets, for example outside a restaurant in Cape Cod. Close examination reveals that sometimes these so-called solid hollow glass balls are half full of water or more. That water, over time, enters through changes in temperature and humidity and over time, the water vapor passes right through the glass and ends up condensing on the inside as water. Such an occurrence would be a disaster for the sensitive electronic circuits of an active implantable medical device. What this means is that any electrical connection on the body fluid side of a hermetic terminal for an AIMD must be completely biocompatible, biostable, and non-toxic. It must be assumed that over time, water will reach this area since it is not inside a hermetically sealed area. Therefore, only very special materials as taught herein, in compositions for ACF films can be used. In summary, the '047 patent teaches nothing about using nail heads through circuit boards to create continuous electrical paths and proud surfaces nor does it teach anything about the mounting of a feedthrough capacitor, nor does it teach anything about biocompatibility of an ACF film.

Figure 55:
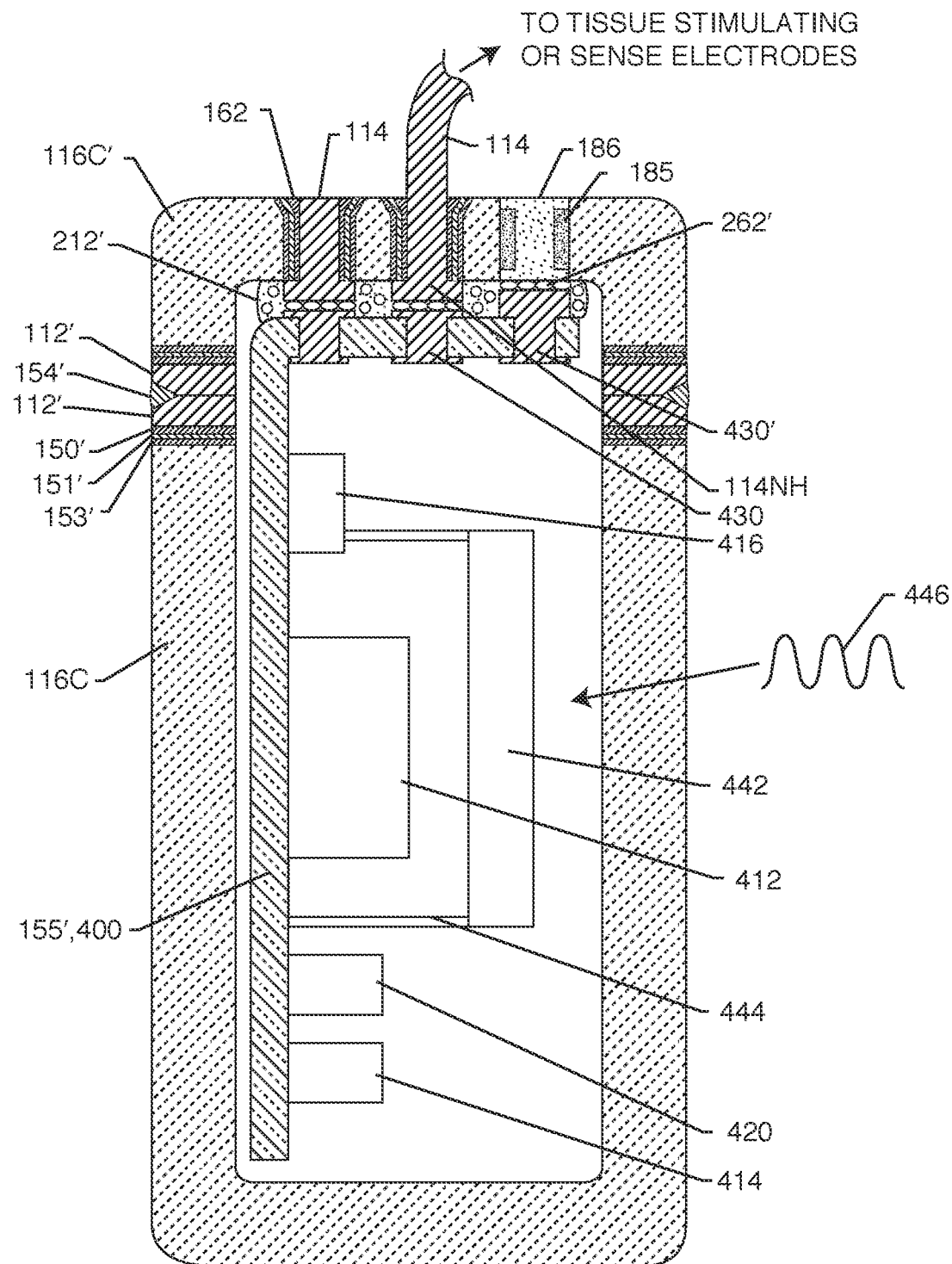
FIG. 55 is a side sectional view of another exemplary embodiment of the present invention having a ceramic AIMD housing showing nail head leads and composite conductive fills attaching to a circuit board by the use of the ACL.

FIG. 55 is a cross-sectional view through a ceramic cased AIMD. In this case, the entire AIMD housing comprises a ceramic base 116C and a ceramic lid 116C'. In general, the ceramic could comprise a substantially pure alumina ceramic (Al$_2$O$_3$). The ceramic lid 116C' and the ceramic base 116C are treated with both adhesion and wetting layers by sputtering 151' and 153'. Then there is a gold braze 150', which attaches a substantially pure titanium ring 112'. In a similar manner, the substantially pure ceramic lid 116C' is also prepared by adhesion and wetting layers such that a gold braze attaches a second titanium ring 112'. As used herein, the term "titanium ring" could include round rings, rectangular rings, oval rings, or any other shape to conform to any shape of the ceramic AIMD housing halves 116C and 116C'. Likewise, the shape of the lid and the shape of the housing 116C' and 116C can be rectangular, square, round, oval, irregular, partially curved or any shape required.

Before the ceramic lid 116C' is laser welded 154' to the ceramic base 116C, an electronic package is first manufactured and installed, like a ship in a bottle. Referring once again to FIG. 55, one can see that there is an L-shaped circuit board 155', 400. This circuit board can contain biological sensing circuits, therapeutic delivery circuits, memory circuits, monitoring circuits, programming circuits or even telemetry circuits. In general, microprocessor 412 is shown attached to the circuit board and other electronic components, such as 414, 416 and 420. These are just general representations that the circuit board could have a plurality of electronic components and microcircuits attached to it. For simplicity, circuit board external and/or internal active and/or ground traces or active and/or ground planes are not shown but could be used.

In this case, the circuit board has an energy transfer module 442, as indicated. This can be an inductive loop with many turns of wire, or a tuned LC circuit or the like. Its purpose is to capture electromagnetic energy 446 from an external RF power transmitting source, such that this energy can be captured by the AIMD of FIG. 55 so that it can be stored for a short period of time in a storage capacitor that is located on the circuit board. In this way, the AIMD or neurostimulator of FIG. 55 can capture energy and deliver it to appropriate human tissues without the need to have its own internal power source, such as a primary or secondary battery. This transfer of energy 446 is a main reason why at least a substantial part of the AIMD housing of FIG. 55 has to be transparent to electromagnetic fields. Ideal transparent materials include ceramics, glass-ceramics, and glasses. A ceramic cased AIMD is more thoroughly described in U.S. Pat. No. 4,991,582, the contents of which are incorporated herein fully by reference.

Referring once again to FIG. 55, in the L-shaped portion of the circuit board, the circuit board is first attached to the lid assembly 116C'. This assembly is facilitated with the novel nail heads 430 in the circuit board that fill the circuit board via holes along with body fluid side nail head leadwires 114, 114NH. These nail-headed leadwires 114, 114NH can extend to tissue stimulating or sense electrodes (not shown).

On the right-hand side of FIG. 55, a co-sintered via consisting of a CRMC material 185 and a substantially pure platinum paste 186 is shown. In this case, the circuit board via nail hole has been made thicker, such that the ACL conductive particles 262' are properly compressed in accordance with the present invention. As previously described in the present invention, a force would be disposed against the short L-shaped portion of the circuit board against the ACL 212' and against the nail head structure, such that, the ACL conductive particles 262' would be selectively compressed in the areas where Z axis conductivity is required, but not compressed in the X and Y axis, such that adjacent channels are insulated from each other.

As previously mentioned, this is a ship-in-the-bottle kind of a construction where the assembly work is done first, so that, final testing of the circuit board and all of its components, including high reliability procedures, such as elevated temperature burn-in, could be performed. It is at this time, that the entire circuit board and all of its components are slipped down inside the ceramic housing 116C until the opposed weld rings are seated against each other. At this point, the inside of the unit is evacuated in a vacuum and then backfilled with an inert gas, such as nitrogen with a trace of helium for helium leak detection. A continuous laser weld 154' is made all the way around the seam between the upper and lower titanium weld rings, which mechanically attaches the upper lid 116C' to the bottom housing 116C and therefore, also hermetically seals it.

Figure 56:
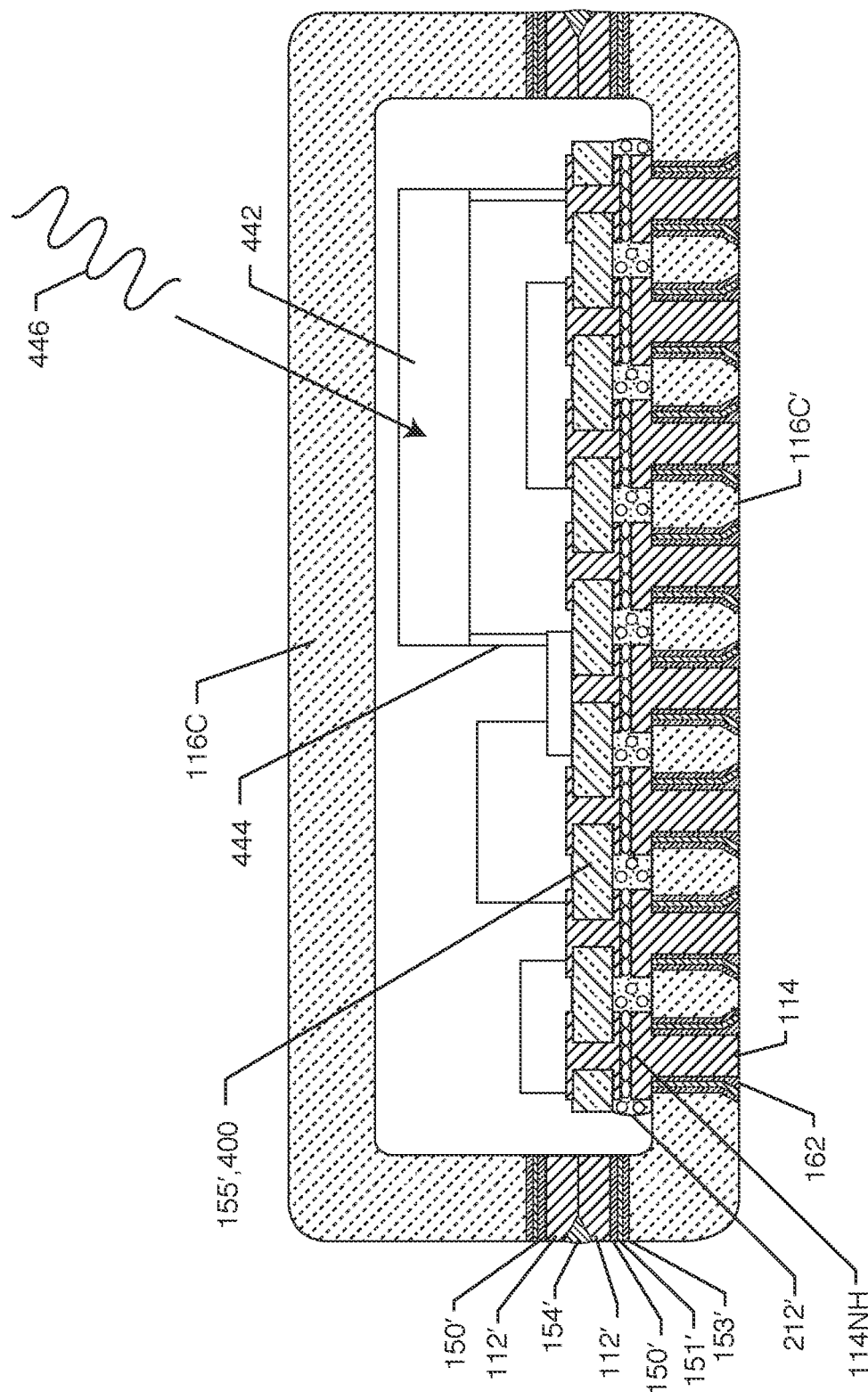
FIG. 56 is a side sectional view of another exemplary embodiment of the present invention similar to FIG. 55, now showing a different AIMD housing design.

FIG. 56 is very similar to FIG. 55, except the orientation of the circuit board is disposed in an opposite axis so that the circuit board is lying flat against ACL (ACF) 212'. In this case, there is still a ceramic base 116C' and a ceramic lid 116C. As previously described in FIG. 55, a circuit board 115', 400 is disposed against the ACL 212' which is disposed in a sandwich manner against the nail headed vias 114NH, which are embedded within the base structure 116C'. In this case, these nail-headed leadwires are gold brazed to adhesion and wetting layers, as previously described. The circuit board is pressed down against the ACL 212', and at the same time elevated temperature is applied to cure the ACL.

Similar to FIG. 55, FIG. 56 shows an all-ceramic housing 116C and 116C'. It will be appreciated that it is also designed to capture energy from an outside source 446, which can couple inductively or through resonant circuitry to power the AIMD electronics. Alternatively, the energy-harvesting module 442 can be eliminated in either FIG. 55 or FIG. 56 and be replaced by a primary or secondary battery.

Referring once again to FIG. 56, the lower assembly 116C' with its hermetic seals could be replaced with a titanium ferrule supporting an insulator, as previously described throughout the other figures of this application, such as in FIG. 47. The ferrule structure 112 would be designed to be laser welded at the exact same point 154' as described to mate with the ceramic lid titanium weld ring. This mating would also provide a strong mechanical and hermetic seal. It will be appreciated that the titanium weld rings described above are just examples and any biocompatible and weldable material could be used such as niobium, tantalum, stainless steel alloys, cobalt-chromium alloys, titanium alloys and the like.

The headings (such as "Introduction" and "Summary") and sub-headings used herein are intended only for general organization of topics within the present disclosure and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

As used herein, ACL is an acronym for an Anisotropic Conductive Layer. Anisotropic Conductive Adhesive (ACA), Anisotropic Conductive Film (ACF), Anisotropic Conductive Paste (ACP), anisotropic conductive tape, and anisotropic conductive epoxy are all types of ACL. Throughout this patent specification, ACF or Anisotropic Conductive Film is used as an example; however, it is understood that, anywhere ACF or Anisotropic Conductive Film is specified or described, any type of ACL can also be used. Additionally, it is contemplated that any type of ACL may be used alone or in combination with one or more other or different ACL type.

"A" and "an" as used herein indicate "at least one" of the item is present, which also includes the possibility of a plurality of such items being present. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

What is claimed is:

1. An implantable medical device (IMD), the IMD comprising:
   a) a ceramic base comprising a sidewall defining an open space and extending to a base annular edge surrounding a base open end;
   b) a ceramic lid closing the open end of the ceramic base, the lid extending to a lid annular edge meeting a lid device side spaced from a lid body fluid side, wherein at least a lid first conductive pathway extends to spaced apart lid first conductive pathway device and body fluid side ends, and a lid second conductive pathway extends to spaced apart lid second conductive pathway device and body fluid side ends;
   c) a circuit board residing in the interior space of the ceramic base closed by the lid, the circuit board extending to spaced apart circuit board first and second sides, wherein a circuit board first conductive pathway extends to spaced apart circuit board first conductive pathway first and second ends adjacent to the respective circuit board first and second sides, and a circuit board second conductive pathway extends to spaced apart circuit board second conductive pathway first and second ends adjacent to the respective circuit board first and second sides;
   d) at least one electronic component supported by the circuit board, the electronic component having a first terminal spaced from a second terminal, wherein the circuit board first and second conductive pathway second ends are electrically connected to the respective first and second terminals of the at least one electronic component; and
   e) an anisotropic conductive layer disposed between the circuit board first side and the device side of the ceramic lid, the anisotropic conductive layer comprising an electrically insulative matrix supporting a plurality of electrically conductive particles, wherein the anisotropic conductive layer comprises:
      i) a first thickness that is longitudinally aligned with the lid first conductive pathway device side end and the circuit board first conductive pathway first end adjacent to the circuit board first side, wherein the electrically conductive matrix of the anisotropic conductive layer residing in the first thickness has at least a first one of the plurality of electrically conductive particles in electrical contact with the lid first conductive pathway device side end and the circuit board first conductive pathway first end to thereby provide electrical continuity from the lid first conductive pathway body fluid side end to the circuit board first conductive pathway second end electrically connected to the first terminal of the at least one electronic component;
      ii) a second thickness that is longitudinally aligned with the lid second conductive pathway device side end and the circuit board second conductive pathway first end adjacent to the circuit board first side, wherein the electrically conductive matrix of the anisotropic conductive layer residing in the second thickness has at least a second one of the plurality of electrically conductive particles in electrical contact with the lid second conductive pathway device side end and the circuit board second conductive pathway first end to thereby provide electrical continuity from the lid second conductive pathway body fluid side end to the circuit board second conductive pathway second end electrically connected to the second terminal of the at least one electronic component; and
      iii) a third thickness that is greater than the first and second thicknesses where the lid and circuit board first conductive pathways are not longitudinally aligned and where the lid and circuit board second conductive pathways are not longitudinally aligned, wherein, even though the electrically conductive matrix supporting the plurality of electrically conductive particles resides in the third thickness, a third one of the plurality of electrically conductive particles is not in electrical contact with either of the lid first conductive pathway and the circuit board first conductive pathway, and with either of the lid second conductive pathway and the circuit board second conductive pathway, iv) wherein the third, greater thickness of the anisotropic conductive layer electrically isolates at least the first and second ones of the plurality of electrically conductive particles from each other.

2. The IMD of claim 1, wherein at least one of the lid first conductive pathway device side end and the circuit board first conductive pathway first side end is proud of the respective lid device side and the circuit board first side, and wherein the first thickness of the anisotropic conductive layer is longitudinally aligned with the at least one proud lid first conductive pathway device side end and the circuit board first conductive pathway first side end, and wherein the third, greater thickness of the anisotropic conductive layer resides where the at least one proud lid first conductive pathway device side end and the circuit board first conductive pathway first side end are not longitudinally aligned.

3. The IMD of claim 1, wherein the lid first and second conductive pathway device side ends and the circuit board first and second conductive pathways first and second side ends are proud of the respective lid device side end and the circuit board first side.

4. The IMD of claim 1, wherein:
a) a first plurality of longitudinally aligned electrically conductive particles are in contact with each other and with the lid first conductive pathway device side end and the circuit board first conductive pathway first side end in the first thickness of the anisotropic conductive layer to thereby provide electrical continuity from the lid first conductive pathway body fluid side end to the circuit board first conductive pathway second side end electrically connected to the first terminal of the at least one electronic component;
b) a second plurality of longitudinally aligned electrically conductive particles are in contact with each other and with the lid second conductive pathway device side end and the circuit board second conductive pathway first side end in the second thickness of the anisotropic conductive layer to thereby provide electrical continuity from the lid second conductive pathway body fluid side end to the circuit board second conductive pathway second side end electrically connected to the second terminal of the at least one electronic component; and
c) a third plurality of electrically conductive particles reside in the third thickness of the anisotropic conductive layer, but they are not in electrical continuity with either the lid first conductive pathway device side end and the circuit board first conductive pathway first side end in the first thickness or with the lid second conductive pathway device side end and the circuit board second conductive pathway first end.

5. The IMD of claim 1, wherein the electrically conductive particles are either compressible or rigid.

6. The IMD of claim 1, wherein the anisotropic conductive layer is selected from the group of a film, a paste, a tape, and an adhesive.

7. The IMD of claim 1, wherein the electrically conductive particles of the anisotropic conductive layer are selected from metallic particles, metal-coated particles, electrically conductive composite particles and electrically conductive coated polymer, glass, glass-ceramic, and ceramic particles.

8. The IMD of claim 1, wherein the lid first and second conductive pathways, and the circuit board first and second conductive pathways are individually comprised of a leadwire, an eyelet, and a substantially pure platinum at least partially filling the respective lid and circuit board first and second passageways.

9. The IMD of claim 1, wherein the lid first and second conductive pathways are individually a first and a second nail head leadwire that is proud of the lid device side.

10. The IMD of claim 1, wherein the lid first and second conductive pathways, and the circuit board first and second conductive pathways are individually comprised of a leadwire, an eyelet, and a substantially pure platinum at least partially filling the respective lid and circuit board first and second passageways.

11. The IMD of claim 1, wherein:
a) a base metallization is contacted the base annular edge and a base titanium ring is brazed to the base metallization opposite the ceramic base;
b) a lid metallization is contacted the lid annular edge and a lid titanium ring is brazed to the lid metallization opposite the lid; and
c) a weld secures the base titanium ring to the lid titanium ring to thereby connect the lid to the base to close the open end of the ceramic base.

12. The IMD of claim 11, wherein the base and lid metallizations comprise a wetting layer contacted to the base annular edge and the lid annular edge, and a respective adhesion layer contacted to the wetting layer.

13. The IMD of claim 1, wherein:
a) the ceramic lid comprises an alumina ceramic; and
b) the lid first and second conductive pathways individually comprise a composite fill characterized as having been co-sintered with the alumina ceramic or a substantially pure platinum fill characterized as having been co-sintered with the alumina ceramic.

14. The IMD of claim 13, wherein the composite fill comprises a ceramic reinforced metal composite comprising a mixture of alumina and platinum surrounding a substantially pure platinum fill or a metallic wire.

15. The IMD of claim 1, wherein the at least one electronic component supported by the circuit board is selected from a biological sensing circuit, a therapeutic delivery circuit, a memory circuit, a monitoring circuit, a programming circuit, and a telemetry circuit.

16. The IMD of claim 1, wherein, in addition to the at least one electronic component, the circuit board supports an energy transfer module connected to a storage capacitor, the energy transfer module being configured to capture electromagnetic energy from an external RF power transmitting source to power the at least one electronic component.

17. The IMD of claim 1, wherein, in addition to the at least one electronic component, the circuit board supports a primary or secondary battery which is configured to power the at least one electronic component.

18. The IMD of claim 1, wherein the at least one electronic component is supported on the circuit board first side, the circuit board second side or it is embedded in the circuit board.

19. An implantable medical device (IMD), the IMD comprising:
a) a ceramic base comprising a sidewall defining an open space and extending to a base annular edge surrounding a base open end;
b) a feedthrough comprising:
i) a metallic ferrule having a ferrule opening extending to a ferrule device side spaced from a ferrule body fluid side;
ii) an insulator extending to an insulator device side spaced from an insulator body fluid side, wherein, with insulator hermetically sealed to the ferrule in the ferrule opening, the insulator device and body fluid sides reside adjacent to the ferrule device and body fluid sides;
- iii) a first conductive pathway in the insulator extending to spaced apart insulator first conductive pathway device and body fluid side ends; and
- iv) a second conductive pathway in the insulator extending to spaced apart insulator second conductive pathway device and body fluid side ends,
- v) wherein the ferrule of the feedthrough is secured to the base annular edge to close the open end of the ceramic base; and c) a circuit board residing in the interior space of the ceramic base closed by the feedthrough, the circuit board extending to spaced apart circuit board first and second sides, wherein a circuit board first conductive pathway extends to spaced apart circuit board first conductive pathway first and second ends adjacent to the respective circuit board first and second sides, and a circuit board second conductive pathway extends to spaced apart circuit board second conductive pathway first and second ends adjacent to the respective circuit board first and second sides;

d) at least one electronic component supported by the circuit board, the electronic component having a first terminal spaced from a second terminal, wherein the circuit board first and second conductive pathway second ends are electrically connected to the respective first and second terminals of the at least one electronic component;

e) an anisotropic conductive layer disposed between the circuit board and the device side of the insulator of the feedthrough, the anisotropic conductive layer comprising an electrically insulative matrix supporting a plurality of electrically conductive particles, wherein the anisotropic conductive layer comprises:
- i) a first thickness that is longitudinally aligned with the insulator first conductive pathway device side end and the circuit board first conductive pathway first end adjacent to the circuit board first side, wherein the electrically conductive matrix of the anisotropic conductive layer residing in the first thickness has at least a first one of the plurality of electrically conductive particles in electrical contact with the insulator first conductive pathway device side end and the circuit board first conductive pathway first end to thereby provide electrical continuity from the insulator first conductive pathway body fluid side end to the circuit board first conductive pathway second end electrically connected to the first terminal of the at least one electronic component;
- ii) a second thickness that is longitudinally aligned with the insulator second conductive pathway device side end and the circuit board second conductive pathway first end adjacent to the circuit board first side, wherein the electrically conductive matrix of the anisotropic conductive layer residing in the second thickness has at least a second one of the plurality of electrically conductive particles in electrical contact with the insulator second conductive pathway device side end and the circuit board second conductive pathway first end to thereby provide electrical continuity from the insulator second conductive pathway body fluid side end to the circuit board second conductive pathway second end electrically connected to the second terminal of the at least one electronic component; and
- iii) a third thickness that is greater than the first and second thicknesses where the insulator and circuit board first conductive pathways are not longitudinally aligned and where insulator and circuit board second conductive pathways are not longitudinally aligned, wherein, even though the electrically conductive matrix supporting the plurality of electrically conductive particles resides in the third thickness, a third one of the plurality of electrically conductive particles is not in electrical contact with either of the insulator first conductive pathway and the circuit board first conductive pathway, and with either the insulator second conductive pathway and the circuit board second conductive pathway,
- iv) wherein the third, greater thickness of the anisotropic conductive layer electrically isolates at least the first and second ones of the plurality of electrically conductive particles from each other.

20. The IMD of claim 19, wherein at least one of the insulator first conductive pathway device side end and the circuit board first conductive pathway first side end is proud of the respective insulator device side end and the circuit board first side, and wherein the first thickness of the anisotropic conductive layer is longitudinally aligned with the at least one proud insulator first conductive pathway device side end and the circuit board first conductive pathway first side end, and wherein the third, greater thickness of the anisotropic conductive layer resides where the at least one proud insulator first conductive pathway device side end and the circuit board first conductive pathway first side end are not longitudinally aligned.

21. The IMD of claim 19, wherein the insulator first and second conductive pathways, and the circuit board first and second conductive pathways are individually comprised of a leadwire, an eyelet, and a substantially pure platinum at least partially filling the respective insulator and circuit board first and second passageways.

22. An implantable medical device (IMD), the IMD comprising:
- a) a ceramic base comprising a sidewall defining an open space and extending to a base annular edge surrounding a base open end;
- b) a ceramic lid closing the open end of the ceramic base, the lid extending to a lid annular edge meeting a lid device side spaced from a lid body fluid side, wherein at least a lid first conductive pathway extends to spaced apart lid first conductive pathway device and body fluid side ends, and a lid second conductive pathway extends to spaced apart lid second conductive pathway device and body fluid side ends;
- c) a circuit board residing in the interior space of the ceramic base closed by the lid, the circuit board extending to spaced apart circuit board first and second sides, wherein a circuit board first conductive pathway extends to spaced apart circuit board first conductive pathway first and second ends adjacent to the respective circuit board first and second sides, and a circuit board second conductive pathway extends to spaced apart circuit board second conductive pathway first and second ends adjacent to the respective circuit board first and second sides;
- d) a first electronic component supported by the circuit board, the first electronic component having at least a first terminal, wherein first conductive pathway second end is electrically connected to the first terminal of the first electronic component;

e) at least a second electronic component supported by the circuit board, the second electronic component having at least a second terminal, wherein second conductive pathway second end is electrically connected to the second terminal of the second electronic component; and f) an anisotropic conductive layer disposed between the circuit board first side and the device side of the ceramic lid, the anisotropic conductive layer comprising an electrically insulative matrix supporting a plurality of electrically conductive particles, wherein the anisotropic conductive layer comprises:

i) a first thickness that is longitudinally aligned with the lid first conductive pathway device side end and the circuit board first conductive pathway first end adjacent to the circuit board first ide, wherein the electrically conductive matrix of the anisotropic conductive layer residing in the first thickness has at least a first one of the plurality of electrically conductive particles in electrical contact with the lid first conductive pathway device side end and the circuit board first conductive pathway first end to thereby provide electrical continuity from the lid first conductive pathway body fluid side end to the circuit board first conductive pathway second end electrically connected to the first terminal of the first electronic component;

ii) a second thickness that is longitudinally aligned with the lid second conductive pathway device side end and the circuit board second conductive pathway first end adjacent to the circuit board first side, wherein the electrically conductive matrix of the anisotropic conductive layer residing in the second thickness has at least a second one of the plurality of electrically conductive particles in electrical contact with the lid second conductive pathway device side end and the circuit board second conductive pathway first end to thereby provide electrical continuity from the lid second conductive pathway body fluid side end to the circuit board second conductive pathway second end electrically connected to the second terminal of at least the second electronic component; and iii) a third thickness that is greater than the first and second thicknesses where the lid and circuit board first conductive pathways are not longitudinally aligned and where the lid and circuit board second conductive pathways are not longitudinally aligned, wherein, even though the electrically conductive matrix supporting the plurality of electrically conductive particles resides in the third thickness, a third one of the plurality of electrically conductive particles is not in electrical contact with either of the lid first conductive pathway and the circuit board first conductive pathway, and with either of the lid second conductive pathway and the circuit board second conductive pathway, iv) wherein the third, greater thickness of the anisotropic conductive layer electrically isolates at least the first and second ones of the plurality of electrically conductive particles from each other.

23. The IMD of claim 22, wherein the lid first and second conductive pathway device side ends and the circuit board first and second conductive pathways first and second side ends are proud of the respective lid device side end and the circuit board first side.

* * * * *